(12) United States Patent
Irani-cohen et al.

(10) Patent No.: US 12,216,127 B2
(45) Date of Patent: Feb. 4, 2025

(54) COMPOSITIONS, DEVICES, AND METHODS OF DEPRESSION SENSITIVITY TESTING

(71) Applicant: Biomerica, Inc., Irvine, CA (US)

(72) Inventors: Zackary Irani-cohen, Irvine, CA (US); Elisabeth Laderman, Irvine, CA (US)

(73) Assignee: Biomerica, Inc., Irvine, CA (US)

( * ) Notice: Subject to any disclaimer, the term of this patent is extended or adjusted under 35 U.S.C. 154(b) by 0 days.

(21) Appl. No.: 16/242,519

(22) Filed: Jan. 8, 2019

(65) Prior Publication Data

US 2019/0242904 A1 Aug. 8, 2019

Related U.S. Application Data

(63) Continuation of application No. PCT/US2017/041166, filed on Jul. 7, 2017.

(60) Provisional application No. 62/359,909, filed on Jul. 8, 2016.

(51) Int. Cl.
| | |
|---|---|
| *G01N 33/68* | (2006.01) |
| *G01N 33/543* | (2006.01) |
| *G01N 33/564* | (2006.01) |
| *G16H 20/60* | (2018.01) |
| *G16H 50/30* | (2018.01) |

(52) U.S. Cl.
CPC ....... *G01N 33/6854* (2013.01); *G01N 33/543* (2013.01); *G01N 33/564* (2013.01); *G16H 20/60* (2018.01); *G16H 50/30* (2018.01); *G01N 2800/02* (2013.01); *G01N 2800/24* (2013.01); *G01N 2800/304* (2013.01)

(58) Field of Classification Search
None
See application file for complete search history.

(56) References Cited

U.S. PATENT DOCUMENTS

| | | | |
|---|---|---|---|
| 4,208,479 | A | 6/1980 | Zuk et al. |
| 4,528,267 | A | 7/1985 | Calenoff et al. |
| 4,963,356 | A | 10/1990 | Calenoff et al. |
| 5,420,016 | A | 5/1995 | Boguslaski et al. |
| 5,833,976 | A | 11/1998 | Malefyt et al. |
| 6,152,887 | A | 11/2000 | Blume |
| 6,458,550 | B1 | 10/2002 | Luborsky |
| 6,858,398 | B2 | 2/2005 | Vojdani |
| 7,601,509 | B2 | 10/2009 | Power |
| 7,756,604 | B1 | 7/2010 | Davis et al. |
| 10,309,970 | B2 | 6/2019 | Laderman et al. |
| 10,788,498 | B2 | 9/2020 | Laderman et al. |
| 2002/0002270 | A1 | 1/2002 | Zinkowski et al. |
| 2003/0143627 | A1 | 7/2003 | Vojdani |
| 2004/0072272 | A1 | 4/2004 | Fine |
| 2004/0091843 | A1 | 5/2004 | Albro et al. |
| 2005/0181163 | A1 | 8/2005 | Kose |
| 2005/0187656 | A1 | 8/2005 | Walker et al. |
| 2005/0255533 | A1 | 11/2005 | Dantini et al. |
| 2006/0024813 | A1 | 2/2006 | Warthoe |
| 2006/0275846 | A1 | 12/2006 | Dorval et al. |
| 2007/0117217 | A1 | 5/2007 | Lal et al. |
| 2007/0122840 | A1 | 5/2007 | Cousins |
| 2007/0298447 | A1 | 12/2007 | Fine |
| 2008/0073430 | A1 | 3/2008 | Sickenius |
| 2009/0208984 | A1 | 8/2009 | Scott et al. |
| 2009/0253154 | A1 | 10/2009 | Vojdani |
| 2010/0190191 | A1 | 7/2010 | Dodds |
| 2010/0227340 | A1 | 9/2010 | Rozenshteyn et al. |
| 2011/0276344 | A1 | 11/2011 | Williams |
| 2011/0318717 | A1 | 12/2011 | Adamowicz |
| 2012/0005222 | A1 | 1/2012 | Bhagwan et al. |
| 2012/0058497 | A1* | 3/2012 | Suga ................ G01N 33/6893 435/7.92 |
| 2013/0085345 | A1 | 4/2013 | Geisner et al. |
| 2013/0183692 | A1* | 7/2013 | Dodds ............... G01N 33/6854 435/7.92 |
| 2014/0322678 | A1 | 10/2014 | Briancon et al. |
| 2014/0324899 | A1 | 10/2014 | Sherman et al. |
| 2014/0348935 | A1 | 11/2014 | Simon |
| 2015/0036138 | A1 | 2/2015 | Watson et al. |
| 2016/0022746 | A1 | 1/2016 | Lawley et al. |
| 2016/0058377 | A1 | 3/2016 | Butte et al. |

(Continued)

FOREIGN PATENT DOCUMENTS

| | | |
|---|---|---|
| CN | 101109750 A | 1/2008 |
| DE | 102013014080 A1 | 3/2015 |

(Continued)

OTHER PUBLICATIONS

Vigh-Conrad, PLoS ONE, 2010; 5: e10174; 11 pages total (Year: 2010).*
The website downloaded Sep. 21, 2022 from https://www.merriam-webster.com/thesaurus/plurality (Year: 2022).*
Extended European Search Report relating to corresponding European Application No. 17825010.6, dated Jan. 2, 2020, 12 pages.
Nonlinear Dynamics (Nonlinear Dynamics 2012; total 4 pages) (Year: 2012).
Benjamini et al., Behavioural Brain Research, 125:279-284, (2001).
Anbardan et al., J. Neurogastoenterol Motil., 18:70-77, (2012).
Yu, K., "Ubiquitous Allergens, <Do you eat right?>." Sichuan Science and Technology Press, 126-129, (Mar. 2013).

(Continued)

*Primary Examiner* — Christina M Borgeest
(74) *Attorney, Agent, or Firm* — WOMBLE BOND DICKINSON (US) LLP; Danielle L. Herritt; Mark R. DeLuca

(57) ABSTRACT

Contemplated test kits and methods for food sensitivity are based on rational-based selection of food preparations with established discriminatory p-value. Particularly preferred kits include those with a minimum number of food preparations that have an average discriminatory p-value of ≤0.07 as determined by their raw p-value or an average discriminatory p-value of ≤0.10 as determined by FDR multiplicity adjusted p-value. In further contemplated aspects, compositions and methods for food sensitivity are also stratified by gender to further enhance predictive value.

8 Claims, 21 Drawing Sheets

(56) References Cited

U.S. PATENT DOCUMENTS

| | | | |
|---|---|---|---|
| 2016/0145670 | A1 | 5/2016 | Steger et al. |
| 2018/0144821 | A1 | 5/2018 | Irani-Cohen et al. |
| 2018/0364252 | A1 | 12/2018 | Irani-Cohen et al. |
| 2019/0004039 | A1 | 1/2019 | Irani-Cohen et al. |
| 2019/0056408 | A1 | 2/2019 | Irani-Cohen et al. |
| 2019/0120835 | A1 | 4/2019 | Irani-cohen et al. |
| 2019/0145972 | A1 | 5/2019 | Irani-cohen et al. |
| 2019/0170767 | A1 | 6/2019 | Irani-cohen et al. |
| 2019/0170768 | A1 | 6/2019 | Irani-cohen et al. |
| 2019/0242886 | A1 | 8/2019 | Irani-cohen et al. |
| 2019/0242901 | A1 | 8/2019 | Laderman et al. |
| 2020/0003769 | A1 | 1/2020 | Irani-Cohen et al. |
| 2021/0172960 | A1 | 6/2021 | Laderman et al. |

FOREIGN PATENT DOCUMENTS

| | | | | |
|---|---|---|---|---|
| EP | 556745 | * | 8/1993 | ............ G01N 33/68 |
| EP | 1051626 | A1 | 11/2000 | |
| EP | 1548664 | A1 | 6/2005 | |
| HU | 1300497 | A2 | 3/2015 | |
| JP | 2011178679 | A | 9/2011 | |
| JP | 201479208 | A | 5/2014 | |
| JP | 2019-527823 | A | 10/2019 | |
| KR | 20090108968 | A | 10/2009 | |
| KR | 20130127145 | A | 11/2013 | |
| WO | WO-2002029415 | A1 | 4/2002 | |
| WO | WO-2004099785 | A1 | 11/2004 | |
| WO | WO-2008121406 | A1 | 10/2008 | |
| WO | WO-2009035529 | A1 | 3/2009 | |
| WO | WO-2010/049726 | A1 | 5/2010 | |
| WO | WO-2012/100070 | A3 | 12/2012 | |
| WO | 2016077808 | A1 | 5/2016 | |
| WO | WO 2018009845 | A1 | 1/2018 | |

OTHER PUBLICATIONS

Foster, A.P. et al., "Serum IgE and IgG responses to food antigens in normal and atopic dogs, and dogs with gastrointestinal disease", Veterinary Immunology and Immunopathology, 92(3-4), 113-124 (May 2003).

Traczyk, I. et al., "Concentration of lgG antibodies against food allergens in patients with irritable bowel syndrome and healthy individuals", Gastroenterology Review., 6(6), 382-387 (Dec. 2011).

Bohn, L. et al., Self-Reported Food-Related Gastrointestinal Symptoms in IBS Are Common and Associated With More Severe Symptoms and Reduced Quality of Life; Am J Gastroenterol., 108(5), 645-641 (May 2013).

Park, M-I. et al., Is there a role of food allergy in irritable bowel syndrome and functional dyspepsia? A systematic review, Neurogastroenterol Motil., 18, 595-607 (2006).

Cuomo, Rosario et al., Irritable bowel syndrome and food interaction, World Journal of Gastroenterology, 20(27), 8837-8845 (Jul. 21, 2014).

Zuo, X.L. et al., Alterations of food antigen-specific serum immunoglobulins G and E antibodies in patients with irritable bowel syndrome and functional dyspepsia, Clinical and Experimental Allergy, 37, 823-830 (2007).

Atkinson, W. et al., "Food elimination based on IgG antibodies in irritable bowel syndrome: a randomised controlled trial", Dept. of Medicine, University Hospital of South Manchester, Manchester, UK, 53, 1459-1464 (2004).

Monsbakken, K.W. et al., Perceived food intolerance in subjects with irritable bowel syndrome—otology, prevalence and consequences; European Journal of Clinical Nutrition; 667-672 (2006).

Zeng, Qiang et al. "Variable Food-Specific IgG Antibody Levels in Healthy and Symptomatic Chinese Adults," PLOS One, Research Article, Jan. 3, 2013.

Alpay et al. "Diet restriction in migraine, based on IgG against foods: A clinical double-blind, randomised, cross-over trial," Cephalalgia, 30:7, pp. 829-837, 2010.

Mitchell et al. "Randomised controlled trial of food elimination diet based on IgG antibodies for the Prevention of migraine like headaches," Nutrition Journal 2011, 10:85.

Zhai et al., "The Detection of Food-intolerance IgG Antibodies in Patient with Psoriasis," The Chinese Journal of Dermatoenereology, vol. 11 (2011).

Pizza, V. et al., "Food Intolerance in Migraine", Pharmacologyonline, 1:18-24 (2013).

Sun-Edelstein, Christina et al., "Foods and Supplements in the Management of Migraine Headaches", Clinical J. Pain, 25:446-452 (2009).

Gokani, T., Diet Restriction in Migraine, Based on IgG Against Foods: A Clinical Double-Blind, Randomised, Cross-Over Trial, Headache, 52:1056-1057 (2012).

Teixido, Michael et al., "Migraine-More than a Headache" (2014).

Constantinides et al., "Migraine and tension-type headache triggers in a Greek population," Arquivos De Neuro-Psiquiatria, 73(8):665-669, (Aug. 2015).

Szabo, I. et al., "Allergenicity of major cow's milk and peanut proteins determined by IgE and IgG immunoblotting", Allergy, 55, 42-49, 2008.

Cai, Chenwen et al, "Serological investigation of food specific immunoglobulin G antibodies in patients with inflammatory bowel disease", PLoS One, 9(11), e112154 (1-8), (Nov. 13, 2014).

Nigg, Joel T. et al., Restriction and Elimination Diets in ADHD Treatment, Child Adolesc Psychiatr Clin N. Am., 23(4), 937-953 (Oct. 2014).

Kleter, Gijs A. et al., "Screening of transgenic proteins expressed in transgenic food crops for the presence of short amino acid sequences identical to potential, IgE-binding linear epitopes of allergens", BMC Structural Biology, 2(8), 1-11, (Dec. 12, 2002).

Carvalho, Roberta Villas Boas et al., "Food Intolerance, Diet Composition, and Eating Patterns in Functional Dyspepsia Patients", Digestive Disease and Sciences, 55(1), 60-65 (2010).

Dias Batista, Emmanuelle et al., "Food intake assessment and quality of life in women with fibromyalgia", Revista Brasileira de Reumatologia, 56(2), 105-110 (Mar. 2016).

Sampson et al., "Relationship between food-specific IgE concentrations and the risk of positive food challenges in children and adolescents", J. Allergy Clin. Immunol., vol. 100(4): 444-451 (1997).

Sampson, HA, "Utility of food-specific IgE concentrations in predicting symptomatic food allergy", J. Allergy Clin, Immunol., vol. 107(5): 891-896 (2001).

Van Den Bogaerde, J. et al., "Gut mucosal response to food antigens in Crohn's disease", Alimentary Pharmacology & Therapeutics, vol. 16(11):1903-1915, (2002).

Zhou, Ming-Jin et al., "Investigation of 14 Food Allergen-Specific IgG Antibodies in 1299 Children", International Journal of Food Properties, vol. 19(1):25-30 (2016).

Takaaki, Kawaguchi et al., "Food antigen-induced immune responses in Crohn's disease patients and experimental colitis", Journal of Gastroenterology, vol. 50(4):394-405 (2014).

Correa, J.C., "Diagnosticos de Regresion Usando la FDR (Tasa de Descubrimientos Falsos)", Comunicaciones en Estadistica, vol. 3(2) (Dec. 2010).

Caselli, Michele et al., "A Possible Role of Food Intolerance in the Pathogenesis of Gastroesophageal Reflux Disease" The American Journal of Gastroenterology (Jan. 2009).

Caselli, Michele et al., "Test-based exclusion diets in gastroesophageal reflux disease patients: A randomized controlled pilot trial", The Word Journal of Gastroenterology, vol. 20(45): 17190-17195 (Jan. 2014).

Rodrigues Mariano De Almeida Rezende, Erica et al., "Clinical characteristics and sensitivity to food and inhalants among children with eosinophilic esophagitis", BMC Research Notes, BioMed Central Ltd., vol. 7(1): 1-7 (Jan. 2014).

Parker, Gordon et al., "Treatment-resistant depression: when antidepressant drug intolerance may indicate food intolerance", Australian and New Zealand Journal of Psychiatry, vol. 36(2): 263-265 (Apr. 2002).

Carr, Anitra C., "Depressed mood associated with gluten sensitivity—resolution of symptoms with a gluten free diet", The New Zealand Medical Journal, vol. 125(1366): 81-82 (Nov. 2012).

(56) References Cited

OTHER PUBLICATIONS

Karakula-Juchnowicz, H. et al., "The role of IgG hypersensitivity and changes in gut microbiota in the pathogenesis and therapy of depressive disorders", European Psychiatry, vol. 33 (Mar. 2016).
Dahiru, Tukur et al., "P-Value, A True Test of Statistical Significance? A Cautionary Note", Annals of Ibadan Postgraduate Medicine, vol. 6(1): 21-26 (2008).
ELISA Protocol, Thermo Scientific (2010).
Camilleri et al., Clin. Gastroenterol. Hepatol., vol. 6:772-781 (2008).
Payne, Sarah, Gender Medicine, vol. 1:18-28 (2004).
Pelsser, Lidy M.J., "ADHD, a Food-Induced Hypersensitivity Syndrome: in Quest of a Cause," retrieved from the Internet: URL:https://www.adhdenvoeding.nl/wp-content/uploads/2016/10/1.Proefschrift-ADHD-en-Voeding (2011).
Chinese Non-Patent Literature, Disease Enters Through the Mouth (2013), pp. 1-6.
International Search Report and the Written Opinion of corresponding International Application No. PCT/US2017/041166; completed on Oct. 18, 2017, mailed on Oct. 18, 2017.
U.S. Appl. No. 15/759,088, US 2019-0056408 A1, filed Feb. 21, 2019.
U.S. Appl. No. 15/875,900, US 2018-0144821 A1, filed May 24, 2018.
U.S. Appl. No. 16/013,774, US 2018-0364252 A1, filed Dec. 20, 2018.
U.S. Appl. No. 16/013,821, US 2019-0004039 A1, filed Jan. 3, 2019.
U.S. Appl. No. 16/124,473, US 2019-0120835 A1, filed Apr. 25, 2019.
U.S. Appl. No. 16/131,281, US 2019-0145972 A1, filed May 16, 2019.
U.S. Appl. No. 16/170,969, US 2019-0170767 A1, filed Jun. 6, 2019.
U.S. Appl. No. 16/171,154, US 2019-0170768 A1, filed Jun. 6, 2019.
U.S. Appl. No. 16/218,054, US 2019-0242886 A1, filed Aug. 8, 2019.
U.S. Appl. No. 16/385,322, US 2019-0242901 A1, filed Aug. 8, 2019.
U.S. Appl. No. 16/441,902, US 2020-0003769 A1, filed Jan. 2, 2020.
U.S. Appl. No. 17/000,102.
Herman, Patricia M. et al., "Evaluating the Clinical Relevance of Food Sensitivity Tests: A Single-Subject Experiment", Alternative Medicine Review, vol. 9(2): 198-207 (2004).
Leong, Daniel J. et al., "Nutraceuticals: Potential for Chondroprotection and Molecular Targeting of Osteoarthritis", International Journal of Molecular Sciences, vol. 14: 23063-23085 (2013).
Sanghi, Divya et al., "Elucidation of Dietary Risk Factors in Osteoarthritis Knee—A Case-Control Study", Journal of the American College of Nutrition, vol. 24(1): 15-20 (2015).
Aoki, Akiko et al., "Allergic Disorders in Primary Sjogren's Syndrome", foreign reference (in partial English), pp. 371-374 (2002).
Welen, Kerstin et al., "Functional Dyspepsia Affects Women More Than Men in Daily Life: A Case-Control Study in Primary Care," vol. 5(1): 62-73 (2008).
Tirant, Michael et al., "Therapeutic and etiologic considerations related to blood group and triggers in psoriasis—A retrospective study," Dermatologic Therapy, vol. 33, p. e13401 (2020).
Wang, De-xu et al., "Detection of food-specific IgE and IgG in sera from patients with psoriasis", foreign reference (in partial English), Zhonghua Pifuke Zazhi [ISSN: 0412-04030], vol. 46(10): 744-745 (2013).
Martin, Vincent T. et al., Diet and Headache: Part 1, Headache, vol. 56(9): 1543-1552 (2016).
Monro, Jean A. "Food allergy in migraine," Proct. Nutr. Soc., vol. 42, pp. 241-246 (1983).
Kobayashi, Kenji "Diagnosis and treatment of delayed-type food allegy", foreign reference (in partial English), The Allergy in Practice, No. 437:1260-1264 (2012).
Matsumoto, Yoshifuji, "Epidemiology of fibromyalgia", foreign reference (in partial English), Pharma Medica, vol. 24(6): 35-39 (2006).
U.S. Appl. No. 17/000,102, US 2021-0172960 A1, filed Jun. 10, 2021.
Wang, Jia, "Clinical significance of detecting serum specific IgE and IgG in patients with digestive system diseases", (w/partial English translation), Master Thesis of Dalian Medical University (2016).
Lavine, Elana, "Blood testing for sensitivity, allergy or intolerance to food", CMAJ, vol. 184(6): 666-668 (Apr. 3, 2012).
Liu, Zhen, "Food Hypersensitivity in Functional Dyspepsia in Rats", foreign reference (w/partial English translation), Medicine and Health Sciences, Chinese Master's Theses Full-text Database, Issue 4, (2013).
Ma, Xinling et al., "Food intolerance prevalence in active ulcerative colitis in southwest China" foreign reference (w/English translation), Asia Pacific Journal of Clinical Nutrition, vol. 25(3): 529-533 (2016).
De Theije, Caroline G. M., et al., "Food allergy and food-based therapies in neurodevelopmental disorders", Pediatric Allergy and Immunology, pp. 1-9 (2013).
Savilahti, E.M., et al., "Duration of clinical reactivity in cow's milk allergy is associated with levels of specific immunoglobulin G4 and immunoglobulin A antibodies to B-lactoglobulin", Clinical & Experimental Allergy, vol. 40, pp. 251-256 (2009).
Skerritt, John H. et al., "A Sensitive Monoclonal-antibody-based Test for Gluten Detection: Studies with Cooked or Processed Foods", Journal of the Science of Food and Agriculture, 36:980-986 (1985).
Haeney, MR et al., "Soya protein antibodies in man: their occurrence and possible relevance in coeliac disease", J. Clin. Pathol., vol. 35:319-322 (1982).
Giardino, Giuliana et al., "Gastrointestinal involvement in patients affected with 22q11.2 deletion syndrome", Scandinavian Journal of Gastroenterology, vol. 49:274-279, https//doi.org/10.3109/00365521.2013.855814 (2014).
Pelsser, Lidy M.J. et al., "Effects of a restricted elimination diet on the behaviour of children with attention-deficit hyperactivity disorder (INCA study): a randomised controlled trial", www.thelancet.com, vol. 377, pp. 494-503 (2011).
ImuPro: The tested Foods ata Glance, http://imupro.com/wp-content/uploads/Tested-foods-at-a-glance.pdf.
Lillestøl, Kristine, et al. (2010). "Anxiety and depression in patients with self-reported food hypersensitivity." General hospital psychiatry, vol. 32, No. 1, p. 42-48.

* cited by examiner

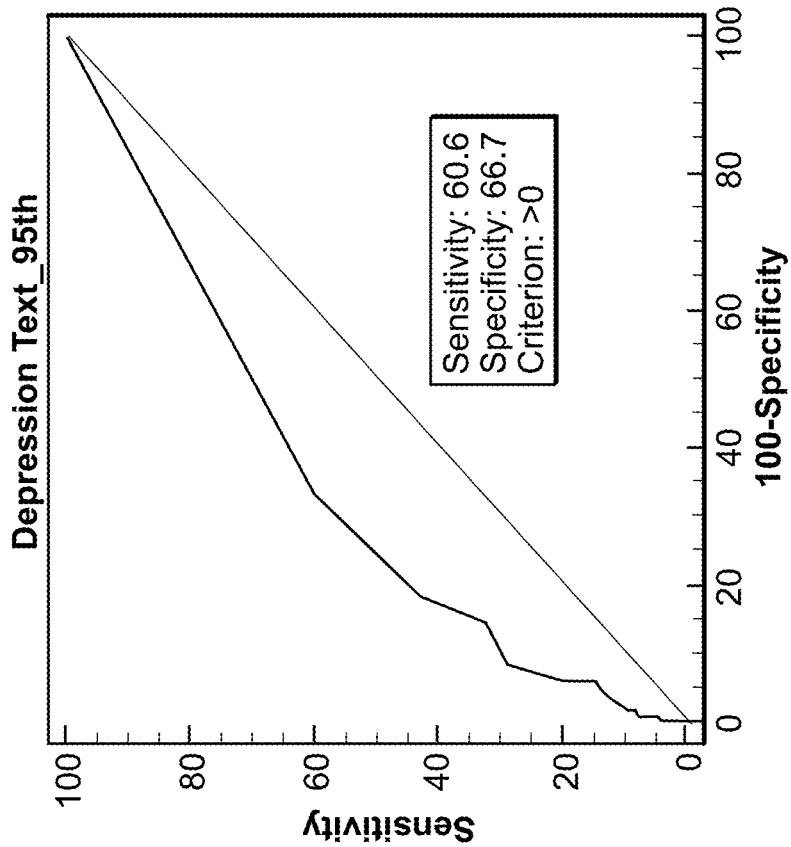
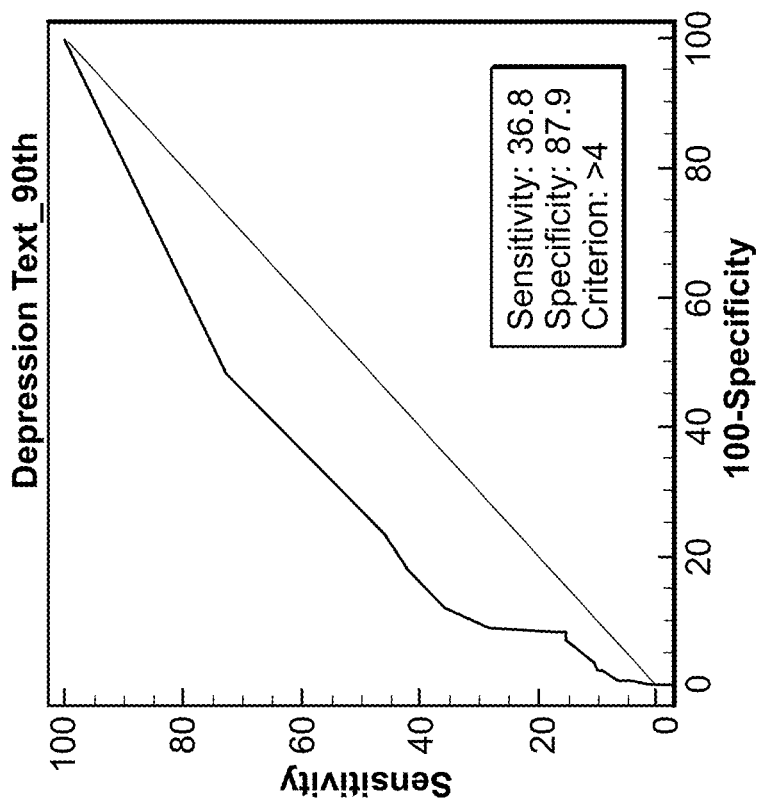
Figure 7B
Figure 7A

COMPOSITIONS, DEVICES, AND METHODS OF DEPRESSION SENSITIVITY TESTING

RELATED APPLICATIONS

This application is a Continuation of International Application No. PCT/US2017/041166, filed Jul. 7, 2017, which claims priority to United States Provisional Patent Application No. 62/359,909, filed Jul. 8, 2016, and entitled "Compositions, Devices, and Methods of Depression Sensitivity Testing." Each of the foregoing applications is incorporated herein by reference in its entirety.

FIELD OF THE INVENTION

The field of the invention is sensitivity testing for food intolerance, and especially as it relates to testing and possible elimination of selected food items as trigger foods for patients diagnosed with or suspected to have Depression.

BACKGROUND

The background description includes information that may be useful in understanding the present invention. It is not an admission that any of the information provided herein is prior art or relevant to the presently claimed invention, or that any publication specifically or implicitly referenced is prior art.

Food sensitivity, especially as it relates to Depression (a type of mental disorder), often presents with a pervasive and persistent low mood that is accompanied by low self-esteem and by a loss of interest or pleasure in normally enjoyable activities, and underlying causes of Depression are not well understood in the medical community. Most typically, Depression is diagnosed by a mental state examination, which is an assessment of the person's current mood and thought content. Unfortunately, treatment of Depression is often less than effective and may present new difficulties due to neurochemical modulatory effects. Elimination of one or more food items has also shown promise in at least reducing incidence and/or severity of the symptoms. However, Depression is often quite diverse with respect to dietary items triggering symptoms, and no standardized test to help identify trigger food items with a reasonable degree of certainty is known, leaving such patients often to trial-and-error.

While there are some commercially available tests and labs to help identify trigger foods, the quality of the test results from these labs is generally poor as is reported by a consumer advocacy group (e.g., world wide web.which.co.uk/news/2008/08/food-allergy-tests-could-risk-your-health-154711/). Most notably, problems associated with these tests and labs were high false positive rates, high false negative rates, high intra-patient variability, and inter-laboratory variability, rendering such tests nearly useless. Similarly, further inconclusive and highly variable test results were also reported elsewhere (Alternative Medicine Review, Vol. 9, No. 2, 2004: pp 198-207), and the authors concluded that this may be due to food reactions and food sensitivities occurring via a number of different mechanisms. For example, not all Depression patients show positive response to food A, and not all Depression patients show negative response to food B. Thus, even if a Depression patient shows positive response to food A, removal of food A from the patient's diet may not relieve the patient's Depression symptoms. In other words, it is not well determined whether food samples used in the currently available tests are properly selected based on the high probabilities to correlate sensitivities to those food samples to Depression.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, even though various tests for food sensitivities are known in the art, all or almost all of them suffer from one or more disadvantages. Therefore, there is still a need for improved compositions, devices, and methods of food sensitivity testing, especially for identification and possible elimination of trigger foods for patients identified with or suspected of having Depression.

SUMMARY

The subject matter described herein provides systems and methods for testing food intolerance in patients diagnosed with or suspected to have Depression. One aspect of the disclosure is a test kit for testing food intolerance in patients diagnosed with or suspected to have Depression. The test kit includes a plurality of distinct food preparations coupled to individually addressable respective solid carriers. The plurality of distinct food preparations have an average discriminatory p-value of ≤0.07 as determined by raw p-value or an average discriminatory p-value of ≤0.10 as determined by FDR multiplicity adjusted p-value. In some embodiments, the average discriminatory p-value is determined by a process, which includes comparing assay values of a first patient test cohort that is diagnosed with or suspected of having Depression with assay values of a second patient test cohort that is not diagnosed with or suspected of having Depression.

Another aspect of the embodiments described herein includes a method of testing food intolerance in patients diagnosed with or suspected to have Depression. The method includes a step of contacting a food preparation with a bodily fluid of a patient that is diagnosed with or suspected to have Depression. The bodily fluid is associated with gender identification. In certain embodiments, the step of contacting is performed under conditions that allow IgG from the bodily fluid to bind to at least one component of the food preparation. The method continues with a step of measuring IgG bound to the at least one component of the food preparation to obtain a signal, and then comparing the signal to a gender-stratified reference value for the food preparation using the gender identification to obtain a result. Then, the method also includes a step of updating or generating a report using the result.

Another aspect of the embodiments described herein includes a method of generating a test for food intolerance in patients diagnosed with or suspected to have Depression. The method includes a step of obtaining test results for a plurality of distinct food preparations. The test results are based on bodily fluids of patients diagnosed with or suspected to have Depression and bodily fluids of a control group not diagnosed with or not suspected to have Depression. The method also includes a step of stratifying the test results by gender for each of the distinct food preparations. Then the method continues with a step of assigning for a predetermined percentile rank a different cutoff value for male and female patients for each of the distinct food preparations.

Still another aspect of the embodiments described herein includes a use of a plurality of distinct food preparations coupled to individually addressable respective solid carriers in a diagnosis of Depression. The plurality of distinct food preparations are selected based on their average discriminatory p-value of ≤0.07 as determined by raw p-value or an average discriminatory p-value of ≤0.10 as determined by FDR multiplicity adjusted p-value.

Various objects, features, aspects and advantages of the embodiments described herein will become more apparent from the following detailed description of preferred embodiments, along with the accompanying drawing figures in which like numerals represent like components.

BRIEF DESCRIPTION OF THE DRAWINGS

Table 1 shows a list of food items from which food preparations can be prepared.

Table 2 shows statistical data of foods ranked according to 2-tailed FDR multiplicity-adjusted p-values.

Table 3 shows statistical data of ELISA score by food and gender.

Table 4 shows cutoff values of foods for a predetermined percentile rank.

Figure 1A:
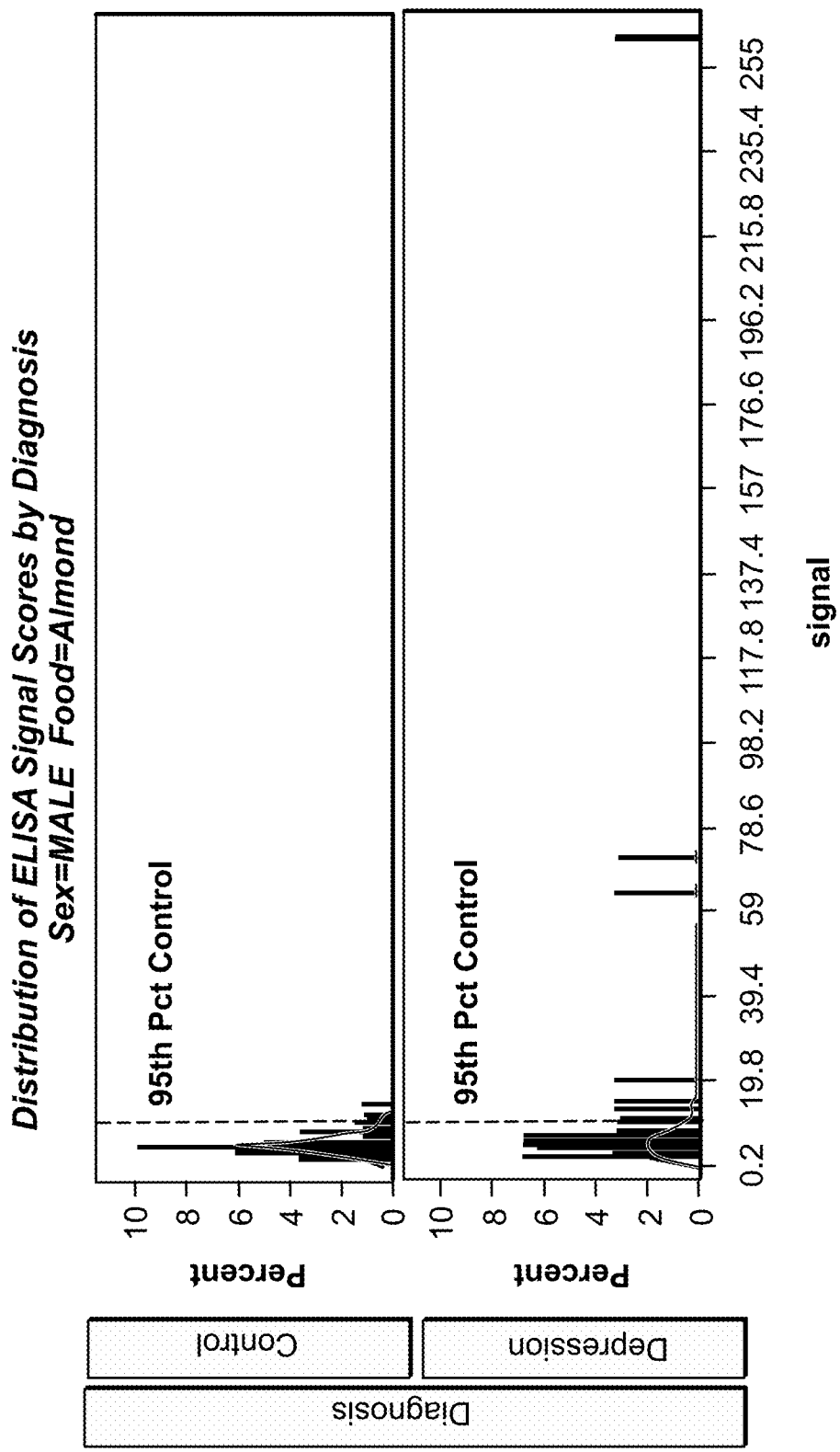

FIG. 1A illustrates ELISA signal score of male Depression patients and control tested with almond.

Figure 1B:
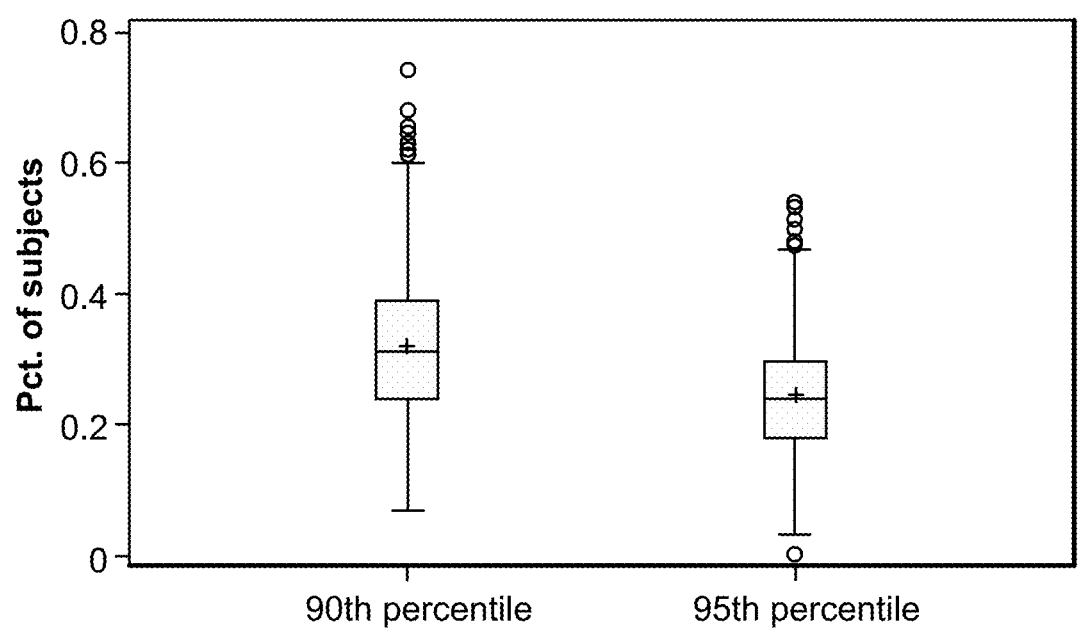

FIG. 1B illustrates a distribution of percentage of male Depression subjects exceeding the $90^{th}$ and $95^{th}$ percentile tested with almond.

Figure 1C:
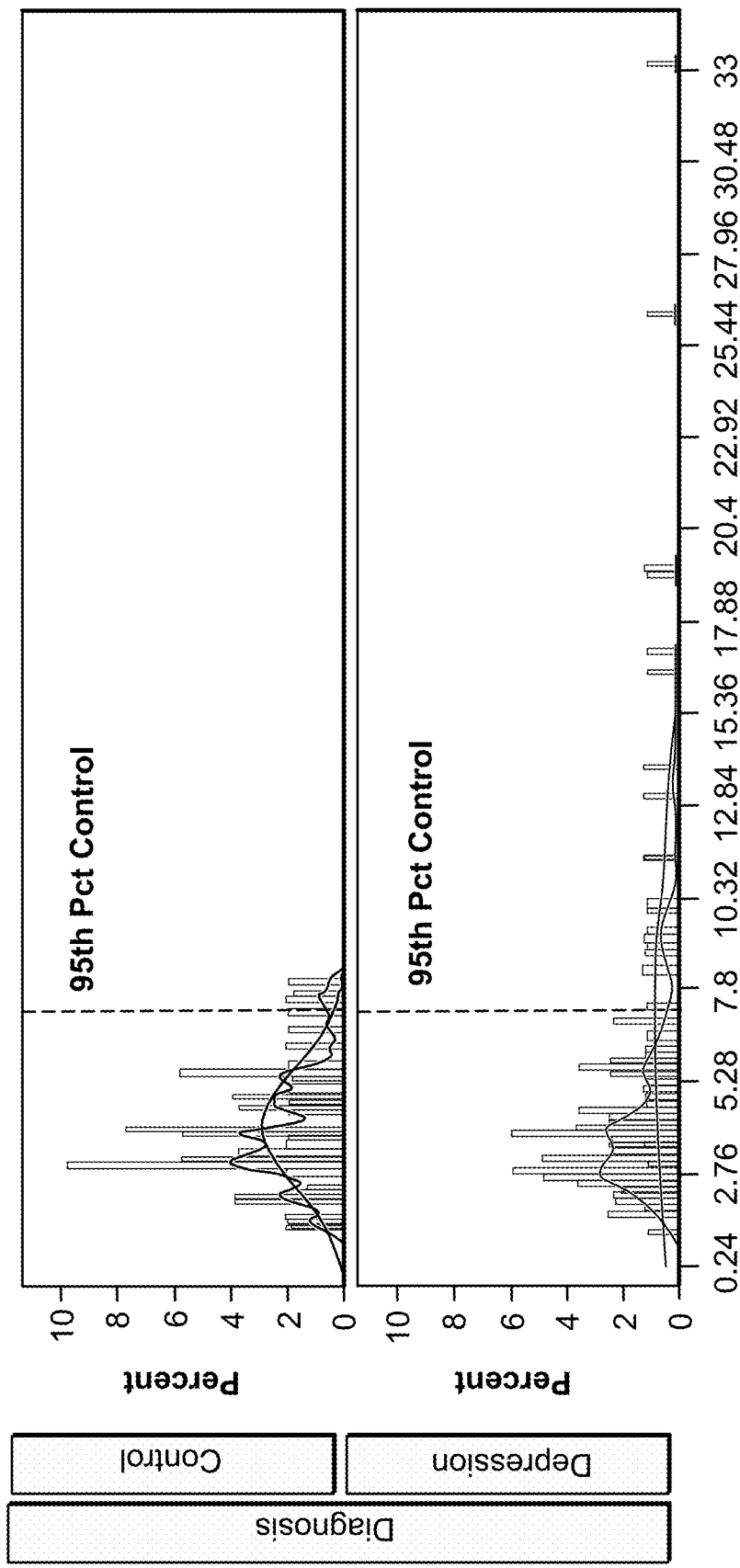

FIG. 1C illustrates a signal distribution in women along with the $95^{th}$ percentile cutoff as determined from the female control population tested with almond.

Figure 1D:
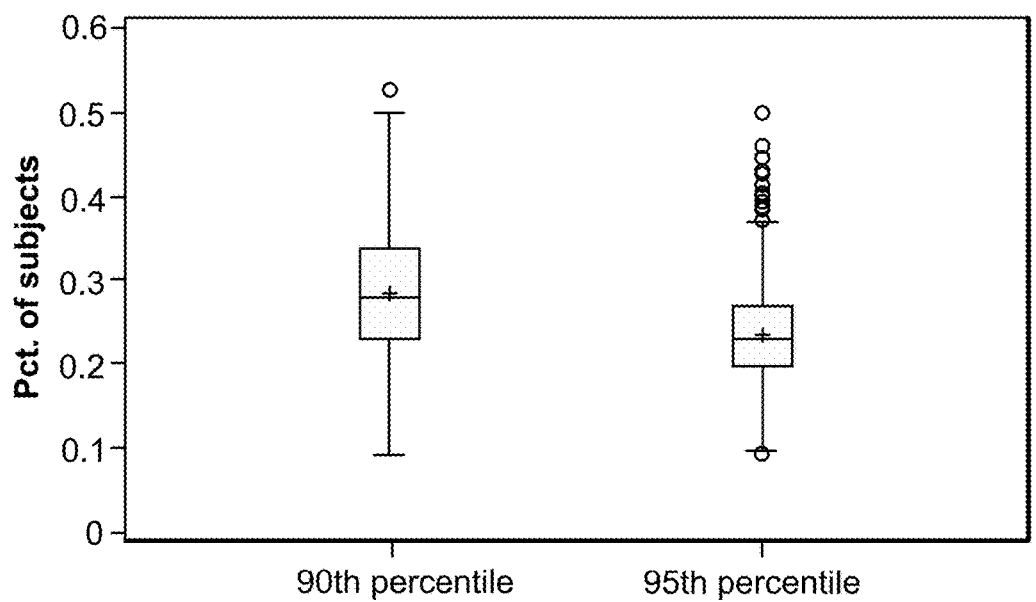

FIG. 1D illustrates a distribution of percentage of female Depression subjects exceeding the $90^{th}$ and $95^{th}$ percentile tested with almond.

Figure 2A:
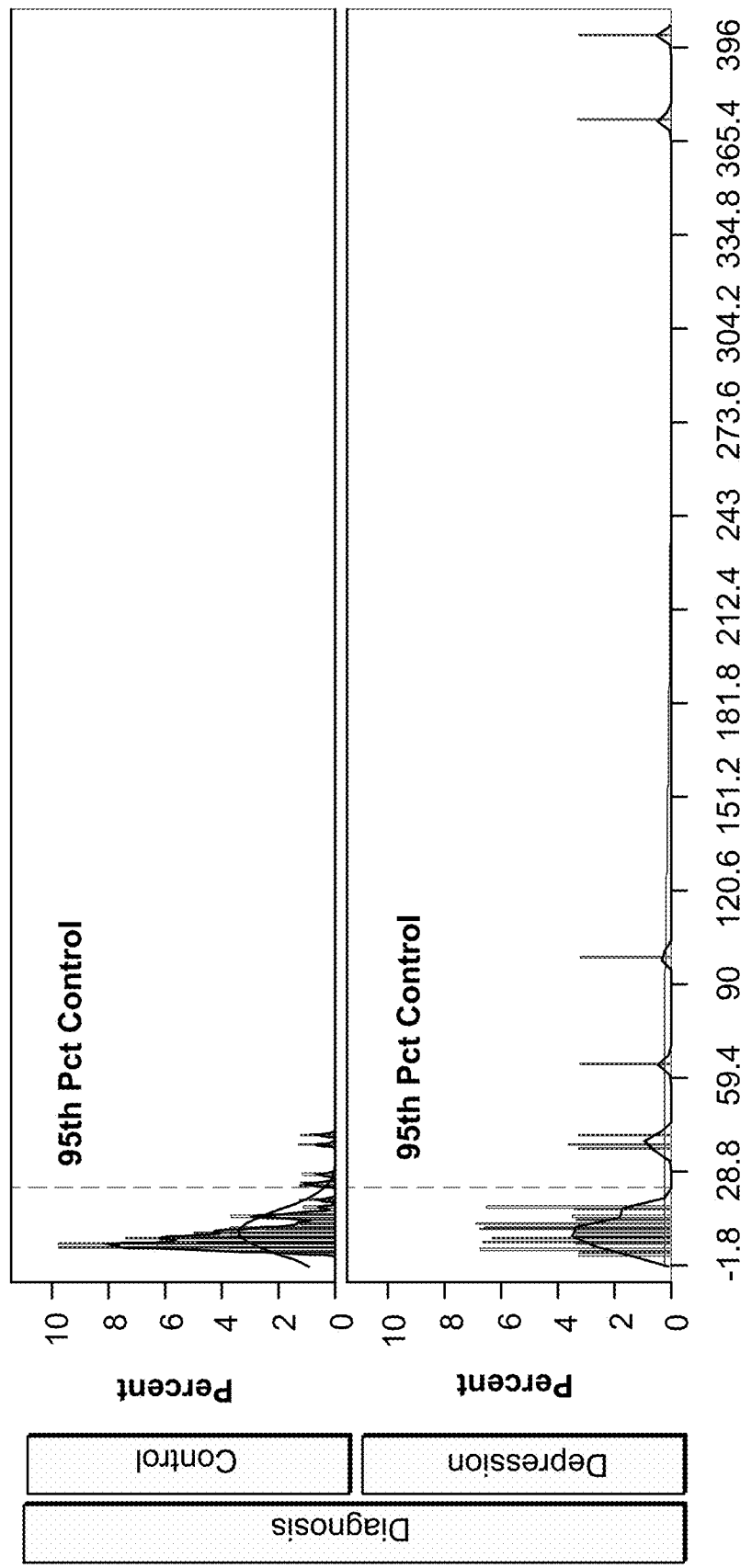

FIG. 2A illustrates ELISA signal score of male Depression patients and control tested with tomato.

Figure 2B:
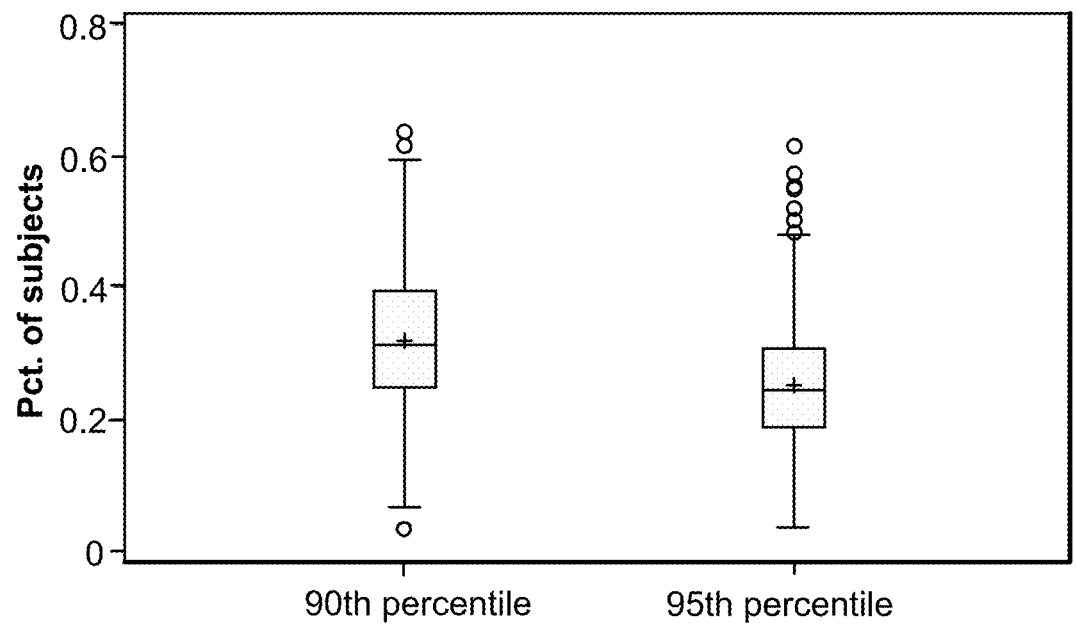

FIG. 2B illustrates a distribution of percentage of male Depression subjects exceeding the $90^{th}$ and $95^{th}$ percentile tested with tomato.

Figure 2C:
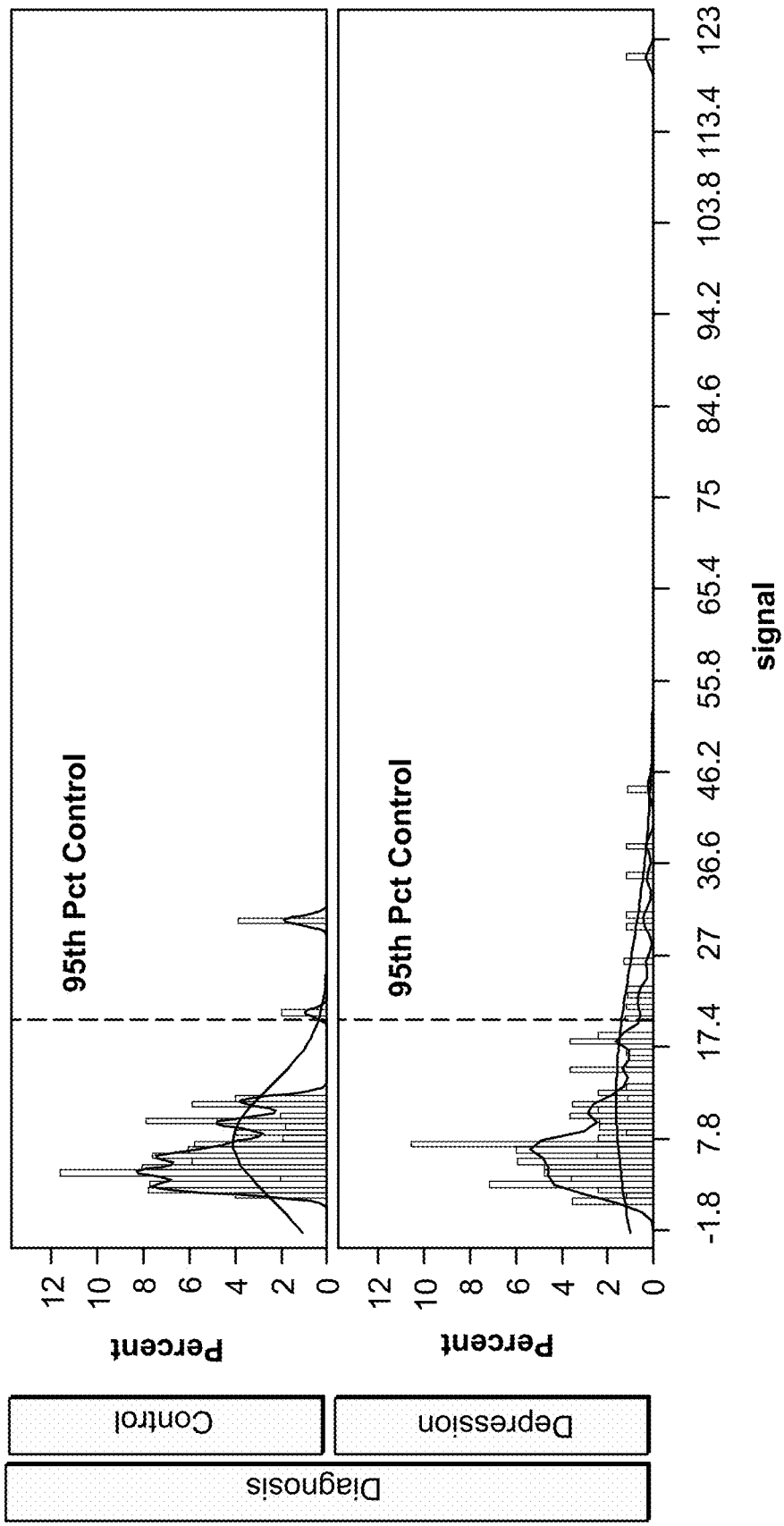

FIG. 2C illustrates a signal distribution in women along with the $95^{th}$ percentile cutoff as determined from the female control population tested with tomato.

Figure 2D:
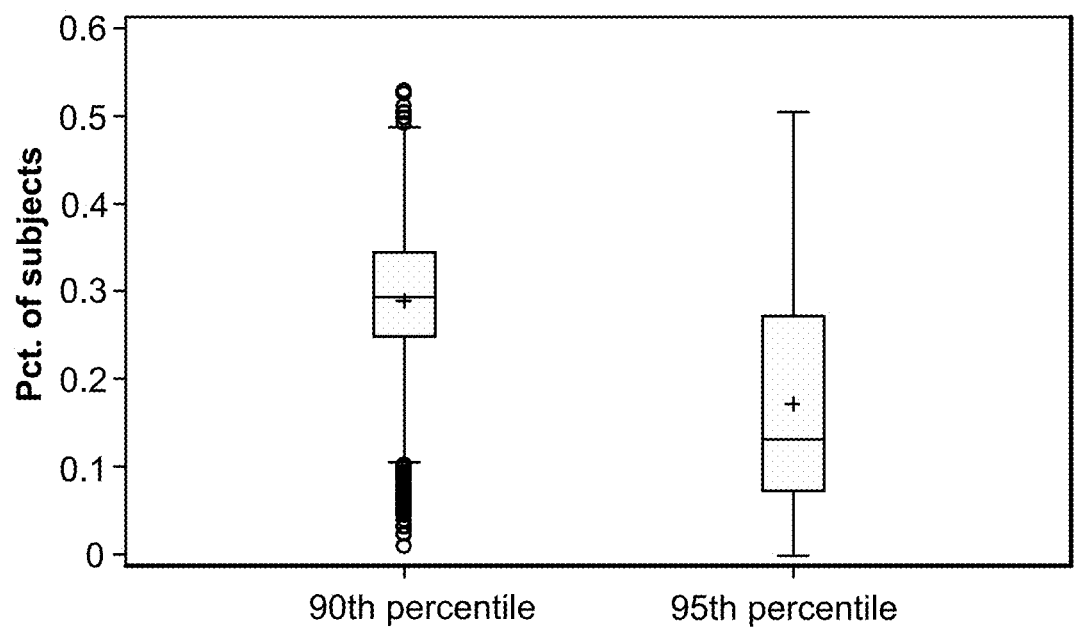

FIG. 2D illustrates a distribution of percentage of female Depression subjects exceeding the $90^{th}$ and $95^{th}$ percentile tested with tomato.

Figure 3A:
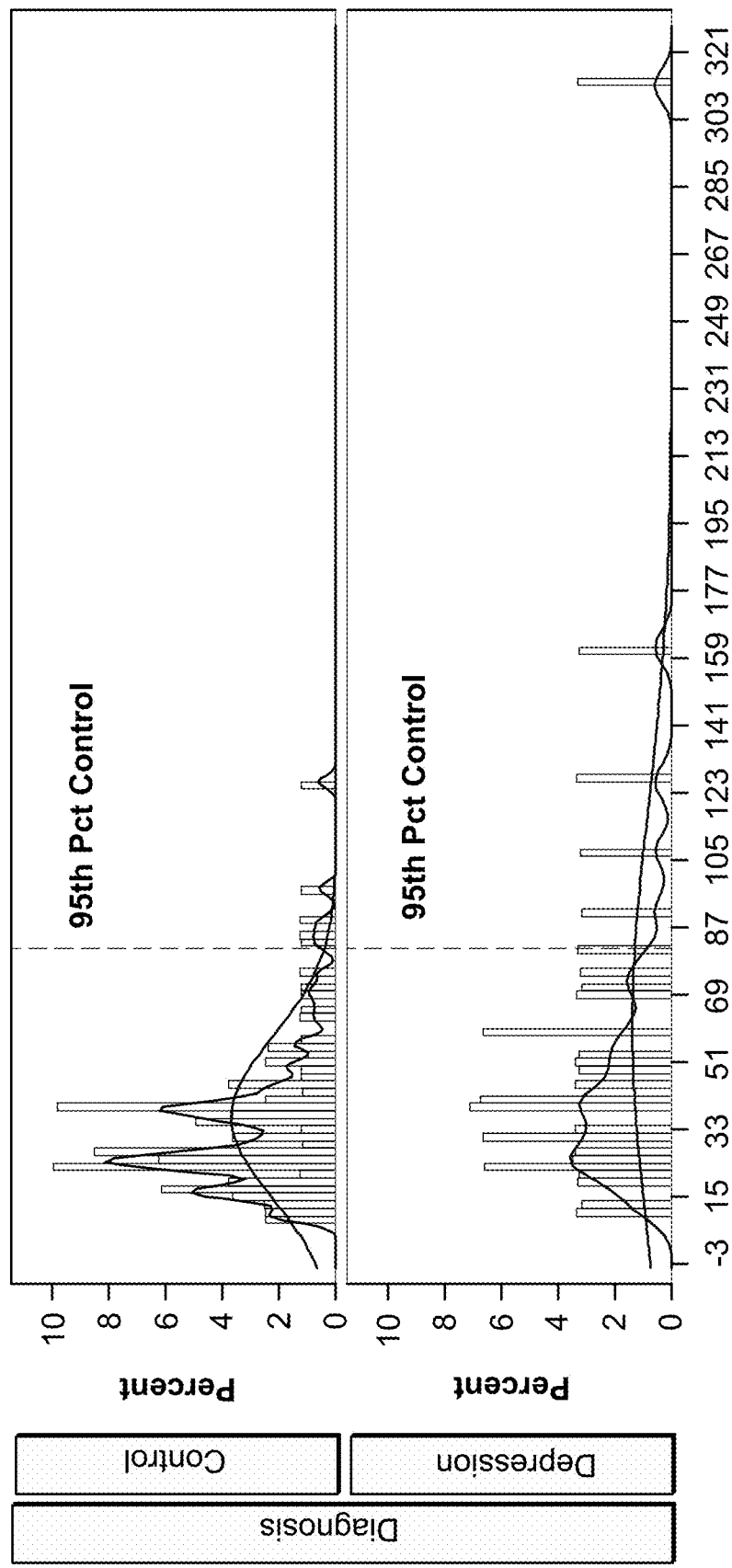

FIG. 3A illustrates ELISA signal score of male Depression patients and control tested with tobacco.

Figure 3B:
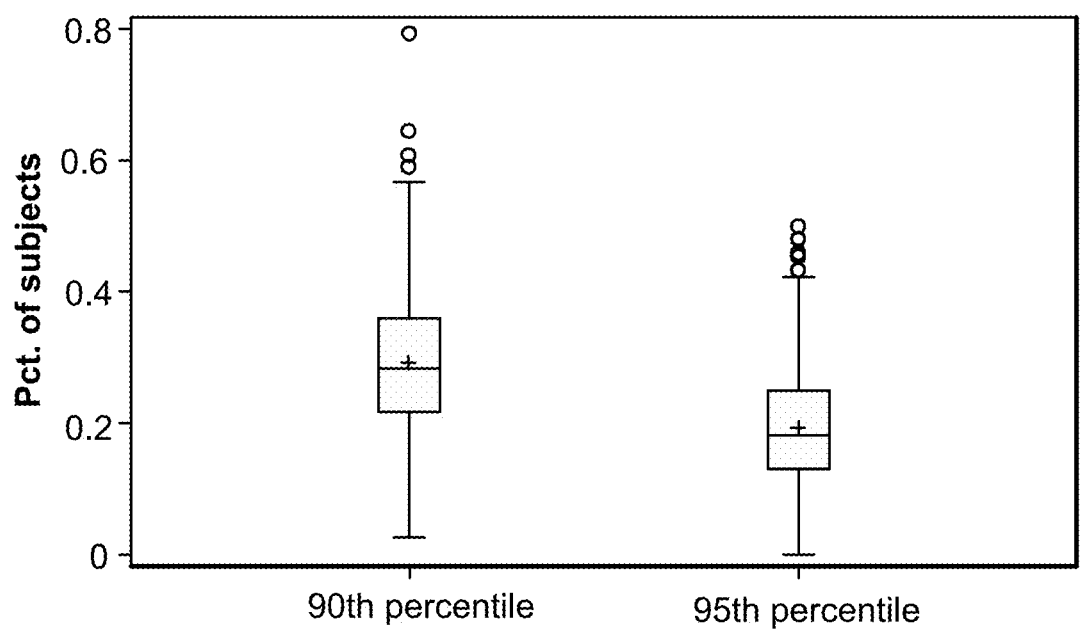

FIG. 3B illustrates a distribution of percentage of male Depression subjects exceeding the $90^{th}$ and $95^{th}$ percentile tested with tobacco.

Figure 3C:
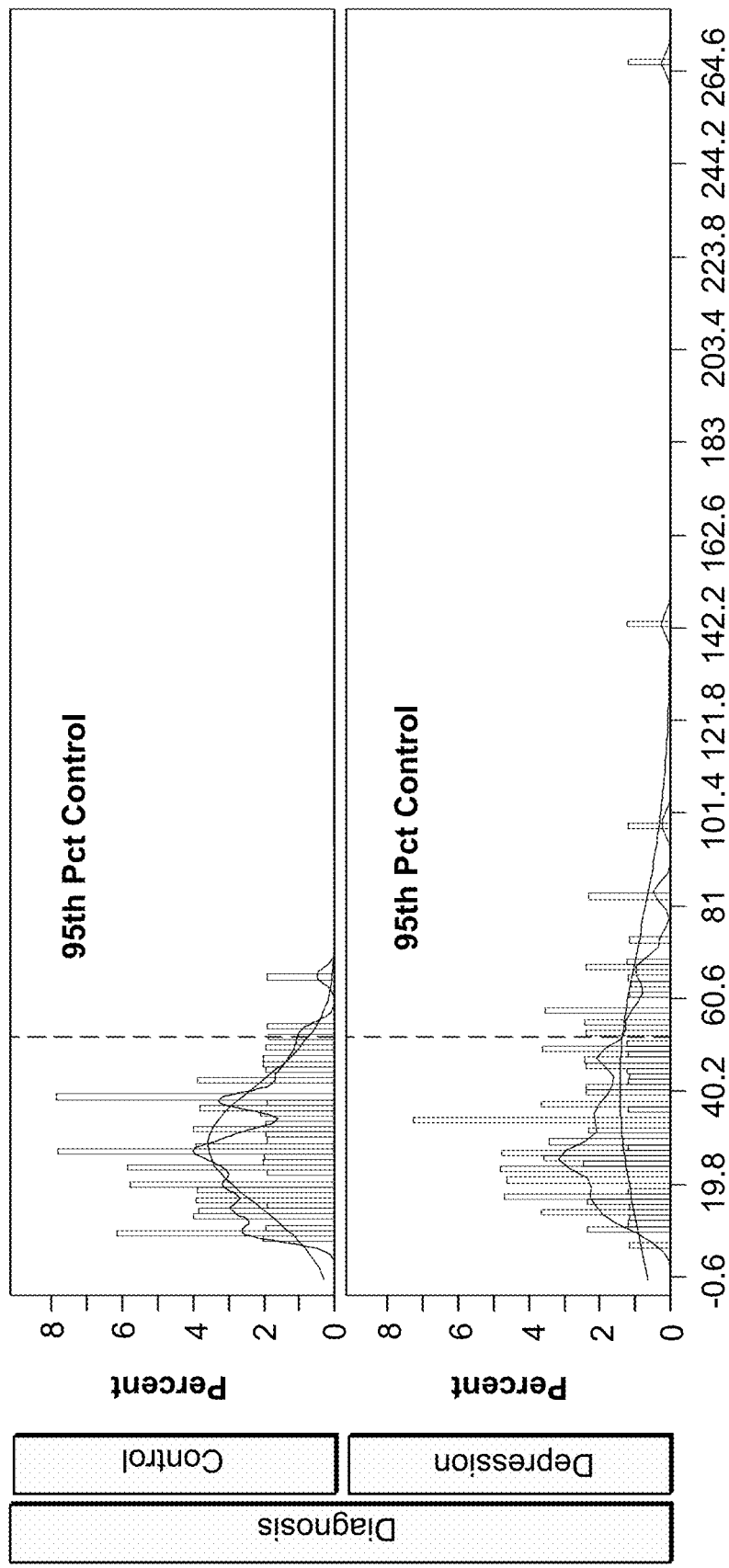

FIG. 3C illustrates a signal distribution in women along with the $95^{th}$ percentile cutoff as determined from the female control population tested with tobacco.

Figure 3D:
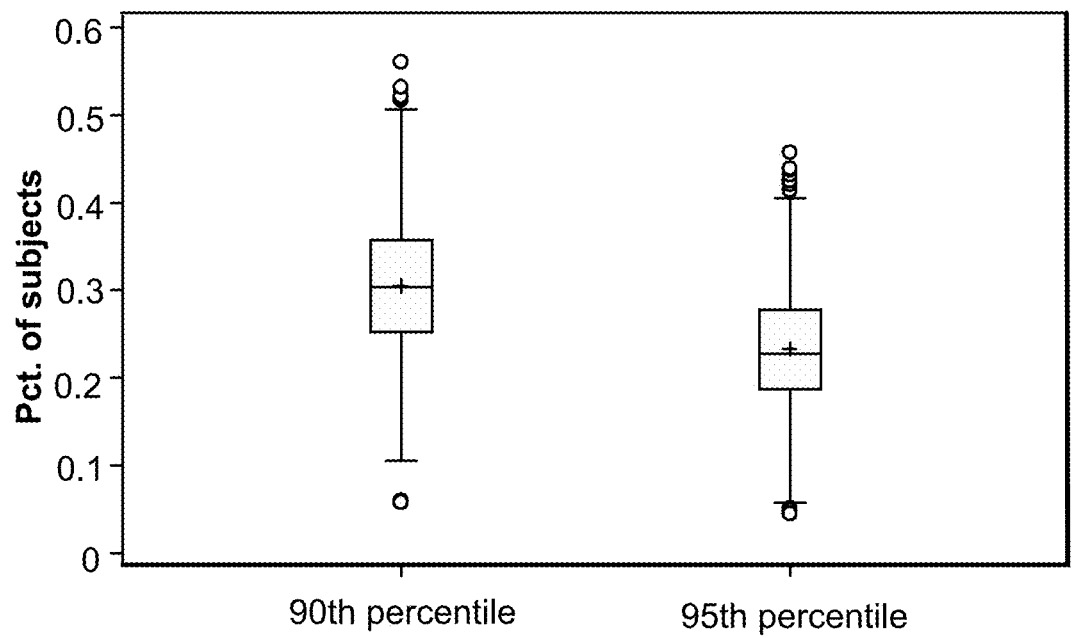

FIG. 3D illustrates a distribution of percentage of female Depression subjects exceeding the $90^{th}$ and $95^{th}$ percentile tested with tobacco.

Figure 4A:
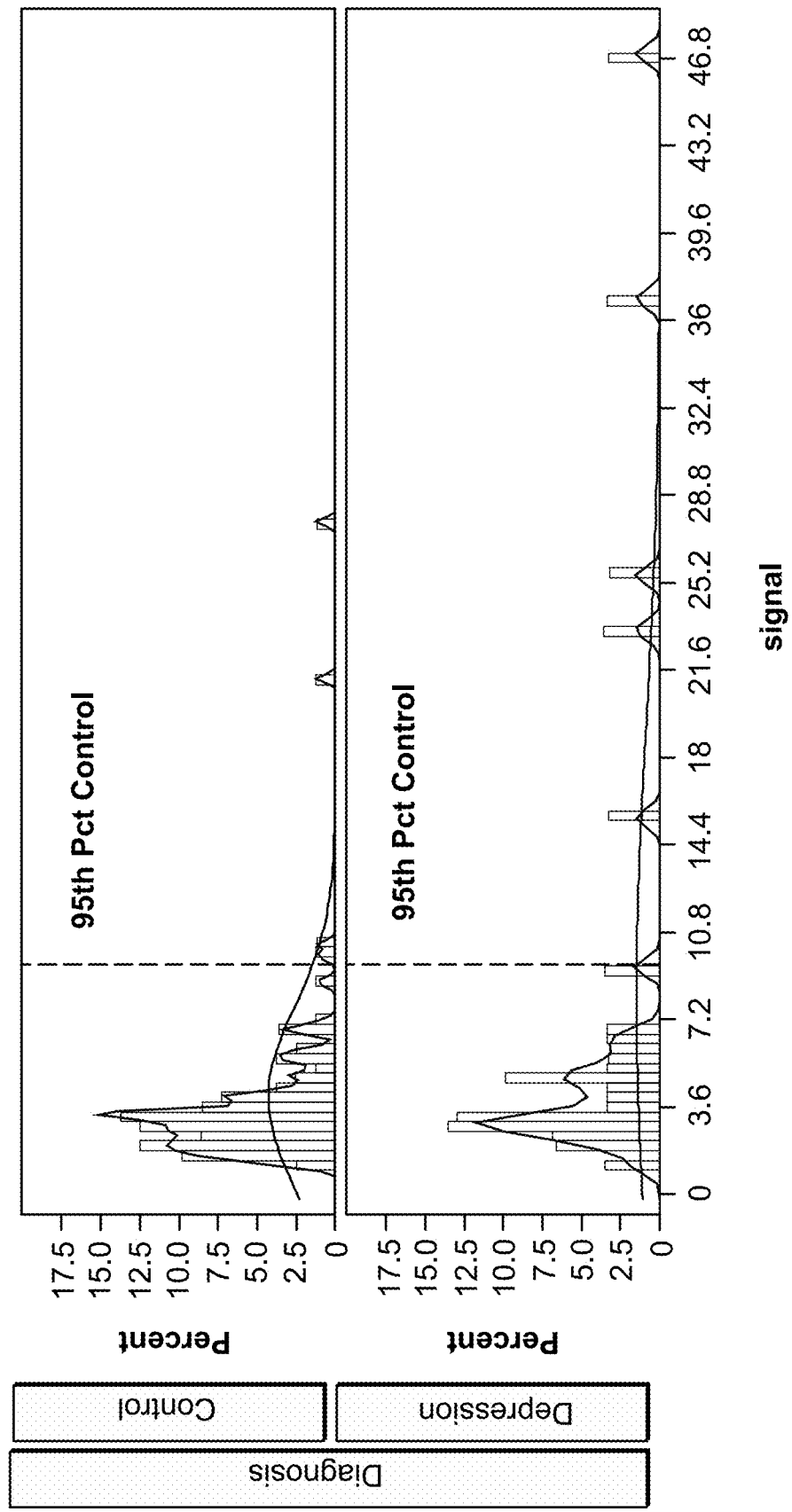

FIG. 4A illustrates ELISA signal score of male Depression patients and control tested with carrot.

Figure 4B:
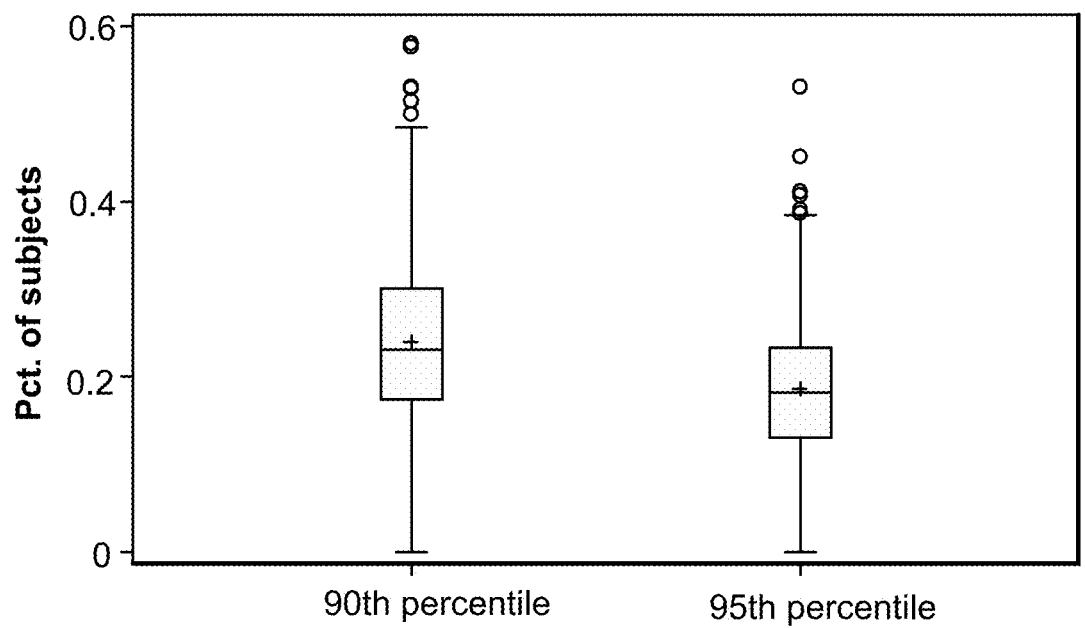

FIG. 4B illustrates a distribution of percentage of male Depression subjects exceeding the $90^{th}$ and $95^{th}$ percentile tested with carrot.

Figure 4C:
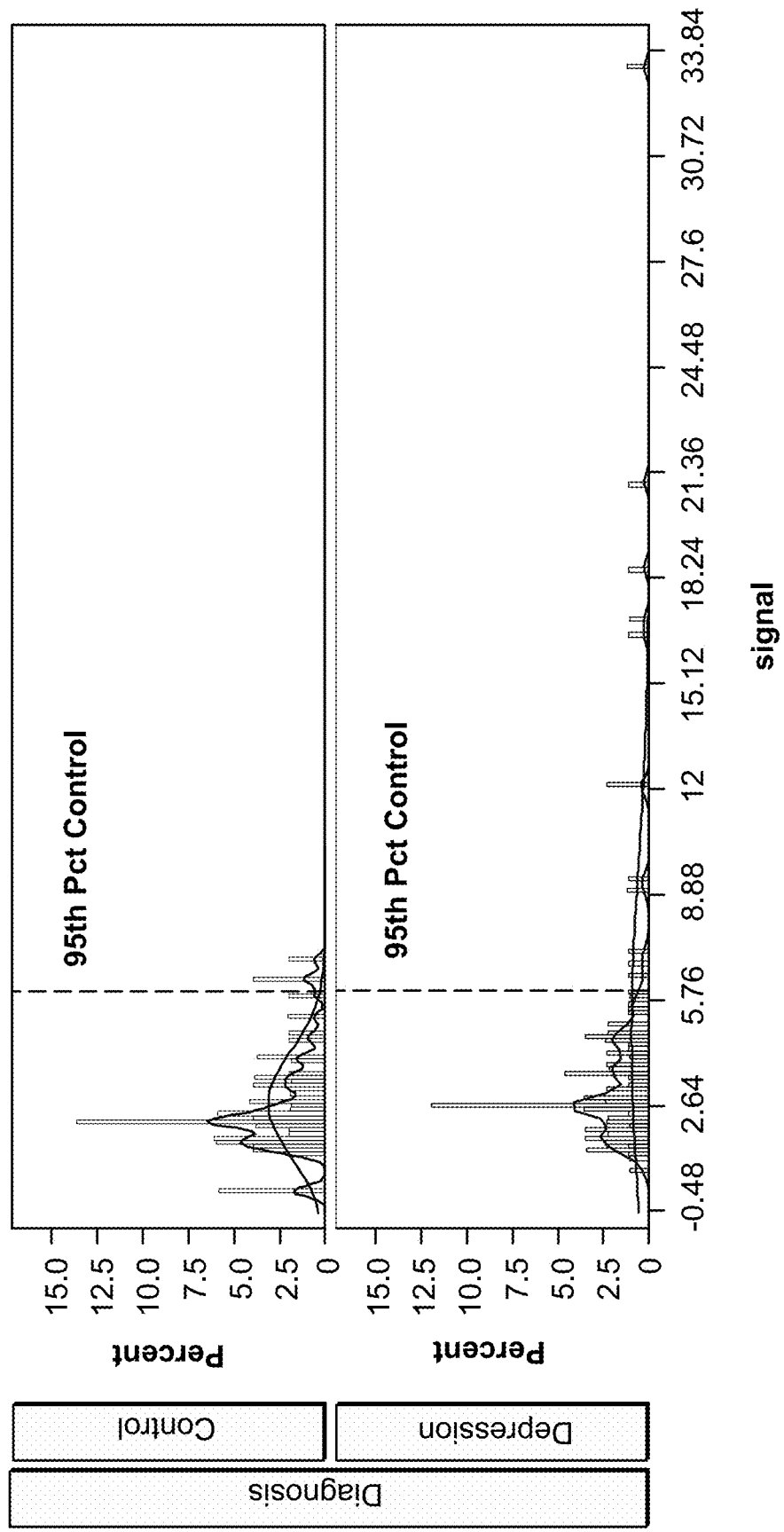

FIG. 4C illustrates a signal distribution in women along with the $95^{th}$ percentile cutoff as determined from the female control population tested with carrot.

Figure 4D:
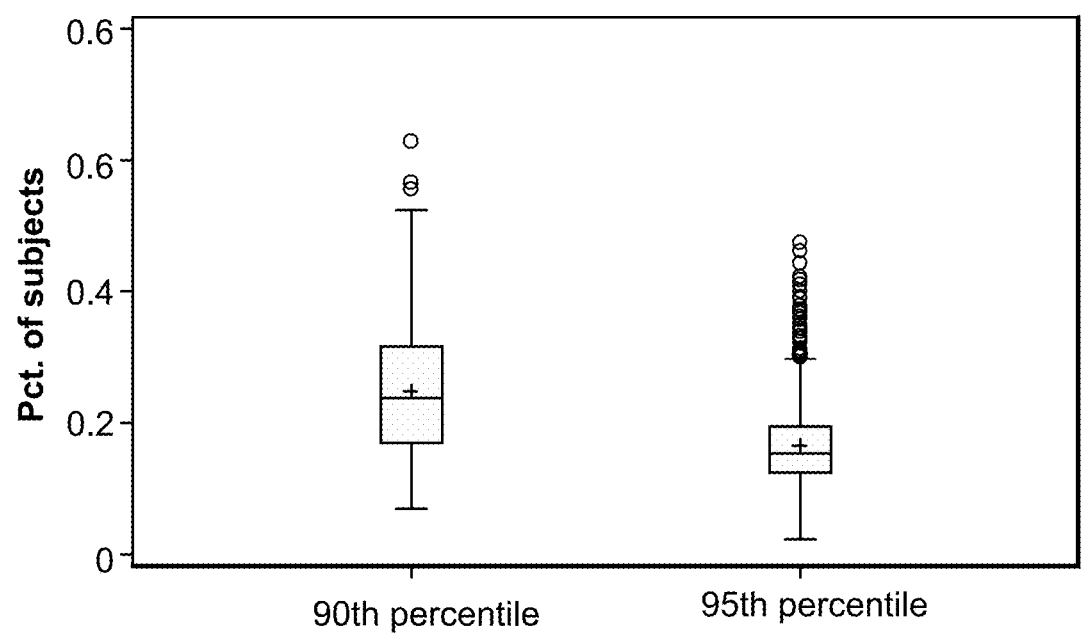

FIG. 4D illustrates a distribution of percentage of female Depression subjects exceeding the $90^{th}$ and $95^{th}$ percentile tested with carrot.

Figure 5A:
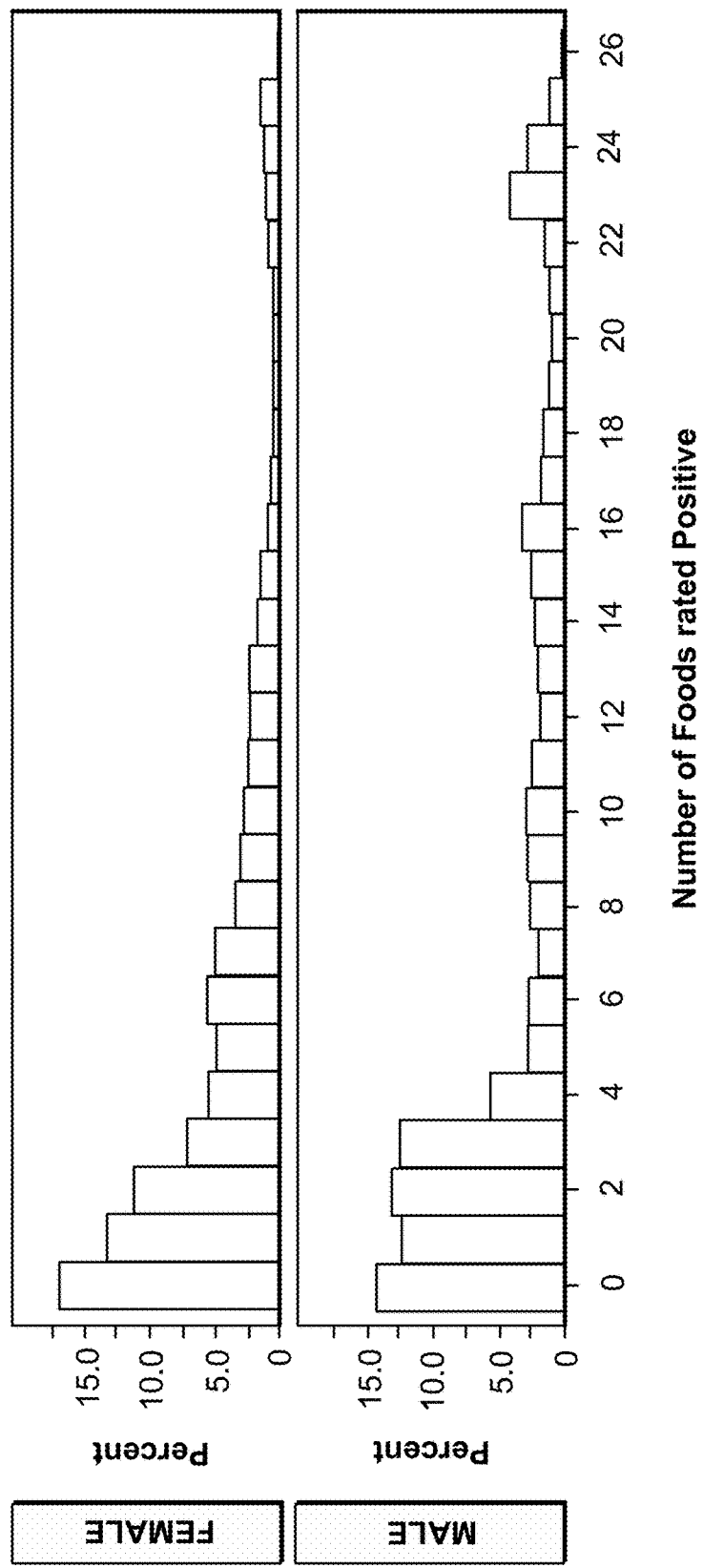

FIG. 5A illustrates distributions of Depression subjects by number of foods that were identified as trigger foods at the $90^{th}$ percentile.

Figure 5B:
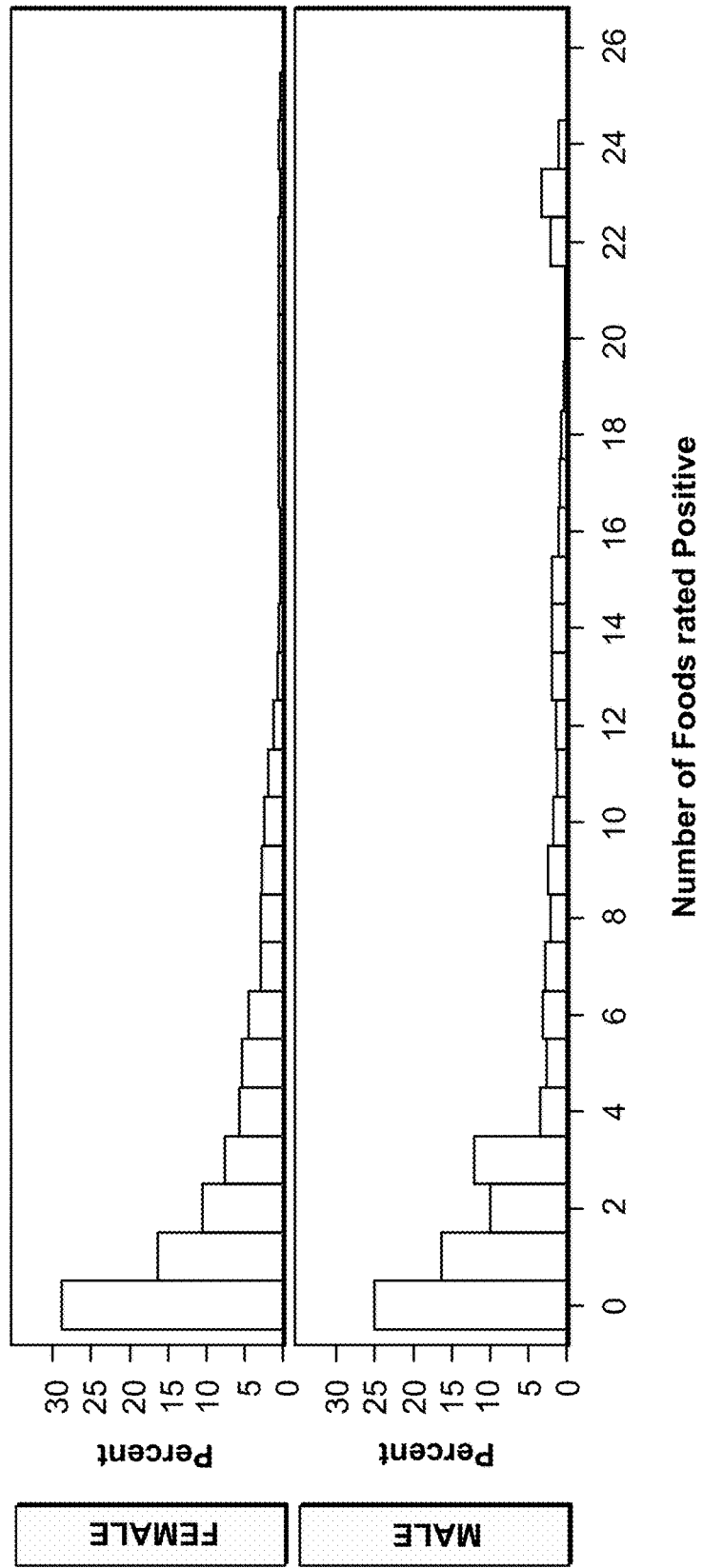

FIG. 5B illustrates distributions of Depression subjects by number of foods that were identified as trigger foods at the $95^{th}$ percentile.

Table 5A shows raw data of Depression patients and control with number of positive results based on the $90^{th}$ percentile.

Table 5B shows raw data of Depression patients and control with number of positive results based on the $95^{th}$ percentile.

Table 6A shows statistical data summarizing the raw data of Depression patient populations shown in Table 5A.

Table 6B shows statistical data summarizing the raw data of Depression patient populations shown in Table 5B.

Table 7A shows statistical data summarizing the raw data of control populations shown in Table 5A.

Table 7B shows statistical data summarizing the raw data of control populations shown in Table 5B.

Table 8A shows statistical data summarizing the raw data of Depression patient populations shown in Table 5A transformed by logarithmic transformation.

Table 8B shows statistical data summarizing the raw data of Depression patient populations shown in Table 5B transformed by logarithmic transformation.

Table 9A shows statistical data summarizing the raw data of control populations shown in Table 5A transformed by logarithmic transformation.

Table 9B shows statistical data summarizing the raw data of control populations shown in Table 5B transformed by logarithmic transformation.

Table 10A shows statistical data of an independent T-test to compare the geometric mean number of positive foods between the Depression and non-Depression samples based on the $90^{th}$ percentile.

Table 10B shows statistical data of an independent T-test to compare the geometric mean number of positive foods between the Depression and non-Depression samples based on the $95^{th}$ percentile.

Table 11A shows statistical data of a Mann-Whitney test to compare the geometric mean number of positive foods between the Depression and non-Depression samples based on the $90^{th}$ percentile.

Table 11B shows statistical data of a Mann-Whitney test to compare the geometric mean number of positive foods between the Depression and non-Depression samples based on the $95^{th}$ percentile.

Figure 6A:
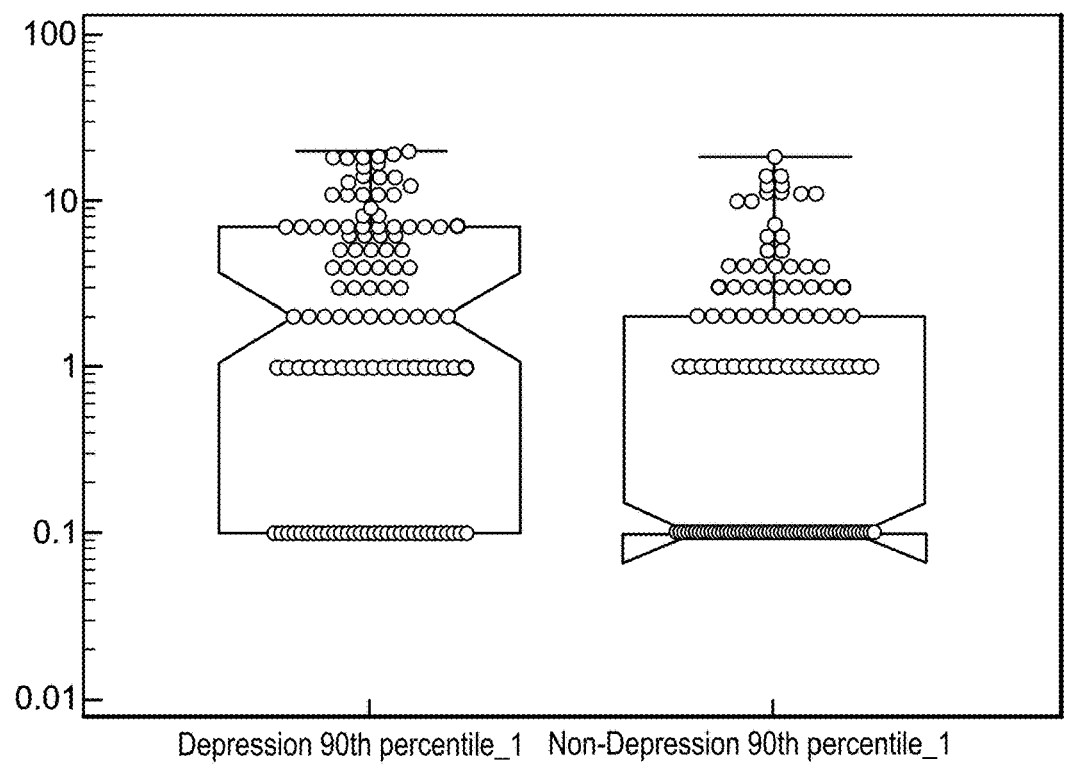

FIG. 6A illustrates a box and whisker plot of data shown in Table 5A.

Figure 6B:
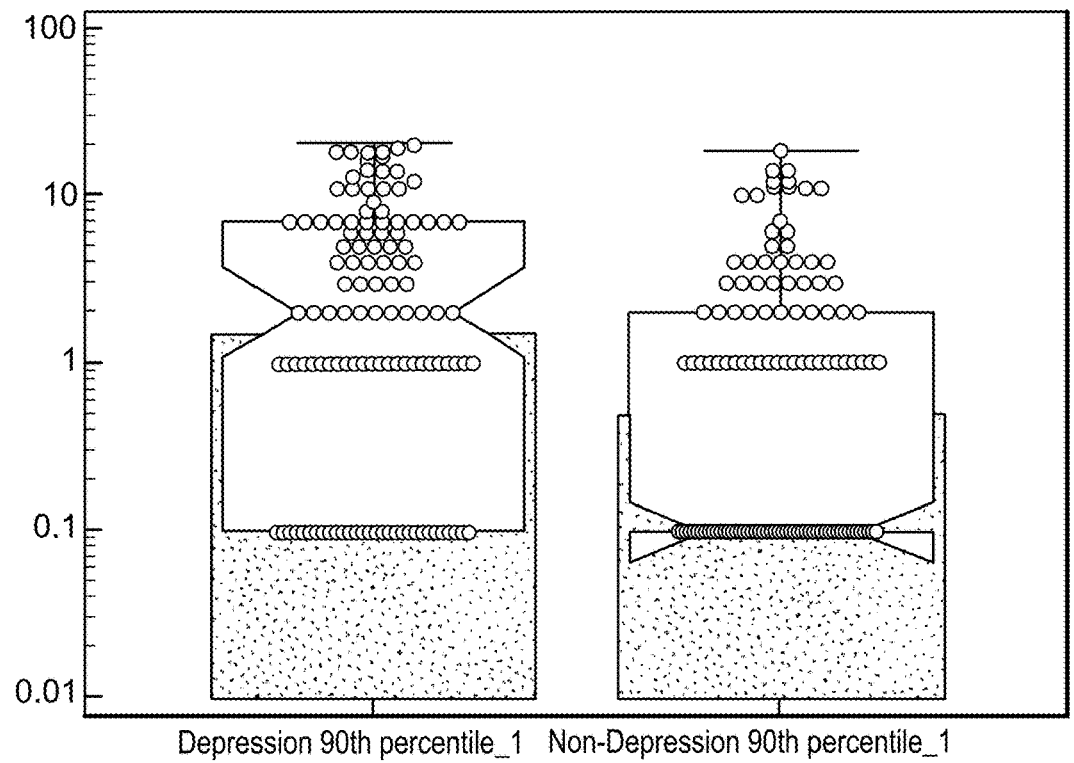

FIG. 6B illustrates a notched box and whisker plot of data shown in Table 5A.

Figure 6C:
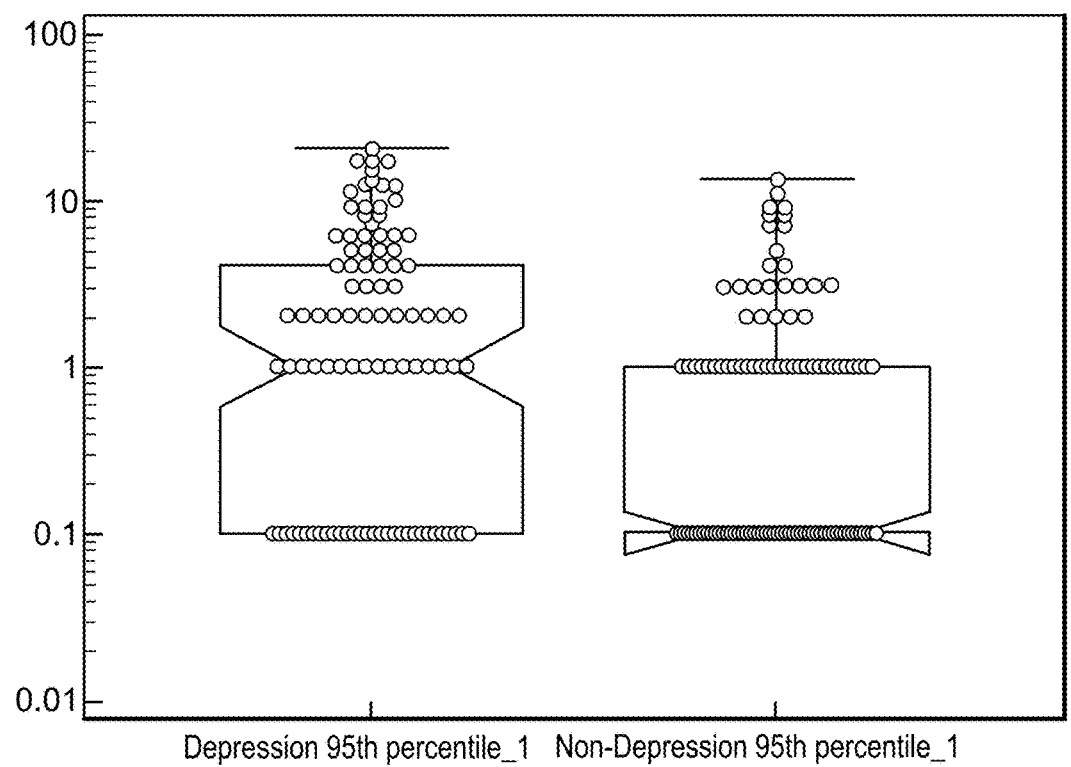

FIG. 6C illustrates a box and whisker plot of data shown in Table 5B.

Figure 6D:
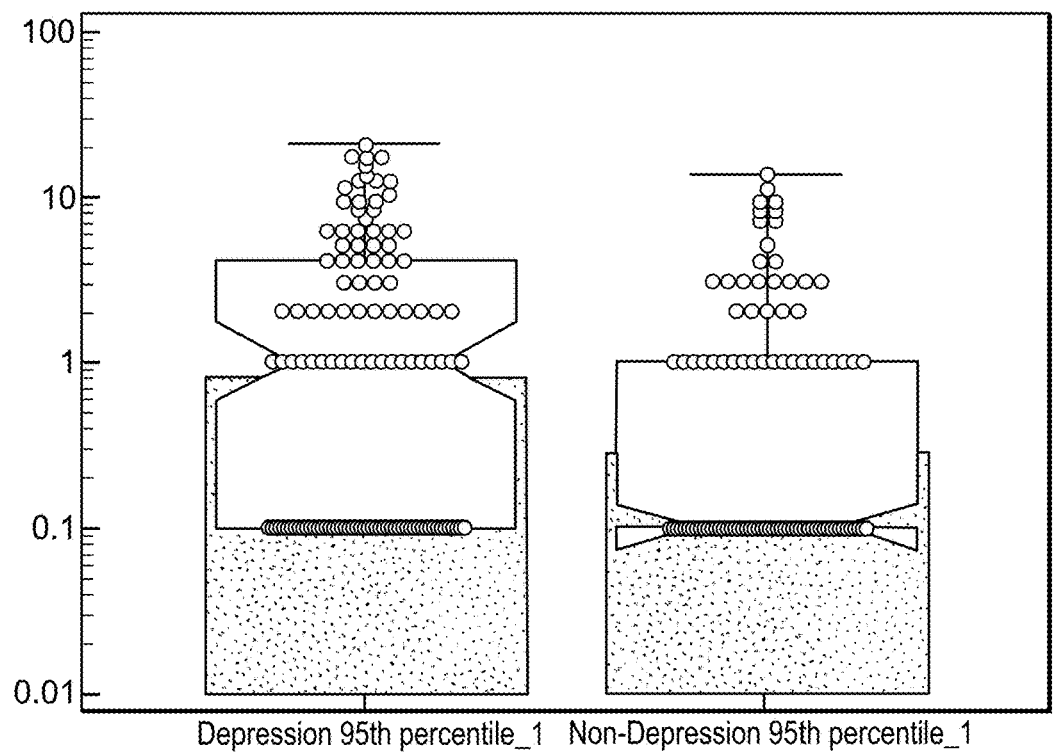

FIG. 6D illustrates a notched box and whisker plot of data shown in Table 5B.

Table 12A shows statistical data of a Receiver Operating Characteristic (ROC) curve analysis of data shown in Tables 5A-11A.

Table 12B shows statistical data of a Receiver Operating Characteristic (ROC) curve analysis of data shown in Tables 5B-11B.

FIG. 7A illustrates the ROC curve corresponding to the statistical data shown in Table 12A.

FIG. 7B illustrates the ROC curve corresponding to the statistical data shown in Table 12B.

Table 13A shows a statistical data of performance metrics in predicting Depression status among female patients from number of positive foods based on the 90$^{th}$ percentile.

Table 13B shows a statistical data of performance metrics in predicting Depression status among male patients from number of positive foods based on the 90$^{th}$ percentile.

Table 14A shows a statistical data of performance metrics in predicting Depression status among female patients from number of positive foods based on the 95$^{th}$ percentile.

Table 14B shows a statistical data of performance metrics in predicting Depression status among male patients from number of positive foods based on the 95$^{th}$ percentile.

DETAILED DESCRIPTION

The inventors have discovered that food preparations used in food tests to identify trigger foods in patients diagnosed with or suspected to have Depression are not equally well predictive and/or associated with Depression/Depression symptoms. Indeed, various experiments have revealed that among a wide variety of food items certain food items are highly predictive/associated with Depression whereas others have no statistically significant association with Depression.

Even more unexpectedly, the inventors discovered that in addition to the high variability of food items, gender variability with respect to response in a test plays a substantial role in the determination of association or a food item with Depression. Consequently, based on the inventors' findings and further contemplations, test kits and methods are now presented with substantially higher predictive power in the choice of food items that could be eliminated for reduction of Depression signs and symptoms.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In one aspect, the inventors therefore contemplate a test kit or test panel that is suitable for testing food intolerance in patients where the patient is diagnosed with or suspected to have Depression. Most preferably, such test kit or panel will include a plurality of distinct food preparations (e.g., raw or processed extract, preferably aqueous extract with optional co-solvent, which may or may not be filtered) that are coupled to individually addressable respective solid carriers (e.g., in a form of an array or a micro well plate), wherein the distinct food preparations have an average discriminatory p-value of ≤0.07 as determined by raw p-value or an average discriminatory p-value of ≤0.10 as determined by FDR multiplicity adjusted p-value.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

While not limiting to the inventive subject matter, food preparations will typically be drawn from foods generally known or suspected to trigger signs or symptoms of Depression. Particularly suitable food preparations may be identified by the experimental procedures outlined below. Thus, it should be appreciated that the food items need not be limited to the items described herein, but that all items are contemplated that can be identified by the methods presented herein. Therefore, exemplary food preparations include at least two, at least four, at least eight, or at least 12 food preparations prepared from foods 1-26 of Table 2. Still further especially contemplated food items and food additives from which food preparations can be prepared are listed in Table 1.

Using bodily fluids from patients diagnosed with or suspected to have Depression and healthy control group individuals (i.e., those not diagnosed with or not suspected to have Depression), numerous additional food items may be identified. Preferably, such identified food items will have high discriminatory power and as such have a p-value of ≤0.15, more preferably ≤0.10, and most preferably ≤0.05 as determined by raw p-value, and/or a p-value of ≤0.10, more preferably ≤0.08, and most preferably ≤0.07 as determined by False Discovery Rate (FDR) multiplicity adjusted p-value.

In certain embodiments, such identified food preparations will have high discriminatory power and, as such, will have a p-value of ≤0.15, ≤0.10, or even ≤0.05 as determined by raw p-value, and/or a p-value of ≤0.10, ≤0.08, or even ≤0.07 as determined by False Discovery Rate (FDR) multiplicity adjusted p-value.

Therefore, where a panel has multiple food preparations, it is contemplated that the plurality of distinct food preparations has an average discriminatory p-value of ≤0.05 as determined by raw p-value or an average discriminatory p-value of ≤0.08 as determined by FDR multiplicity adjusted p-value, or even more preferably an average discriminatory p-value of ≤0.025 as determined by raw p-value or an average discriminatory p-value of ≤0.07 as determined by FDR multiplicity adjusted p-value. In further preferred aspects, it should be appreciated that the FDR multiplicity adjusted p-value may be adjusted for at least one of age and gender, and most preferably adjusted for both age and gender. On the other hand, where a test kit or panel is stratified for use with a single gender, it is also contemplated that in a test kit or panel at least 50% (and more typically 70% or all) of the plurality of distinct food preparations, when adjusted for a single gender, have an average discriminatory p-value of ≤0.07 as determined by raw p-value or an average discriminatory p-value of ≤0.10 as determined by FDR multiplicity adjusted p-value. Furthermore, it should be appreciated that other stratifications (e.g., dietary preference, ethnicity, place of residence, genetic predisposition or family history, etc.) are also contemplated, and the person of ordinary skill in the art (PHOSITA) will be readily appraised of the appropriate choice of stratification.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Of course, it should be noted that the particular format of the test kit or panel may vary considerably and contemplated formats include micro well plates, dip sticks, membrane-bound arrays, etc. Consequently, the solid carrier to which the food preparations are coupled may include wells of a multiwell plate, a (e.g., color-coded or magnetic) bead, or an adsorptive film (e.g., nitrocellulose or micro/nanoporous polymeric film), or an electrical sensor, (e.g., a printed copper sensor or microchip).

Consequently, the inventors also contemplate a method of testing food intolerance in patients that are diagnosed with or suspected to have Depression. Most typically, such methods will include a step of contacting a food preparation with a bodily fluid (e.g., whole blood, plasma, serum, saliva, or a fecal suspension) of a patient that is diagnosed with or suspected to have Depression, and wherein the bodily fluid is associated with a gender identification. As noted before, the step of contacting is preferably performed under conditions that allow IgG (or IgE or IgA or IgM) from the bodily fluid to bind to at least one component of the food preparation, and the IgG bound to the component(s) of the food preparation are then quantified/measured to obtain a signal. In some embodiments, the signal is then compared against a gender-stratified reference value (e.g., at least a 90th percentile value) for the food preparation using the gender identification to obtain a result, which is then used to update or generate a report (e.g., written medical report; oral report of results from doctor to patient; written or oral directive from physician based on results).

In certain embodiments, such methods will not be limited to a single food preparation, but will employ multiple different food preparations. As noted before, suitable food preparations can be identified using various methods as described below, however, especially preferred food preparations include foods 1-26, of Table 2, and/or items of Table 1. As also noted above, it is generally preferred that at least some, or all of the different food preparations have an average discriminatory p-value of ≤0.07 (or ≤0.05, or ≤0.025) as determined by raw p-value, and/or an average discriminatory p-value of ≤0.10 (or ≤0.08, or ≤0.07) as determined by FDR multiplicity adjusted p-value.

While in certain embodiments food preparations are prepared from single food items as crude extracts, or crude filtered extracts, it is contemplated that food preparations can be prepared from mixtures of a plurality of food items (e.g., a mixture of citrus comprising lemon, orange, and a grapefruit, a mixture of yeast comprising baker's yeast and brewer's yeast, a mixture of rice comprising a brown rice and white rice, a mixture of sugars comprising honey, malt, and cane sugar). In some embodiments, it is also contemplated that food preparations can be prepared from purified food antigens or recombinant food antigens.

As it is generally preferred that the food preparation is immobilized on a solid surface (typically in an addressable manner), it is contemplated that the step of measuring the IgG or other type of antibody bound to the component of the food preparation is performed via an ELISA test. Exemplary solid surfaces include, but are not limited to, wells in a multiwell plate, such that each food preparation may be isolated to a separate microwell. In certain embodiments, the food preparation will be coupled to, or immobilized on, the solid surface. In other embodiments, the food preparation(s) will be coupled to a molecular tag that allows for binding to human immunoglobulins (e.g., IgG) in solution.

Viewed from a different perspective, the inventors also contemplate a method of generating a test for food intolerance in patients diagnosed with or suspected to have Depression. Because the test is applied to patients already diagnosed with or suspected to have Depression, the authors do not contemplate that the method has a diagnostic purpose. Instead, the method is for identifying triggering food items among already diagnosed or suspected Depression patients. Such test will typically include a step of obtaining one or more test results (e.g., ELISA) for various distinct food preparations, wherein the test results are based on bodily fluids (e.g., blood saliva, fecal suspension) of patients diagnosed with or suspected to have Depression and bodily fluids of a control group not diagnosed with or not suspected to have Depression. Most preferably, the test results are then stratified by gender for each of the distinct food preparations, a different cutoff value for male and female patients for each of the distinct food preparations (e.g., cutoff value for male and female patients has a difference of at least 10% (abs)) is assigned for a predetermined percentile rank (e.g., 90th or 95th percentile).

As noted earlier, and while not limiting to the inventive subject matter, it is contemplated that the distinct food preparations include at least two (or six, or ten, or 15) food preparations prepared from food items selected from the group consisting of foods 1-26 of Table 2, and/or items of Table 1. On the other hand, where new food items are tested, it should be appreciated that the distinct food preparations include a food preparation prepared from a food items other than foods 1-26 of Table 2. Regardless of the particular choice of food items, it is generally preferred however, that the distinct food preparations have an average discriminatory p-value of $\leq 0.07$ (or $\leq 0.05$, or $\leq 0.025$) as determined by raw p-value or an average discriminatory p-value of $\leq 0.10$ (or $\leq 0.08$, or $\leq 0.07$) as determined by FDR multiplicity adjusted p-value. Exemplary aspects and protocols, and considerations are provided in the experimental description below.

Thus, it should be appreciated that by having a high-confidence test system as described herein, the rate of false-positive and false negatives can be significantly reduced, and especially where the test systems and methods are gender stratified or adjusted for gender differences as shown below. Such advantages have heretofore not been realized and it is expected that the systems and methods presented herein will substantially increase the predictive power of food sensitivity tests for patients diagnosed with or suspected to have Depression.

Experiments

General Protocol for food preparation generation: Commercially available food extracts (available from Biomerica Inc., 17571 Von Karman Ave, Irvine, CA 92614) prepared from the edible portion of the respective raw foods were used to prepare ELISA plates following the manufacturer's instructions.

For some food extracts, the inventors expect that food extracts prepared with specific procedures to generate food extracts provides more superior results in detecting elevated IgG reactivity in Depression patients compared to commercially available food extracts. For example, for grains and nuts, a three-step procedure of generating food extracts is preferred. The first step is a defatting step. In this step, lipids from grains and nuts are extracted by contacting the flour of grains and nuts with a non-polar solvent and collecting residue. Then, the defatted grain or nut flour are extracted by contacting the flour with elevated pH to obtain a mixture and removing the solid from the mixture to obtain the liquid extract. Once the liquid extract is generated, the liquid extract is stabilized by adding an aqueous formulation. In a preferred embodiment, the aqueous formulation includes a sugar alcohol, a metal chelating agent, protease inhibitor, mineral salt, and buffer component 20-50 mM of buffer from 4-9 pH. This formulation allowed for long term storage at $-70°$ C. and multiple freeze-thaws without a loss of activity.

For another example, for meats and fish, a two step procedure of generating food extract is preferred. The first step is an extraction step. In this step, extracts from raw, uncooked meats or fish are generated by emulsifying the raw, uncooked meats or fish in an aqueous buffer formulation in a high impact pressure processor. Then, solid materials are removed to obtain liquid extract. Once the liquid extract is generated, the liquid extract is stabilized by adding an aqueous formulation. In a preferred embodiment, the aqueous formulation includes a sugar alcohol, a metal chelating agent, protease inhibitor, mineral salt, and buffer component 20-50 mM of buffer from 4-9 pH. This formulation allowed for long term storage at $-70°$ C. and multiple freeze-thaws without a loss of activity.

For still another example, for fruits and vegetables, a two step procedure of generating food extract is preferred. The first step is an extraction step. In this step, liquid extracts from fruits or vegetables are generated using an extractor (e.g., masticating juicer, etc) to pulverize foods and extract juice. Then, solid materials are removed to obtain liquid extract. Once the liquid extract is generated, the liquid extract is stabilized by adding an aqueous formulation. In a preferred embodiment, the aqueous formulation includes a sugar alcohol, a metal chelating agent, protease inhibitor, mineral salt, and buffer component 20-50 mM of buffer from 4-9 pH. This formulation allowed for long term storage at $-70°$ C. and multiple freeze-thaws without a loss of activity.

Blocking of ELISA plates: To optimize signal to noise, plates will be blocked with a proprietary blocking buffer. In a preferred embodiment, the blocking buffer includes 20-50 mM of buffer from 4-9 pH, a protein of animal origin and a short chain alcohol. Other blocking buffers, including several commercial preparations, can be attempted but may not provide adequate signal to noise and low assay variability required.

ELISA preparation and sample testing: Food antigen preparations were immobilized onto respective microtiter wells following the manufacturer's instructions. For the assays, the food antigens were allowed to react with antibodies present in the patients' serum, and excess serum proteins were removed by a wash step. For detection of IgG antibody binding, enzyme labeled anti-IgG antibody conjugate was allowed to react with antigen-antibody complex. A color was developed by the addition of a substrate that reacts with the coupled enzyme. The color intensity was measured and is directly proportional to the concentration of IgG antibody specific to a particular food antigen.

Methodology to determine ranked food list in order of ability of ELISA signals to distinguish Depression from control subjects: Out of an initial selection (e.g., 100 food items, or 150 food items, or even more), samples can be eliminated prior to analysis due to low consumption in an intended population. In addition, specific food items can be used as being representative of the a larger more generic food group, especially where prior testing has established a correlation among different species within a generic group (most preferably in both genders, but also suitable for correlation for a single gender). For example, green pepper could be dropped in favor of chili pepper as representative of the "pepper" food group, or sweet potato could be dropped in favor of potato as representative of the "potato" food group. In further preferred aspects, the final list foods will be shorter than 50 food items, and more preferably equal or less than of 40 food items.

Since the foods ultimately selected for the food intolerance panel will not be specific for a particular gender, a gender-neutral food list is necessary. Since the observed sample will be at least initially imbalanced by gender (e.g., Controls: 38.6% female, Depression: 74.3% female), differences in ELISA signal magnitude strictly due to gender will be removed by modeling signal scores against gender using a two-sample t-test and storing the residuals for further analysis. For each of the tested foods, residual signal scores will be compared between Depression and controls using a permutation test on a two-sample t-test with a relative high number of resamplings (e.g., >1,000, more preferably >10,000, even more preferably >50,000). The Satterthwaite approximation can then be used for the denominator degrees of freedom to account for lack of homogeneity of variances, and the 2-tailed permuted p-value will represent the raw p-value for each food. False Discovery Rates (FDR) among the comparisons, will be adjusted by any acceptable statistical procedures (e.g., Benjamin-Hochberg, Family-wise Error Rate (FWER), Per Comparison Error Rate (PCER), etc.).

Foods were then ranked according to their 2-tailed FDR multiplicity-adjusted p-values. Foods with adjusted p-values equal to or lower than the desired FDR threshold are deemed to have significantly higher signal scores among Depression than control subjects and therefore deemed candidates for inclusion into a food intolerance panel. A typical result that is representative of the outcome of the statistical procedure is provided in Table 2. Here the ranking of foods is according to 2-tailed permutation T-test p-values with FDR adjustment.

Based on earlier experiments (data not shown here, see U.S. 62/359,909), the inventors contemplate that even for the same food preparation tested, the ELISA score for at least several food items will vary dramatically, and exemplary raw data are provided in Table 3. As should be readily appreciated, data unstratified by gender will therefore lose significant explanatory power where the same cutoff value is applied to raw data for male and female data. To overcome such disadvantage, the inventors therefore contemplate stratification of the data by gender as described below.

Statistical Method for Cutpoint Selection for each Food: The determination of what ELISA signal scores would constitute a "positive" response can be made by summarizing the distribution of signal scores among the Control subjects. For each food, Depression subjects who have observed scores greater than or equal to selected quantiles of the Control subject distribution will be deemed "positive". To attenuate the influence of any one subject on cutpoint determination, each food-specific and gender-specific dataset will be bootstrap resampled 1000 times. Within each bootstrap replicate, the 90th and 95th percentiles of the Control signal scores will be determined. Each Depression subject in the bootstrap sample will be compared to the 90th and 95% percentiles to determine whether he/she had a "positive" response. The final 90th and 95th percentile-based cutpoints for each food and gender will be computed as the average 90th and 95th percentiles across the 1000 samples. The number of foods for which each Depression subject will be rated as "positive" was computed by pooling data across foods. Using such method, the inventors will be now able to identify cutoff values for a predetermined percentile rank that in most cases was substantially different as can be taken from Table 4.

Typical examples for the gender difference in IgG response in blood with respect to almond is shown in FIGS. 1A-1D, where FIG. 1A shows the signal distribution in men along with the $95^{th}$ percentile cutoff as determined from the male control population. FIG. 1B shows the distribution of percentage of male Depression subjects exceeding the $90^{th}$ and $95^{th}$ percentile, while FIG. 1C shows the signal distribution in women along with the $95^{th}$ percentile cutoff as determined from the female control population. FIG. 1D shows the distribution of percentage of female Depression subjects exceeding the $90^{th}$ and $95^{th}$ percentile. In the same fashion, FIGS. 2A-2D exemplarily depict the differential response to tomato, FIGS. 3A-3D exemplarily depict the differential response to tobacco, and FIGS. 4A-4D exemplarily depict the differential response to carrot. FIGS. 5A-5B show the distribution of Depression subjects by number of foods that were identified as trigger foods at the $90^{th}$ percentile (5A) and $95^{th}$ percentile (5B). Inventors contemplate that regardless of the particular food items, male and female responses will be notably distinct.

It should be noted that nothing in the art have provided any predictable food groups related to Depression that is gender-stratified. Thus, a discovery of food items that show distinct responses by gender is a surprising result, which could not be obviously expected in view of all previously available arts. In other words, selection of food items based on gender stratification provides an unexpected technical effect such that statistical significances for particular food items as triggering food among male or female Depression patients have been significantly improved.

Normalization of IgG Response Data: While the raw data of the patient's IgG response results can be used to compare strength of response among given foods, it is also contemplated that the IgG response results of a patient are normalized and indexed to generate unit-less numbers for comparison of relative strength of response to a given food. For example, one or more of a patient's food specific IgG results (e.g., IgG specific to orange and IgG specific to malt) can be normalized to the patient's total IgG. The normalized value of the patient's IgG specific to orange can be 0.1 and the normalized value of the patient's IgG specific to malt can be 0.3. In this scenario, the relative strength of the patient's response to malt is three times higher compared to orange. Then, the patient's sensitivity to malt and orange can be indexed as such.

In other examples, one or more of a patient's food specific IgG results (e.g., IgG specific to shrimp and IgG specific to pork) can be normalized to the global mean of that patient's food specific IgG results. The global means of the patient's food specific IgG can be measured by total amount of the patient's food specific IgG. In this scenario, the patient's specific IgG to shrimp can be normalized to the mean of patient's total food specific IgG (e.g., mean of IgG levels to shrimp, pork, Dungeness crab, chicken, peas, etc.). However, it is also contemplated that the global means of the patient's food specific IgG can be measured by the patient's IgG levels to a specific type of food via multiple tests. If the patient has been tested for his sensitivity to shrimp five times and to pork seven times previously, the patient's new IgG values to shrimp or to pork are normalized to the mean of five-times test results to shrimp or the mean of seven-times test results to pork. The normalized value of the patient's IgG specific to shrimp can be 6.0 and the normalized value of the patient's IgG specific to pork can be 1.0. In this scenario, the patient has six times higher sensitivity to shrimp at this time compared to his average sensitivity to shrimp, but substantially similar sensitivity to pork. Then, the patient's sensitivity to shrimp and pork can be indexed based on such comparison.

Methodology to determine the subset of Depression patients with food sensitivities that underlie Depression: While it is suspected that food sensitivities plays a substantial role in signs and symptoms of Depression, some Depression patients may not have food sensitivities that underlie Depression. Those patients would not be benefit from dietary intervention to treat signs and symptoms of Depression. To determine the subset of such patients, body fluid samples of Depression patients and non-Depression patients can be tested with ELISA test using test devices with up to 26 food samples.

Table 5A and Table 5B provide exemplary raw data. As should be readily appreciated, the data indicate number of positive results out of 26 sample foods based on $90^{th}$ percentile value (Table 5A) or $95^{th}$ percentile value (Table 5B). The first column is Depression (n=114); second column is non-Depression (n=132) by ICD-10 code. Average and median number of positive foods was computed for Depression and non-Depression patients. From the raw data shown in Table 5A and Table 5B, average and standard deviation of the number of positive foods was computed for Depression and non-Depression patients. Additionally, the number and percentage of patients with zero positive foods was calculated for both Depression and non-Depression. The number and percentage of patients with zero positive foods in the Depression population is approximately 50% lower than the percentage of patients with zero positive foods in the non-Depression population (27.2% vs. 51.5%, respectively) based on $90^{th}$ percentile value (Table 5A), and the percentage of patients in the Depression population with zero positive foods is also significantly lower (i.e. approximately 40% lower) than that seen in the non-Depression population (39.5% vs. 66.7%, respectively) based on $95^{th}$ percentile value (Table 5B). Thus, it can be easily appreciated that the Depression patient having sensitivity to zero positive foods is unlikely to have food sensitivities underlying their signs and symptoms of Depression.

Table 6A and Table 7A show exemplary statistical data summarizing the raw data of two patient populations shown in Table 5A. The statistical data includes normality, arithmetic mean, median, percentiles and 95% confidence interval (CI) for the mean and median representing number of positive foods in the Depression population and the non-Depression population. Table 6B and Table 7B show exemplary statistical data summarizing the raw data of two patient populations shown in Table 5B. The statistical data includes normality, arithmetic mean, median, percentiles and 95% confidence interval (CI) for the mean and median representing number of positive foods in the Depression population and the non-Depression population.

Table 8A and Table 9A show exemplary statistical data summarizing the raw data of two patient populations shown in Table 5A. In Tables 8A and 9A, the raw data was transformed by logarithmic transformation to improve the data interpretation. Table 8B and Table 9B show another exemplary statistical data summarizing the raw data of two patient populations shown in Table 5B. In Tables 8B and 9B, the raw data was transformed by logarithmic transformation to improve the data interpretation.

Table 10A and Table 11A show exemplary statistical data of an independent T-test (Table 10A, logarithmically transformed data) and a Mann-Whitney test (Table 11A) to compare the geometric mean number of positive foods between the Depression and non-Depression samples. The data shown in Table 10A and Table 11A indicate statistically significant differences in the geometric mean of positive number of foods between the Depression population and the non-Depression population. In both statistical tests, it is shown that the number of positive responses with 26 food samples is significantly higher in the Depression population than in the non-Depression population with an average discriminatory p-value of ≤0.0001. These statistical data is also illustrated as a box and whisker plot in FIG. 6A, and a notched box and whisker plot in FIG. 6B.

Table 10B and Table 11B show exemplary statistical data of an independent T-test (Table 10A, logarithmically transformed data) and a Mann-Whitney test (Table 11B) to compare the geometric mean number of positive foods between the Depression and non-Depression samples. The data shown in Table 10B and Table 11B indicate statistically significant differences in the geometric mean of positive number of foods between the Depression population and the non-Depression population. In both statistical tests, it is shown that the number of positive responses with 26 food samples is significantly higher in the Depression population than in the non-Depression population with an average discriminatory p-value of ≤0.0001. These statistical data is also illustrated as a box and whisker plot in FIG. 6C, and a notched box and whisker plot in FIG. 6D.

Table 12A shows exemplary statistical data of a Receiver Operating Characteristic (ROC) curve analysis of data shown in Tables 5A-11A to determine the diagnostic power of the test used in Table 5 at discriminating Depression from non-Depression subjects. When a cutoff criterion of more than 4 positive foods is used, the test yields a data with 36.8% sensitivity and 87.8% specificity, with an area under the curve (AUROC) of 0.665. The p-value for the ROC is significant at a p-value of <0.0001. FIG. 7A illustrates the ROC curve corresponding to the statistical data shown in Table 12A. Because the statistical difference between the Depression population and the non-Depression population is significant when the test results are cut off to a positive number of 4, the number of foods for which a patient tests positive could be used as a confirmation of the primary clinical diagnosis of Depression, and whether it is likely that food sensitivities underlies on the patient's signs and symptoms of Depression. Therefore, the above test can be used as another 'rule in' test to add to currently available clinical criteria for diagnosis for Depression.

As shown in Tables 5A-12A, and FIG. 7A, based on $90^{th}$ percentile data, the number of positive foods seen in Depression vs. non-Depression subjects is significantly different whether the geometric mean or median of the data is compared. The number of positive foods that a person has is indicative of the presence of Depression in subjects. The test has discriminatory power to detect Depression with 36.8% sensitivity and 87.8% specificity. Additionally, the absolute number and percentage of subjects with 0 positive foods is also very different in Depression vs. non-Depression subjects, with a far lower percentage of Depression subjects (27.2%) having 0 positive foods than non-Depression subjects (51.5%). The data suggests a subset of Depression patients may have Depression due to other factors than diet, and may not benefit from dietary restriction.

Table 12B shows exemplary statistical data of a Receiver Operating Characteristic (ROC) curve analysis of data shown in Tables 5B-11B to determine the diagnostic power of the test used in Table 5 at discriminating Depression from non-Depression subjects. When a cutoff criterion of more than 0 positive foods is used, the test yields a data with 60.5% sensitivity and 66.7% specificity, with an area under the curve (AUROC) of 0.659. The p-value for the ROC is significant at a p-value of <0.0001. FIG. 7B illustrates the ROC curve corresponding to the statistical data shown in Table 12B. Because the statistical difference between the Depression population and the non-Depression population is significant when the test results are cut off to positive number of >0, the number of foods that a patient tests positive could be used as a confirmation of the primary clinical diagnosis of Depression, and whether it is likely that food sensitivities underlies on the patient's signs and symptoms of Depression. Therefore, the above test can be used as another 'rule in' test to add to currently available clinical criteria for diagnosis for Depression.

As shown in Tables 5B-12B, and FIG. 7B, based on $95^{th}$ percentile data, the number of positive foods seen in Depression vs. non-Depression subjects is significantly different whether the geometric mean or median of the data is compared. The number of positive foods that a person has is indicative of the presence of Depression in subjects. The test has discriminatory power to detect Depression with 60.5% sensitivity and 66.7% specificity. Additionally, the absolute number and percentage of subjects with 0 positive foods is also very different in Depression vs. non-Depression subjects, with a far lower percentage of Depression subjects (39.5%) having 0 positive foods than non-Depression subjects (66.7%). The data suggests a subset of Depression patients may have Depression due to other factors than diet, and may not benefit from dietary restriction.

Method for determining distribution of per-person number of foods declared "positive": To determine the distribution of number of "positive" foods per person and measure the diagnostic performance, the analysis will be performed with 26 food items from Table 2, which shows most positive responses to Depression patients. To attenuate the influence of any one subject on this analysis, each food-specific and gender-specific dataset will be bootstrap resampled 1000 times. Then, for each food item in the bootstrap sample, sex-specific cutpoint will be determined using the 90th and 95th percentiles of the control population. Once the sex-specific cutpoints are determined, the sex-specific cutpoints will be compared with the observed ELISA signal scores for both control and Depression subjects. In this comparison, if the observed signal is equal or more than the cutpoint value, then it will be determined "positive" food, and if the observed signal is less than the cutpoint value, then it will be determined "negative" food.

Once all food items were determined either positive or negative, the results of the 52 (26 foods×2 cutpoints) calls for each subject will be saved within each bootstrap replicate. Then, for each subject, 26 calls will be summed using $90^{th}$ percentile as cutpoint to get "Number of Positive Foods $(90^{th})$," and the rest of 26 calls will be summed using $95^{th}$ percentile to get "Number of Positive Foods $(95^{th})$." Then, within each replicate, "Number of Positive Foods $(90^{th})$" and "Number of Positive Foods $(95^{th})$" will be summarized across subjects to get descriptive statistics for each replicate as follows: 1) overall means equals to the mean of means, 2) overall standard deviation equals to the mean of standard deviations, 3) overall medial equals to the mean of medians, 4) overall minimum equals to the minimum of minimums, and 5) overall maximum equals to maximum of maximum. In this analysis, to avoid non-integer "Number of Positive Foods" when computing frequency distribution and histogram, the authors will pretend that the 1000 repetitions of the same original dataset were actually 999 sets of new subjects of the same size added to the original sample. Once the summarization of data is done, frequency distributions and histograms will be generated for both "Number of Positive Foods $(90^{th})$" and "Number of Positive Foods $(95^{th})$" for both genders and for both Depression subjects and control subjects using programs "a_pos_foods.sas, a_pos_foods_by_dx.sas".

Method for measuring diagnostic performance: To measure diagnostic performance for each food items for each subject, we will use data of "Number of Positive Foods $(90^{th})$" and "Number of Positive Foods $(95^{th})$" for each subject within each bootstrap replicate described above. In this analysis, the cutpoint was set to 1. Thus, if a subject has one or more "Number of Positive Foods $(90^{th})$", then the subject will be called "Has Depression." If a subject has less than one "Number of Positive Foods $(90^{th})$", then the subject will be called "Does Not Have Depression." When all calls were made, the calls were compared with actual diagnosis to determine whether a call was a True Positive (TP), True Negative (TN), False Positive (FP), or False Negative (FN). The comparisons will be summarized across subjects to get the performance metrics of sensitivity, specificity, positive predictive value, and negative predictive value for both "Number of Positive Foods $(90^{th})$" and "Number of Positive Foods $(95^{th})$" when the cutpoint is set to 1 for each method. Each (sensitivity, 1-specificity) pair becomes a point on the ROC curve for this replicate.

To increase the accuracy, the analysis above will be repeated by incrementing cutpoint from 2 up to 26, and repeated for each of the 1000 bootstrap replicates. Then the performance metrics across the 1000 bootstrap replicates will be summarized by calculating averages using a program "t_pos_foods_by_dx.sas". The results of diagnostic performance for female and male are shown in Tables 13A and 13B (90th percentile) and Tables 14A and 14B (95th percentile).

Of course, it should be appreciated that certain variations in the food preparations may be made without altering the inventive subject matter presented herein. For example, where the food item was yellow onion, that item should be understood to also include other onion varieties that were demonstrated to have equivalent activity in the tests. Indeed, the inventors have noted that for each tested food preparation, certain other related food preparations also tested in the same or equivalent manner (data not shown). Thus, it should be appreciated that each tested and claimed food preparation will have equivalent related preparations with demonstrated equal or equivalent reactions in the test.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

TABLE 1

Abalone
Adlay
Almond
American Cheese
Apple
Artichoke
Asparagus
Avocado
Baby Bok Choy
Bamboo shoots
Banana
Barley, whole grain
Beef
Beets
Beta-lactoglobulin
Blueberry
Broccoli
Buckwheat
Butter
Cabbage
Cane sugar
Cantaloupe
Caraway
Carrot
Casein
Cashew
Cauliflower
Celery
Chard
Cheddar Cheese
Chick Peas
Chicken
Chili pepper
Chocolate
Cinnamon
Clam
Cocoa Bean
Coconut
Codfish
Coffee
Cola nut
Corn
Cottage cheese
Cow's milk
Crab
Cucumber
Cured Cheese
Cuttlefish
Duck
Durian
Eel
Egg White (separate)
Egg Yolk (separate)
Egg, white/yolk (comb.)
Eggplant
Garlic
Ginger
Gluten - Gliadin
Goat's milk
Grape, white/concord
Grapefruit
Grass Carp
Green Onion
Green pea
Green pepper
Guava
Hair Tail
Hake
Halibut
Hazelnut
Honey
Kelp
Kidney bean
Kiwi Fruit
Lamb TABLE 1-continued Leek
Lemon
Lentils
Lettuce, Iceberg
Lima bean
Lobster
Longan
Mackerel
Malt
Mango
Marjoram
Millet
Mung bean
Mushroom
Mustard seed
Oat
Olive
Onion
Orange
Oyster
Papaya
Paprika
Parsley
Peach
Peanut
Pear
Pepper, Black
Pineapple
Pinto bean
Plum
Pork
Potato
Rabbit
Rice
Roquefort Cheese
Rye
Saccharine
Safflower seed
Salmon
Sardine
Scallop
Sesame
Shark fin
Sheep's milk
Shrimp
Sole
Soybean
Spinach
Squashes
Squid
Strawberry
String bean
Sunflower seed
Sweet potato
Swiss cheese
Taro
Tea, black
Tobacco
Tomato
Trout
Tuna
Turkey
Vanilla
Walnut, black
Watermelon
Welch Onion
Wheat
Wheat bran
Yeast (*S. cerevisiae*)
Yogurt

FOOD ADDITIVES

Arabic Gum
Carboxymethyl Cellulose
Carrageneenan
FD&C Blue #1
FD&C Red #3
FD&C Red #40
FD&C Yellow #5
FD&C Yellow #6

TABLE 1-continued

Gelatin
Guar Gum
Maltodextrin
Pectin
Whey
Xanthan Gum

TABLE 2

Ranking of Foods according to 2-tailed Permutation T-test p-values with FDR adjustment

| Rank | Food | Raw p-value | FDR Multiplicity-adj p-value |
|---|---|---|---|
| 1 | Almond | 0.0001 | 0.0080 |
| 2 | Tomato | 0.0002 | 0.0080 |
| 3 | Tobacco | 0.0006 | 0.0166 |
| 4 | Carrot | 0.0010 | 0.0185 |
| 5 | Orange | 0.0010 | 0.0185 |
| 6 | Cucumber | 0.0017 | 0.0252 |
| 7 | Broccoli | 0.0028 | 0.0323 |
| 8 | Lettuce | 0.0029 | 0.0323 |
| 9 | Malt | 0.0034 | 0.0340 |
| 10 | Cantaloupe | 0.0044 | 0.0390 |
| 11 | Corn | 0.0048 | 0.0390 |
| 12 | Wheat | 0.0066 | 0.0449 |
| 13 | Honey | 0.0069 | 0.0449 |
| 14 | Chocolate | 0.0071 | 0.0449 |
| 15 | Oat | 0.0101 | 0.0567 |
| 16 | Avocado | 0.0102 | 0.0567 |
| 17 | Rye | 0.0119 | 0.0602 |
| 18 | Strawberry | 0.0122 | 0.0602 |
| 19 | Cauliflower | 0.0130 | 0.0606 |
| 20 | Safflower | 0.0136 | 0.0606 |
| 21 | Tea | 0.0151 | 0.0630 |
| 22 | Banana | 0.0156 | 0.0630 |
| 23 | Squashes | 0.0184 | 0.0710 |
| 24 | Green_Pepper | 0.0213 | 0.0790 |
| 25 | Butter | 0.0237 | 0.0842 |
| 26 | Buck_Wheat | 0.0258 | 0.0885 |
| 27 | Rice | 0.0307 | 0.1013 |
| 28 | Soybean | 0.0363 | 0.1118 |
| 29 | Grapefruit | 0.0364 | 0.1118 |
| 30 | Oyster | 0.0427 | 0.1266 |
| 31 | Yeast_Brewer | 0.0473 | 0.1359 |
| 32 | Peach | 0.0569 | 0.1584 |
| 33 | Cane_Sugar | 0.0594 | 0.1603 |
| 34 | Cow_Milk | 0.0616 | 0.1613 |
| 35 | Spinach | 0.0667 | 0.1697 |
| 36 | Mustard | 0.0719 | 0.1779 |
| 37 | Cinnamon | 0.0800 | 0.1923 |
| 38 | Eggplant | 0.0854 | 0.2001 |
| 39 | Cabbage | 0.1034 | 0.2303 |
| 40 | Pinto_Bean | 0.1053 | 0.2303 |
| 41 | Onion | 0.1061 | 0.2303 |
| 42 | Sunflower_Sd | 0.1204 | 0.2552 |
| 43 | Walnut_Blk | 0.1233 | 0.2552 |
| 44 | Blueberry | 0.1312 | 0.2655 |
| 45 | Cottage_Ch_ | 0.1398 | 0.2714 |
| 46 | Cheddar_Ch_ | 0.1403 | 0.2714 |
| 47 | Goat_Milk | 0.1438 | 0.2715 |
| 48 | Lemon | 0.1464 | 0.2715 |
| 49 | Apple | 0.1891 | 0.3435 |
| 50 | Olive | 0.1965 | 0.3498 |
| 51 | Garlic | 0.2065 | 0.3604 |
| 52 | Yeast_Baker | 0.2187 | 0.3742 |
| 53 | Parsley | 0.2262 | 0.3798 |
| 54 | Sweet_Pot_ | 0.2585 | 0.4231 |
| 55 | Yogurt | 0.2615 | 0.4231 |
| 56 | Swiss_Ch_ | 0.2712 | 0.4311 |
| 57 | Amer_Cheese | 0.2839 | 0.4394 |
| 58 | Beef | 0.2873 | 0.4394 |
| 59 | Barley | 0.2934 | 0.4394 |
| 60 | Clam | 0.2962 | 0.4394 |
| 61 | Green_Pea | 0.3118 | 0.4550 |
| 62 | Salmon | 0.3239 | 0.4649 |
| 63 | Scallop | 0.3518 | 0.4969 |
| 64 | Celery | 0.3573 | 0.4969 |
| 65 | Chicken | 0.4077 | 0.5582 |
| 66 | Sardine | 0.4479 | 0.5963 |
| 67 | Lima_Bean | 0.4489 | 0.5963 |
| 68 | Codfish | 0.4567 | 0.5977 |
| 69 | Cashew | 0.4784 | 0.6171 |
| 70 | Peanut | 0.5032 | 0.6384 |
| 71 | Potato | 0.5093 | 0.6384 |
| 72 | Millet | 0.5283 | 0.6530 |
| 73 | Turkey | 0.5557 | 0.6775 |
| 74 | Pork | 0.5674 | 0.6820 |
| 75 | Mushroom | 0.5748 | 0.6820 |
| 76 | Coffee | 0.6105 | 0.7150 |
| 77 | Trout | 0.6332 | 0.7319 |
| 78 | Crab | 0.6492 | 0.7407 |
| 79 | Pineapple | 0.6858 | 0.7726 |
| 80 | Lobster | 0.7421 | 0.8256 |
| 81 | Egg | 0.7893 | 0.8673 |
| 82 | Sesame | 0.8279 | 0.8886 |
| 83 | Sole | 0.8314 | 0.8886 |
| 84 | Tuna | 0.8387 | 0.8886 |
| 85 | Halibut | 0.8863 | 0.9280 |
| 86 | String_Bean | 0.9103 | 0.9421 |
| 87 | Cola_Nut | 0.9604 | 0.9739 |
| 88 | Chili_Pepper | 0.9629 | 0.9739 |
| 89 | Grape | 0.9849 | 0.9849 |

TABLE 3

Basic Descriptive Statistics of ELISA Score by Food and Gender Comparing Depression to Control

| Sex | Food | Diagnosis | N | ELISA Score Mean | SD | Min | Max |
|---|---|---|---|---|---|---|---|
| FEMALE | Almond | Control | 51 | 4.057 | 1.630 | 1.275 | 8.090 |
| | | Depression | 84 | 6.053 | 5.372 | 1.210 | 33.082 |
| | | Diff (1-2) | — | −1.996 | 4.360 | — | — |
| | Amer_Cheese | Control | 51 | 32.961 | 66.654 | 0.100 | 400.00 |
| | | Depression | 84 | 31.594 | 42.040 | 1.002 | 244.77 |
| | | Diff (1-2) | — | 1.367 | 52.660 | — | — |
| | Apple | Control | 51 | 4.793 | 6.600 | 0.100 | 44.163 |
| | | Depression | 84 | 4.700 | 5.000 | 0.288 | 29.157 |
| | | Diff (1-2) | — | 0.093 | 5.655 | — | — |

TABLE 3-continued

Basic Descriptive Statistics of ELISA Score by Food and Gender
Comparing Depression to Control

| Sex | Food | Diagnosis | N | ELISA Score | | | |
|---|---|---|---|---|---|---|---|
| | | | | Mean | SD | Min | Max |
| | Avocado | Control | 51 | 2.144 | 1.129 | 0.100 | 5.561 |
| | | Depression | 84 | 3.734 | 6.321 | 0.099 | 43.891 |
| | | Diff (1-2) | — | −1.589 | 5.041 | — | — |
| | Banana | Control | 51 | 3.042 | 2.909 | 0.100 | 17.212 |
| | | Depression | 84 | 4.254 | 3.270 | 0.605 | 21.544 |
| | | Diff (1-2) | — | −1.212 | 3.139 | — | — |
| | Barley | Control | 51 | 3.867 | 3.919 | 0.100 | 25.110 |
| | | Depression | 84 | 9.751 | 27.814 | 0.504 | 227.10 |
| | | Diff (1-2) | — | −5.883 | 22.103 | — | — |
| | Beef | Control | 51 | 9.007 | 12.047 | 1.029 | 81.664 |
| | | Depression | 84 | 10.130 | 15.645 | 2.337 | 114.56 |
| | | Diff (1-2) | — | −1.124 | 14.398 | — | — |
| | Blueberry | Control | 51 | 3.533 | 4.712 | 0.100 | 26.459 |
| | | Depression | 84 | 3.925 | 2.782 | 0.706 | 17.918 |
| | | Diff (1-2) | — | −0.392 | 3.630 | — | — |
| | Broccoli | Control | 51 | 5.211 | 4.424 | 0.107 | 29.602 |
| | | Depression | 84 | 7.516 | 3.766 | 1.311 | 26.282 |
| | | Diff (1-2) | — | −2.305 | 4.026 | — | — |
| | Buck_Wheat | Control | 51 | 5.151 | 4.281 | 0.100 | 26.453 |
| | | Depression | 84 | 6.040 | 6.662 | 1.543 | 51.255 |
| | | Diff (1-2) | — | −0.890 | 5.881 | — | — |
| | Butter | Control | 51 | 17.809 | 24.981 | 0.100 | 150.93 |
| | | Depression | 84 | 19.850 | 26.939 | 1.776 | 169.07 |
| | | Diff (1-2) | — | −2.041 | 26.220 | — | — |
| | Cabbage | Control | 51 | 5.038 | 6.005 | 0.346 | 37.840 |
| | | Depression | 84 | 5.930 | 5.330 | 0.706 | 28.026 |
| | | Diff (1-2) | — | −0.892 | 5.593 | — | — |
| | Cane_Sugar | Control | 51 | 15.189 | 10.152 | 3.462 | 50.454 |
| | | Depression | 84 | 25.216 | 32.661 | 4.615 | 273.09 |
| | | Diff (1-2) | — | −10.027 | 26.542 | — | — |
| | Cantaloupe | Control | 51 | 4.707 | 2.368 | 1.153 | 12.761 |
| | | Depression | 84 | 6.464 | 6.047 | 1.506 | 39.659 |
| | | Diff (1-2) | — | −1.757 | 4.993 | — | — |
| | Carrot | Control | 51 | 2.702 | 1.549 | 0.100 | 6.945 |
| | | Depression | 84 | 4.670 | 4.958 | 0.706 | 33.323 |
| | | Diff (1-2) | — | −1.968 | 4.030 | — | — |
| | Cashew | Control | 51 | 8.621 | 13.756 | 0.100 | 81.886 |
| | | Depression | 84 | 13.003 | 44.243 | 0.504 | 400.00 |
| | | Diff (1-2) | — | −4.382 | 35.954 | — | — |
| | Cauliflower | Control | 51 | 4.203 | 2.424 | 0.427 | 11.768 |
| | | Depression | 84 | 5.122 | 4.128 | 1.109 | 31.116 |
| | | Diff (1-2) | — | −0.920 | 3.583 | — | — |
| | Celery | Control | 51 | 7.815 | 5.561 | 2.058 | 32.827 |
| | | Depression | 84 | 7.848 | 6.159 | 1.923 | 37.247 |
| | | Diff (1-2) | — | −0.034 | 5.941 | — | — |
| | Cheddar_Ch_ | Control | 51 | 25.261 | 59.385 | 1.533 | 400.00 |
| | | Depression | 84 | 25.785 | 46.652 | 0.992 | 271.88 |
| | | Diff (1-2) | — | −0.524 | 51.807 | — | — |
| | Chicken | Control | 51 | 14.077 | 8.350 | 2.690 | 50.000 |
| | | Depression | 84 | 16.733 | 25.109 | 2.054 | 164.81 |
| | | Diff (1-2) | — | −2.655 | 20.485 | — | — |
| | Chili_Pepper | Control | 51 | 7.281 | 6.348 | 0.571 | 32.357 |
| | | Depression | 84 | 6.294 | 5.445 | 1.326 | 43.789 |
| | | Diff (1-2) | — | 0.987 | 5.801 | — | — |
| | Chocolate | Control | 51 | 13.516 | 6.136 | 3.405 | 30.536 |
| | | Depression | 84 | 17.719 | 9.932 | 4.135 | 47.953 |
| | | Diff (1-2) | — | −4.203 | 8.701 | — | — |
| | Cinnamon | Control | 51 | 8.317 | 6.347 | 1.490 | 38.804 |
| | | Depression | 84 | 10.753 | 11.058 | 1.169 | 89.952 |
| | | Diff (1-2) | — | −2.436 | 9.563 | — | — |
| | Clam | Control | 51 | 36.890 | 57.603 | 7.452 | 400.00 |
| | | Depression | 84 | 26.931 | 27.003 | 4.547 | 171.60 |
| | | Diff (1-2) | — | 9.960 | 41.261 | — | — |
| | Codfish | Control | 51 | 27.484 | 34.270 | 6.174 | 203.91 |
| | | Depression | 84 | 24.346 | 32.188 | 3.328 | 232.15 |
| | | Diff (1-2) | — | 3.137 | 32.986 | — | — |
| | Coffee | Control | 51 | 34.003 | 55.076 | 6.732 | 400.00 |
| | | Depression | 84 | 28.989 | 44.549 | 3.065 | 312.78 |
| | | Diff (1-2) | — | 5.014 | 48.774 | — | — |
| | Cola_Nut | Control | 51 | 11.928 | 5.390 | 2.629 | 27.263 |
| | | Depression | 84 | 12.964 | 6.626 | 2.521 | 37.735 |
| | | Diff (1-2) | — | −1.035 | 6.190 | — | — |

TABLE 3-continued

Basic Descriptive Statistics of ELISA Score by Food and Gender
Comparing Depression to Control

| Sex | Food | Diagnosis | N | ELISA Score | | | |
| --- | --- | --- | --- | --- | --- | --- | --- |
| | | | | Mean | SD | Min | Max |
| | Corn | Control | 51 | 7.351 | 5.170 | 2.076 | 27.010 |
| | | Depression | 84 | 10.825 | 11.201 | 1.614 | 71.435 |
| | | Diff (1-2) | — | -3.474 | 9.399 | — | — |
| | Cottage_Ch_ | Control | 51 | 83.139 | 107.442 | 2.115 | 400.00 |
| | | Depression | 84 | 87.213 | 117.081 | 3.341 | 400.00 |
| | | Diff (1-2) | — | -4.074 | 113.554 | — | — |
| | Cow_Milk | Control | 51 | 65.188 | 90.937 | 1.798 | 400.00 |
| | | Depression | 84 | 69.385 | 88.404 | 2.220 | 400.00 |
| | | Diff (1-2) | — | -4.197 | 89.365 | — | — |
| | Crab | Control | 51 | 30.366 | 21.673 | 3.770 | 114.37 |
| | | Depression | 84 | 27.416 | 27.641 | 3.955 | 183.02 |
| | | Diff (1-2) | — | 2.951 | 25.562 | — | — |
| | Cucumber | Control | 51 | 6.559 | 5.110 | 1.269 | 26.496 |
| | | Depression | 84 | 10.518 | 12.910 | 1.655 | 105.57 |
| | | Diff (1-2) | — | -3.959 | 10.669 | — | — |
| | Egg | Control | 51 | 70.569 | 97.119 | 5.109 | 400.00 |
| | | Depression | 84 | 63.169 | 102.626 | 2.103 | 400.00 |
| | | Diff (1-2) | — | 7.399 | 100.591 | — | — |
| | Eggplant | Control | 51 | 3.980 | 4.120 | 0.100 | 26.496 |
| | | Depression | 84 | 4.808 | 4.545 | 0.769 | 31.159 |
| | | Diff (1-2) | — | -0.828 | 4.390 | — | — |
| | Garlic | Control | 51 | 8.615 | 4.650 | 0.100 | 23.410 |
| | | Depression | 84 | 12.491 | 21.359 | 2.825 | 195.76 |
| | | Diff (1-2) | — | -3.876 | 17.112 | — | — |
| | Goat_Milk | Control | 51 | 12.631 | 28.034 | 0.100 | 149.14 |
| | | Depression | 84 | 10.452 | 14.140 | 0.769 | 75.952 |
| | | Diff (1-2) | — | 2.179 | 20.499 | — | — |
| | Grape | Control | 51 | 13.069 | 6.123 | 2.351 | 44.190 |
| | | Depression | 84 | 11.984 | 6.244 | 5.166 | 48.166 |
| | | Diff (1-2) | — | 1.085 | 6.199 | — | — |
| | Grapefruit | Control | 51 | 3.129 | 1.808 | 0.100 | 8.039 |
| | | Depression | 84 | 4.425 | 4.535 | 0.473 | 27.688 |
| | | Diff (1-2) | — | -1.297 | 3.750 | — | — |
| | Green_Pea | Control | 51 | 5.735 | 5.596 | 0.100 | 27.006 |
| | | Depression | 84 | 6.700 | 5.824 | 1.473 | 32.598 |
| | | Diff (1-2) | — | -0.966 | 5.739 | — | — |
| | Green_Pepper | Control | 51 | 4.001 | 2.220 | 1.153 | 11.464 |
| | | Depression | 84 | 4.961 | 3.740 | 0.568 | 28.231 |
| | | Diff (1-2) | — | -0.960 | 3.253 | — | — |
| | Halibut | Control | 51 | 11.307 | 6.424 | 0.855 | 35.367 |
| | | Depression | 84 | 10.593 | 9.057 | 3.026 | 77.575 |
| | | Diff (1-2) | — | 0.713 | 8.167 | — | — |
| | Honey | Control | 51 | 8.234 | 3.765 | 0.534 | 22.795 |
| | | Depression | 84 | 11.119 | 9.294 | 3.158 | 69.779 |
| | | Diff (1-2) | — | -2.885 | 7.697 | — | — |
| | Lemon | Control | 51 | 2.560 | 1.273 | 0.100 | 6.269 |
| | | Depression | 84 | 2.960 | 1.809 | 0.100 | 10.352 |
| | | Diff (1-2) | — | -0.400 | 1.628 | — | — |
| | Lettuce | Control | 51 | 9.676 | 5.180 | 3.726 | 27.085 |
| | | Depression | 84 | 13.809 | 13.075 | 2.919 | 68.119 |
| | | Diff (1-2) | — | -4.133 | 10.807 | — | — |
| | Lima_Bean | Control | 51 | 4.955 | 4.158 | 0.100 | 25.007 |
| | | Depression | 84 | 5.594 | 3.681 | 0.100 | 22.803 |
| | | Diff (1-2) | — | -0.640 | 3.867 | — | — |
| | Lobster | Control | 51 | 7.008 | 4.348 | 1.175 | 23.980 |
| | | Depression | 84 | 7.919 | 9.497 | 0.302 | 81.273 |
| | | Diff (1-2) | — | -0.910 | 7.962 | — | — |
| | Malt | Control | 51 | 13.807 | 7.087 | 1.923 | 31.196 |
| | | Depression | 84 | 17.205 | 10.029 | 3.138 | 64.864 |
| | | Diff (1-2) | — | -3.399 | 9.036 | — | — |
| | Millet | Control | 51 | 3.883 | 6.158 | 0.100 | 45.888 |
| | | Depression | 84 | 3.293 | 1.457 | 0.284 | 7.902 |
| | | Diff (1-2) | — | 0.590 | 3.947 | — | — |
| | Mushroom | Control | 51 | 22.698 | 22.937 | 1.486 | 106.22 |
| | | Depression | 84 | 26.098 | 35.501 | 2.596 | 269.25 |
| | | Diff (1-2) | — | -3.399 | 31.374 | — | — |
| | Mustard | Control | 51 | 5.398 | 2.689 | 0.914 | 11.657 |
| | | Depression | 84 | 6.532 | 5.934 | 1.346 | 51.410 |
| | | Diff (1-2) | — | -1.133 | 4.969 | — | — |
| | Oat | Control | 51 | 11.120 | 9.563 | 0.100 | 49.538 |
| | | Depression | 84 | 21.731 | 30.234 | 1.224 | 172.55 |
| | | Diff (1-2) | — | -10.611 | 24.593 | — | — |

TABLE 3-continued

Basic Descriptive Statistics of ELISA Score by Food and Gender
Comparing Depression to Control

| Sex | Food | Diagnosis | N | ELISA Score |||| 
|---|---|---|---|---|---|---|---|
| | | | | Mean | SD | Min | Max |
| | Olive | Control | 51 | 15.480 | 19.299 | 3.048 | 111.23 |
| | | Depression | 84 | 15.462 | 13.966 | 1.815 | 83.159 |
| | | Diff (1-2) | — | 0.019 | 16.178 | — | — |
| | Onion | Control | 51 | 9.740 | 10.258 | 1.169 | 70.461 |
| | | Depression | 84 | 11.730 | 10.513 | 2.045 | 57.666 |
| | | Diff (1-2) | — | −1.990 | 10.418 | — | — |
| | Orange | Control | 51 | 23.728 | 28.881 | 4.173 | 149.43 |
| | | Depression | 84 | 40.043 | 61.930 | 3.273 | 400.00 |
| | | Diff (1-2) | — | −16.314 | 52.029 | — | — |
| | Oyster | Control | 51 | 44.125 | 34.722 | 9.622 | 168.93 |
| | | Depression | 84 | 47.302 | 55.126 | 2.746 | 365.92 |
| | | Diff (1-2) | — | −3.177 | 48.473 | — | — |
| | Parsley | Control | 51 | 21.959 | 46.256 | 5.988 | 342.33 |
| | | Depression | 84 | 23.172 | 46.201 | 4.615 | 395.02 |
| | | Diff (1-2) | — | −1.214 | 46.221 | — | — |
| | Peach | Control | 51 | 6.507 | 7.491 | 0.100 | 34.647 |
| | | Depression | 84 | 10.153 | 13.064 | 0.501 | 86.767 |
| | | Diff (1-2) | — | −3.646 | 11.296 | — | — |
| | Peanut | Control | 51 | 5.445 | 4.273 | 0.100 | 24.233 |
| | | Depression | 84 | 4.574 | 3.767 | 0.401 | 23.669 |
| | | Diff (1-2) | — | 0.871 | 3.965 | — | — |
| | Pineapple | Control | 51 | 8.460 | 18.977 | 0.100 | 122.86 |
| | | Depression | 84 | 9.496 | 10.815 | 0.301 | 68.963 |
| | | Diff (1-2) | — | −1.036 | 14.435 | — | — |
| | Pinto_Bean | Control | 51 | 9.830 | 9.653 | 0.214 | 47.923 |
| | | Depression | 84 | 9.690 | 8.769 | 1.519 | 49.208 |
| | | Diff (1-2) | — | 0.140 | 9.111 | — | — |
| | Pork | Control | 51 | 15.095 | 8.745 | 4.796 | 44.259 |
| | | Depression | 84 | 14.848 | 16.951 | 2.105 | 136.08 |
| | | Diff (1-2) | — | 0.247 | 14.424 | — | — |
| | Potato | Control | 51 | 8.664 | 2.240 | 4.899 | 14.014 |
| | | Depression | 84 | 9.829 | 6.551 | 3.530 | 50.433 |
| | | Diff (1-2) | — | −1.165 | 5.354 | — | — |
| | Rice | Control | 51 | 18.985 | 14.969 | 4.896 | 73.099 |
| | | Depression | 84 | 27.187 | 27.511 | 3.039 | 183.65 |
| | | Diff (1-2) | — | −8.203 | 23.591 | — | — |
| | Rye | Control | 51 | 4.185 | 2.647 | 0.229 | 17.994 |
| | | Depression | 84 | 5.528 | 6.331 | 0.568 | 50.541 |
| | | Diff (1-2) | — | −1.343 | 5.258 | — | — |
| | Safflower | Control | 51 | 6.557 | 5.363 | 1.619 | 36.646 |
| | | Depression | 84 | 10.104 | 18.078 | 1.513 | 158.79 |
| | | Diff (1-2) | — | −3.547 | 14.655 | — | — |
| | Salmon | Control | 51 | 13.155 | 11.632 | 3.483 | 68.368 |
| | | Depression | 84 | 11.244 | 7.823 | 2.005 | 38.104 |
| | | Diff (1-2) | — | 1.911 | 9.437 | — | — |
| | Sardine | Control | 51 | 29.733 | 14.098 | 12.950 | 76.726 |
| | | Depression | 84 | 29.036 | 13.839 | 7.297 | 71.123 |
| | | Diff (1-2) | — | 0.696 | 13.937 | — | — |
| | Scallop | Control | 51 | 53.504 | 22.302 | 15.624 | 107.71 |
| | | Depression | 84 | 48.185 | 31.160 | 12.400 | 183.38 |
| | | Diff (1-2) | — | 5.320 | 28.159 | — | — |
| | Sesame | Control | 51 | 91.740 | 91.167 | 6.639 | 400.00 |
| | | Depression | 84 | 74.492 | 86.939 | 3.652 | 400.00 |
| | | Diff (1-2) | — | 17.248 | 88.552 | — | — |
| | Shrimp | Control | 51 | 31.906 | 31.340 | 5.364 | 151.14 |
| | | Depression | 84 | 19.220 | 28.356 | 0.908 | 174.30 |
| | | Diff (1-2) | — | 12.685 | 29.513 | — | — |
| | Sole | Control | 51 | 5.010 | 3.858 | 0.229 | 29.089 |
| | | Depression | 84 | 5.160 | 3.607 | 0.568 | 32.149 |
| | | Diff (1-2) | — | −0.151 | 3.703 | — | — |
| | Soybean | Control | 51 | 14.277 | 10.254 | 4.153 | 51.573 |
| | | Depression | 84 | 20.340 | 45.681 | 1.412 | 330.35 |
| | | Diff (1-2) | — | −6.063 | 36.631 | — | — |
| | Spinach | Control | 51 | 20.914 | 15.580 | 3.294 | 66.869 |
| | | Depression | 84 | 19.305 | 19.975 | 3.530 | 112.21 |
| | | Diff (1-2) | — | 1.609 | 18.446 | — | — |
| | Squashes | Control | 51 | 5.697 | 2.997 | 2.054 | 13.836 |
| | | Depression | 84 | 7.591 | 7.642 | 1.461 | 61.130 |
| | | Diff (1-2) | — | −1.895 | 6.311 | — | — |
| | Strawberry | Control | 51 | 4.585 | 4.756 | 0.107 | 27.904 |
| | | Depression | 84 | 5.668 | 8.119 | 0.288 | 71.144 |
| | | Diff (1-2) | — | −1.083 | 7.046 | — | — |

TABLE 3-continued

Basic Descriptive Statistics of ELISA Score by Food and Gender
Comparing Depression to Control

| Sex | Food | Diagnosis | N | ELISA Score Mean | SD | Min | Max |
|---|---|---|---|---|---|---|---|
| | String_Bean | Control | 51 | 34.495 | 21.114 | 12.544 | 94.207 |
| | | Depression | 84 | 33.201 | 17.652 | 6.617 | 91.525 |
| | | Diff (1-2) | — | 1.294 | 19.028 | — | — |
| | Sunflower_Sd | Control | 51 | 7.402 | 4.308 | 1.487 | 21.171 |
| | | Depression | 84 | 8.016 | 5.975 | 1.420 | 42.615 |
| | | Diff (1-2) | — | -0.614 | 5.409 | — | — |
| | Sweet_Pot_ | Control | 51 | 13.319 | 8.694 | 4.463 | 53.650 |
| | | Depression | 84 | 17.751 | 42.527 | 3.013 | 387.79 |
| | | Diff (1-2) | — | -4.432 | 34.016 | — | — |
| | Swiss_Ch_ | Control | 51 | 37.893 | 78.801 | 1.486 | 400.00 |
| | | Depression | 84 | 32.905 | 56.882 | 1.422 | 369.23 |
| | | Diff (1-2) | — | 4.988 | 65.982 | — | — |
| | Tea | Control | 51 | 19.459 | 7.609 | 8.932 | 38.009 |
| | | Depression | 84 | 23.868 | 11.404 | 7.392 | 60.568 |
| | | Diff (1-2) | — | -4.409 | 10.145 | — | — |
| | Tobacco | Control | 51 | 28.550 | 13.486 | 7.878 | 65.658 |
| | | Depression | 84 | 40.993 | 33.443 | 6.961 | 266.42 |
| | | Diff (1-2) | — | -12.443 | 27.683 | — | — |
| | Tomato | Control | 51 | 7.412 | 5.926 | 1.915 | 30.764 |
| | | Depression | 84 | 11.842 | 14.852 | 1.052 | 121.09 |
| | | Diff (1-2) | — | -4.430 | 12.283 | — | — |
| | Trout | Control | 51 | 15.254 | 16.016 | 3.000 | 93.127 |
| | | Depression | 84 | 15.204 | 32.133 | 2.467 | 297.84 |
| | | Diff (1-2) | — | 0.050 | 27.217 | — | — |
| | Tuna | Control | 51 | 8.129 | 6.362 | 3.048 | 33.878 |
| | | Depression | 84 | 7.920 | 7.040 | 1.504 | 42.894 |
| | | Diff (1-2) | — | 0.209 | 6.793 | — | — |
| | Turkey | Control | 51 | 11.859 | 5.301 | 4.489 | 28.920 |
| | | Depression | 84 | 14.418 | 17.255 | 1.403 | 130.49 |
| | | Diff (1-2) | — | -2.559 | 14.013 | — | — |
| | Walnut_Blk | Control | 51 | 19.796 | 13.830 | 5.668 | 79.531 |
| | | Depression | 84 | 22.704 | 21.647 | 4.188 | 147.49 |
| | | Diff (1-2) | — | -2.908 | 19.088 | — | — |
| | Wheat | Control | 51 | 14.031 | 16.566 | 3.201 | 116.33 |
| | | Depression | 84 | 20.865 | 46.543 | 1.987 | 400.00 |
| | | Diff (1-2) | — | -6.834 | 38.145 | — | — |
| | Yeast_Baker | Control | 51 | 6.905 | 4.321 | 2.226 | 24.959 |
| | | Depression | 84 | 11.196 | 14.140 | 1.002 | 90.740 |
| | | Diff (1-2) | — | -4.292 | 11.480 | — | — |
| | Yeast_Brewer | Control | 51 | 9.946 | 8.059 | 1.486 | 37.536 |
| | | Depression | 84 | 16.898 | 21.682 | 2.220 | 133.32 |
| | | Diff (1-2) | — | -6.952 | 17.827 | — | — |
| | Yogurt | Control | 51 | 19.256 | 34.792 | 0.100 | 223.20 |
| | | Depression | 84 | 14.529 | 14.602 | 1.285 | 58.971 |
| | | Diff (1-2) | — | 4.727 | 24.252 | — | — |
| MALE | Almond | Control | 81 | 4.956 | 2.457 | 1.604 | 14.845 |
| | | Depression | 30 | 19.240 | 48.521 | 2.209 | 261.78 |
| | | Diff (1-2) | — | -14.284 | 25.116 | — | — |
| | Amer_Cheese | Control | 81 | 33.623 | 47.729 | 1.711 | 234.20 |
| | | Depression | 30 | 70.293 | 104.273 | 0.100 | 388.88 |
| | | Diff (1-2) | — | -36.670 | 67.563 | — | — |
| | Apple | Control | 81 | 4.768 | 4.226 | 0.994 | 30.113 |
| | | Depression | 30 | 10.226 | 17.862 | 1.473 | 91.492 |
| | | Diff (1-2) | — | -5.457 | 9.899 | — | — |
| | Avocado | Control | 81 | 2.949 | 2.085 | 0.201 | 15.507 |
| | | Depression | 30 | 4.977 | 6.902 | 0.670 | 29.430 |
| | | Diff (1-2) | — | -2.028 | 3.983 | — | — |
| | Banana | Control | 81 | 4.016 | 5.530 | 0.805 | 48.427 |
| | | Depression | 30 | 7.836 | 9.483 | 1.531 | 40.890 |
| | | Diff (1-2) | — | -3.820 | 6.810 | — | — |
| | Barley | Control | 81 | 9.009 | 35.683 | 1.081 | 324.19 |
| | | Depression | 30 | 15.659 | 45.746 | 1.435 | 254.23 |
| | | Diff (1-2) | — | -6.650 | 38.617 | — | — |
| | Beef | Control | 81 | 10.821 | 19.739 | 2.369 | 162.33 |
| | | Depression | 30 | 19.620 | 24.830 | 3.199 | 123.25 |
| | | Diff (1-2) | — | -8.799 | 21.213 | — | — |
| | Blueberry | Control | 81 | 3.790 | 2.257 | 0.883 | 12.559 |
| | | Depression | 30 | 5.614 | 5.070 | 1.031 | 26.070 |
| | | Diff (1-2) | — | -1.824 | 3.253 | — | — |
| | Broccoli | Control | 81 | 7.175 | 5.132 | 2.098 | 30.727 |
| | | Depression | 30 | 18.338 | 44.970 | 2.251 | 250.15 |
| | | Diff (1-2) | — | -11.163 | 23.609 | — | — |

TABLE 3-continued

Basic Descriptive Statistics of ELISA Score by Food and Gender
Comparing Depression to Control

| | | | | ELISA Score | | | |
|---|---|---|---|---|---|---|---|
| Sex | Food | Diagnosis | N | Mean | SD | Min | Max |
| | Buck_Wheat | Control | 81 | 5.548 | 3.014 | 1.667 | 23.702 |
| | | Depression | 30 | 9.870 | 9.819 | 2.762 | 54.212 |
| | | Diff (1-2) | — | -4.323 | 5.685 | — | — |
| | Butter | Control | 81 | 16.652 | 19.179 | 1.546 | 93.145 |
| | | Depression | 30 | 39.899 | 44.616 | 3.213 | 189.16 |
| | | Diff (1-2) | — | -23.246 | 28.277 | — | — |
| | Cabbage | Control | 81 | 5.952 | 10.811 | 0.985 | 94.740 |
| | | Depression | 30 | 20.647 | 62.792 | 1.244 | 347.26 |
| | | Diff (1-2) | — | -14.695 | 33.687 | — | — |
| | Cane_Sugar | Control | 81 | 23.047 | 28.025 | 3.898 | 170.78 |
| | | Depression | 30 | 30.241 | 26.558 | 5.441 | 131.80 |
| | | Diff (1-2) | — | -7.194 | 27.642 | — | — |
| | Cantaloupe | Control | 81 | 5.879 | 4.368 | 1.965 | 29.569 |
| | | Depression | 30 | 19.244 | 52.306 | 2.967 | 288.31 |
| | | Diff (1-2) | — | -13.366 | 27.238 | — | — |
| | Carrot | Control | 81 | 4.016 | 3.787 | 1.177 | 27.684 |
| | | Depression | 30 | 8.228 | 10.884 | 1.148 | 46.973 |
| | | Diff (1-2) | — | -4.212 | 6.484 | — | — |
| | Cashew | Control | 81 | 9.724 | 11.603 | 1.020 | 59.196 |
| | | Depression | 30 | 11.345 | 20.757 | 1.148 | 114.69 |
| | | Diff (1-2) | — | -1.621 | 14.609 | — | — |
| | Cauliflower | Control | 81 | 4.865 | 3.698 | 1.514 | 24.163 |
| | | Depression | 30 | 17.389 | 53.615 | 1.531 | 296.98 |
| | | Diff (1-2) | — | -12.524 | 27.836 | — | — |
| | Celery | Control | 81 | 8.967 | 5.476 | 2.947 | 34.787 |
| | | Depression | 30 | 20.042 | 50.509 | 3.677 | 284.26 |
| | | Diff (1-2) | — | -11.075 | 26.472 | — | — |
| | Cheddar_Ch_ | Control | 81 | 26.696 | 45.931 | 1.690 | 283.73 |
| | | Depression | 30 | 73.052 | 117.039 | 3.478 | 400.00 |
| | | Diff (1-2) | — | -46.355 | 72.061 | — | — |
| | Chicken | Control | 81 | 16.054 | 12.550 | 2.942 | 76.881 |
| | | Depression | 30 | 18.502 | 12.193 | 4.671 | 47.618 |
| | | Diff (1-2) | — | -2.449 | 12.456 | — | — |
| | Chili_Pepper | Control | 81 | 7.835 | 5.613 | 1.569 | 38.045 |
| | | Depression | 30 | 11.129 | 16.881 | 1.856 | 96.246 |
| | | Diff (1-2) | — | -3.295 | 9.947 | — | — |
| | Chocolate | Control | 81 | 16.623 | 11.019 | 3.007 | 59.473 |
| | | Depression | 30 | 22.913 | 15.578 | 4.307 | 70.958 |
| | | Diff (1-2) | — | -6.289 | 12.397 | — | — |
| | Cinnamon | Control | 81 | 9.850 | 7.037 | 1.640 | 40.477 |
| | | Depression | 30 | 12.445 | 8.317 | 1.133 | 30.988 |
| | | Diff (1-2) | — | -2.595 | 7.399 | — | — |
| | Clam | Control | 81 | 33.566 | 20.277 | 3.189 | 98.482 |
| | | Depression | 30 | 36.898 | 54.757 | 9.750 | 318.14 |
| | | Diff (1-2) | — | -3.332 | 33.159 | — | — |
| | Codfish | Control | 81 | 25.075 | 33.650 | 6.487 | 277.17 |
| | | Depression | 30 | 45.890 | 73.290 | 7.959 | 400.00 |
| | | Diff (1-2) | — | -20.815 | 47.541 | — | — |
| | Coffee | Control | 81 | 30.318 | 43.408 | 4.323 | 356.95 |
| | | Depression | 30 | 53.598 | 98.346 | 5.268 | 400.00 |
| | | Diff (1-2) | — | -23.280 | 62.898 | — | — |
| | Cola_Nut | Control | 81 | 15.243 | 8.049 | 4.084 | 38.816 |
| | | Depression | 30 | 16.580 | 9.872 | 4.987 | 50.994 |
| | | Diff (1-2) | — | -1.337 | 8.572 | — | — |
| | Corn | Control | 81 | 9.923 | 12.544 | 2.358 | 95.512 |
| | | Depression | 30 | 29.487 | 48.938 | 2.297 | 185.58 |
| | | Diff (1-2) | — | -19.564 | 27.435 | — | — |
| | Cottage_Ch_ | Control | 81 | 76.631 | 102.973 | 1.207 | 400.00 |
| | | Depression | 30 | 140.923 | 154.222 | 5.851 | 400.00 |
| | | Diff (1-2) | — | -64.292 | 118.787 | — | — |
| | Cow_Milk | Control | 81 | 60.822 | 83.166 | 1.767 | 400.00 |
| | | Depression | 30 | 131.551 | 144.182 | 4.282 | 400.00 |
| | | Diff (1-2) | — | -70.728 | 102.991 | — | — |
| | Crab | Control | 81 | 32.448 | 37.288 | 4.765 | 299.11 |
| | | Depression | 30 | 36.378 | 35.136 | 7.680 | 194.02 |
| | | Diff (1-2) | — | -3.930 | 36.728 | — | — |
| | Cucumber | Control | 81 | 8.752 | 8.584 | 1.877 | 61.859 |
| | | Depression | 30 | 28.024 | 60.943 | 2.830 | 320.56 |
| | | Diff (1-2) | — | -19.272 | 32.284 | — | — |
| | Egg | Control | 81 | 62.505 | 92.408 | 3.785 | 400.00 |
| | | Depression | 30 | 85.498 | 116.862 | 3.215 | 400.00 |
| | | Diff (1-2) | — | -22.994 | 99.503 | — | — |

TABLE 3-continued

Basic Descriptive Statistics of ELISA Score by Food and Gender
Comparing Depression to Control

| Sex | Food | Diagnosis | N | ELISA Score Mean | SD | Min | Max |
|---|---|---|---|---|---|---|---|
| | Eggplant | Control | 81 | 5.045 | 5.910 | 1.367 | 48.789 |
| | | Depression | 30 | 10.459 | 16.348 | 1.603 | 70.249 |
| | | Diff (1-2) | — | −5.414 | 9.836 | — | — |
| | Garlic | Control | 81 | 11.918 | 9.606 | 3.041 | 52.161 |
| | | Depression | 30 | 14.955 | 16.035 | 2.834 | 88.234 |
| | | Diff (1-2) | — | −3.037 | 11.668 | — | — |
| | Goat_Milk | Control | 81 | 11.176 | 16.325 | 0.503 | 96.689 |
| | | Depression | 30 | 35.670 | 59.210 | 1.879 | 210.41 |
| | | Diff (1-2) | — | −24.493 | 33.591 | — | — |
| | Grape | Control | 81 | 15.645 | 5.750 | 8.058 | 47.251 |
| | | Depression | 30 | 21.674 | 38.577 | 4.906 | 221.13 |
| | | Diff (1-2) | — | −6.029 | 20.499 | — | — |
| | Grapefruit | Control | 81 | 4.255 | 3.962 | 0.807 | 32.913 |
| | | Depression | 30 | 11.231 | 30.159 | 0.957 | 163.43 |
| | | Diff (1-2) | — | −6.976 | 15.922 | — | — |
| | Green_Pea | Control | 81 | 7.021 | 6.334 | 1.020 | 35.195 |
| | | Depression | 30 | 9.031 | 6.837 | 1.818 | 30.562 |
| | | Diff (1-2) | — | −2.010 | 6.471 | — | — |
| | Green_Pepper | Control | 81 | 4.715 | 3.713 | 1.656 | 32.327 |
| | | Depression | 30 | 14.672 | 46.012 | 0.957 | 256.35 |
| | | Diff (1-2) | — | −9.956 | 23.945 | — | — |
| | Halibut | Control | 81 | 14.289 | 15.877 | 4.414 | 135.74 |
| | | Depression | 30 | 19.259 | 22.743 | 4.874 | 96.737 |
| | | Diff (1-2) | — | −4.970 | 17.962 | — | — |
| | Honey | Control | 81 | 10.351 | 5.111 | 2.733 | 29.823 |
| | | Depression | 30 | 14.751 | 10.807 | 3.490 | 51.631 |
| | | Diff (1-2) | — | −4.400 | 7.089 | — | — |
| | Lemon | Control | 81 | 3.050 | 2.460 | 0.201 | 20.655 |
| | | Depression | 30 | 4.648 | 6.262 | 0.377 | 26.648 |
| | | Diff (1-2) | — | −1.598 | 3.857 | — | — |
| | Lettuce | Control | 81 | 12.814 | 7.663 | 3.734 | 39.966 |
| | | Depression | 30 | 27.973 | 42.368 | 4.151 | 211.92 |
| | | Diff (1-2) | — | −15.159 | 22.818 | — | — |
| | Lima_Bean | Control | 81 | 6.294 | 5.248 | 1.546 | 35.107 |
| | | Depression | 30 | 8.145 | 7.785 | 0.928 | 36.538 |
| | | Diff (1-2) | — | −1.851 | 6.028 | — | — |
| | Lobster | Control | 81 | 9.455 | 6.640 | 1.311 | 41.983 |
| | | Depression | 30 | 8.911 | 6.106 | 2.808 | 26.300 |
| | | Diff (1-2) | — | 0.544 | 6.502 | — | — |
| | Malt | Control | 81 | 15.173 | 8.267 | 2.551 | 51.285 |
| | | Depression | 30 | 20.386 | 11.297 | 6.461 | 53.111 |
| | | Diff (1-2) | — | −5.213 | 9.171 | — | — |
| | Millet | Control | 81 | 4.065 | 4.304 | 1.435 | 40.360 |
| | | Depression | 30 | 4.712 | 2.347 | 1.340 | 9.527 |
| | | Diff (1-2) | — | −0.647 | 3.881 | — | — |
| | Mushroom | Control | 81 | 27.235 | 27.375 | 2.824 | 118.76 |
| | | Depression | 30 | 32.179 | 33.673 | 4.434 | 131.33 |
| | | Diff (1-2) | — | −4.944 | 29.184 | — | — |
| | Mustard | Control | 81 | 6.992 | 4.301 | 1.947 | 30.771 |
| | | Depression | 30 | 16.454 | 41.250 | 2.547 | 233.06 |
| | | Diff (1-2) | — | −9.462 | 21.593 | — | — |
| | Oat | Control | 81 | 18.201 | 20.144 | 1.176 | 88.428 |
| | | Depression | 30 | 32.643 | 54.940 | 0.567 | 294.01 |
| | | Diff (1-2) | — | −14.442 | 33.180 | — | — |
| | Olive | Control | 81 | 17.589 | 31.696 | 3.554 | 281.30 |
| | | Depression | 30 | 41.626 | 68.210 | 4.194 | 274.07 |
| | | Diff (1-2) | — | −24.037 | 44.443 | — | — |
| | Onion | Control | 81 | 13.450 | 23.822 | 2.271 | 210.93 |
| | | Depression | 30 | 39.203 | 83.172 | 1.698 | 400.00 |
| | | Diff (1-2) | — | −25.753 | 47.508 | — | — |
| | Orange | Control | 81 | 26.423 | 37.325 | 2.824 | 314.77 |
| | | Depression | 30 | 59.267 | 67.356 | 5.328 | 279.36 |
| | | Diff (1-2) | — | −32.843 | 47.218 | — | — |
| | Oyster | Control | 81 | 49.594 | 42.026 | 7.658 | 250.39 |
| | | Depression | 30 | 101.583 | 81.794 | 9.637 | 278.65 |
| | | Diff (1-2) | — | −51.989 | 55.464 | — | — |
| | Parsley | Control | 81 | 17.745 | 7.652 | 5.298 | 59.623 |
| | | Depression | 30 | 32.472 | 53.175 | 9.491 | 303.98 |
| | | Diff (1-2) | — | −14.727 | 28.201 | — | — |
| | Peach | Control | 81 | 10.414 | 10.155 | 1.913 | 53.125 |
| | | Depression | 30 | 17.293 | 21.222 | 1.415 | 80.424 |
| | | Diff (1-2) | — | −6.880 | 13.983 | — | — |

TABLE 3-continued

Basic Descriptive Statistics of ELISA Score by Food and Gender Comparing Depression to Control

| Sex | Food | Diagnosis | N | ELISA Score | | | |
|---|---|---|---|---|---|---|---|
| | | | | Mean | SD | Min | Max |
| | Peanut | Control | 81 | 5.730 | 9.913 | 1.223 | 89.273 |
| | | Depression | 30 | 12.104 | 22.293 | 1.340 | 102.94 |
| | | Diff (1-2) | — | −6.374 | 14.295 | — | — |
| | Pineapple | Control | 81 | 12.433 | 44.326 | 1.660 | 400.00 |
| | | Depression | 30 | 22.446 | 42.174 | 0.943 | 211.16 |
| | | Diff (1-2) | — | −10.013 | 43.764 | — | — |
| | Pinto_Bean | Control | 81 | 9.370 | 6.088 | 1.998 | 33.952 |
| | | Depression | 30 | 26.024 | 65.400 | 3.067 | 359.76 |
| | | Diff (1-2) | — | −16.653 | 34.135 | — | — |
| | Pork | Control | 81 | 16.675 | 14.641 | 4.198 | 89.423 |
| | | Depression | 30 | 15.489 | 8.675 | 4.774 | 38.269 |
| | | Diff (1-2) | — | 1.186 | 13.317 | — | — |
| | Potato | Control | 81 | 12.243 | 8.339 | 4.922 | 75.768 |
| | | Depression | 30 | 25.142 | 68.240 | 2.830 | 383.04 |
| | | Diff (1-2) | — | −12.899 | 35.916 | — | — |
| | Rice | Control | 81 | 24.230 | 16.518 | 4.815 | 79.625 |
| | | Depression | 30 | 39.755 | 72.482 | 5.189 | 400.00 |
| | | Diff (1-2) | — | −15.525 | 39.975 | — | — |
| | Rye | Control | 81 | 5.122 | 3.376 | 1.569 | 23.489 |
| | | Depression | 30 | 9.176 | 9.594 | 1.341 | 46.668 |
| | | Diff (1-2) | — | −4.055 | 5.732 | — | — |
| | Safflower | Control | 81 | 7.553 | 4.020 | 2.452 | 27.492 |
| | | Depression | 30 | 10.295 | 8.332 | 2.169 | 35.466 |
| | | Diff (1-2) | — | −2.742 | 5.507 | — | — |
| | Salmon | Control | 81 | 16.307 | 15.972 | 0.100 | 136.52 |
| | | Depression | 30 | 17.538 | 32.725 | 4.563 | 188.91 |
| | | Diff (1-2) | — | −1.231 | 21.730 | — | — |
| | Sardine | Control | 81 | 33.099 | 14.613 | 7.838 | 87.492 |
| | | Depression | 30 | 34.114 | 16.377 | 10.600 | 91.647 |
| | | Diff (1-2) | — | −1.015 | 15.103 | — | — |
| | Scallop | Control | 81 | 50.308 | 23.097 | 11.061 | 116.33 |
| | | Depression | 30 | 49.327 | 18.669 | 26.003 | 105.18 |
| | | Diff (1-2) | — | 0.980 | 22.006 | — | — |
| | Sesame | Control | 81 | 73.449 | 87.622 | 3.433 | 400.00 |
| | | Depression | 30 | 87.565 | 119.362 | 6.227 | 400.00 |
| | | Diff (1-2) | — | −14.116 | 97.085 | — | — |
| | Shrimp | Control | 81 | 34.185 | 40.052 | 2.925 | 272.28 |
| | | Depression | 30 | 23.914 | 41.579 | 4.681 | 236.84 |
| | | Diff (1-2) | — | 10.271 | 40.464 | — | — |
| | Sole | Control | 81 | 5.290 | 2.521 | 2.243 | 20.373 |
| | | Depression | 30 | 5.586 | 2.457 | 2.166 | 10.613 |
| | | Diff (1-2) | — | −0.296 | 2.504 | — | — |
| | Soybean | Control | 81 | 16.814 | 12.312 | 3.479 | 81.383 |
| | | Depression | 30 | 43.489 | 82.869 | 5.580 | 400.00 |
| | | Diff (1-2) | — | −26.676 | 44.026 | — | — |
| | Spinach | Control | 81 | 14.620 | 6.503 | 5.378 | 40.130 |
| | | Depression | 30 | 33.807 | 70.886 | 6.133 | 400.00 |
| | | Diff (1-2) | — | −19.188 | 36.985 | — | — |
| | Squashes | Control | 81 | 7.200 | 4.790 | 2.259 | 24.675 |
| | | Depression | 30 | 21.468 | 64.320 | 1.981 | 357.62 |
| | | Diff (1-2) | — | −14.268 | 33.430 | — | — |
| | Strawberry | Control | 81 | 5.073 | 4.417 | 1.002 | 29.163 |
| | | Depression | 30 | 25.236 | 73.898 | 1.341 | 400.00 |
| | | Diff (1-2) | — | −20.163 | 38.305 | — | — |
| | String_Bean | Control | 81 | 37.257 | 22.322 | 7.894 | 146.17 |
| | | Depression | 30 | 43.417 | 25.642 | 12.241 | 129.91 |
| | | Diff (1-2) | — | −6.160 | 23.252 | — | — |
| | Sunflower_Sd | Control | 81 | 8.566 | 5.303 | 2.451 | 31.256 |
| | | Depression | 30 | 18.573 | 40.806 | 2.888 | 231.71 |
| | | Diff (1-2) | — | −10.007 | 21.533 | — | — |
| | Sweet_Pot_ | Control | 81 | 17.536 | 13.698 | 4.101 | 74.660 |
| | | Depression | 30 | 28.901 | 43.655 | 2.735 | 230.69 |
| | | Diff (1-2) | — | −11.365 | 25.392 | — | — |
| | Swiss_Ch_ | Control | 81 | 35.608 | 58.963 | 2.010 | 299.50 |
| | | Depression | 30 | 88.439 | 135.669 | 3.237 | 400.00 |
| | | Diff (1-2) | — | −52.831 | 86.306 | — | — |
| | Tea | Control | 81 | 23.966 | 9.868 | 7.617 | 46.395 |
| | | Depression | 30 | 31.665 | 19.407 | 8.589 | 101.02 |
| | | Diff (1-2) | — | −7.699 | 13.102 | — | — |
| | Tobacco | Control | 81 | 36.231 | 21.642 | 8.831 | 125.93 |
| | | Depression | 30 | 61.161 | 58.497 | 11.649 | 312.01 |
| | | Diff (1-2) | — | −24.930 | 35.414 | — | — |

TABLE 3-continued

Basic Descriptive Statistics of ELISA Score by Food and Gender
Comparing Depression to Control

| Sex | Food | Diagnosis | N | ELISA Score Mean | SD | Min | Max |
|---|---|---|---|---|---|---|---|
| | Tomato | Control | 81 | 9.199 | 6.995 | 2.319 | 40.933 |
| | | Depression | 30 | 42.152 | 95.827 | 1.509 | 400.00 |
| | | Diff (1-2) | — | −32.953 | 49.790 | — | — |
| | Trout | Control | 81 | 14.686 | 9.992 | 3.220 | 83.963 |
| | | Depression | 30 | 19.945 | 42.469 | 2.207 | 242.68 |
| | | Diff (1-2) | — | −5.259 | 23.519 | — | — |
| | Tuna | Control | 81 | 8.305 | 6.513 | 2.110 | 39.025 |
| | | Depression | 30 | 8.443 | 7.910 | 1.428 | 36.792 |
| | | Diff (1-2) | — | −0.138 | 6.912 | — | — |
| | Turkey | Control | 81 | 14.012 | 11.116 | 4.079 | 65.177 |
| | | Depression | 30 | 13.494 | 8.545 | 5.336 | 39.414 |
| | | Diff (1-2) | — | 0.518 | 10.494 | — | — |
| | Walnut_Blk | Control | 81 | 20.821 | 10.402 | 5.682 | 58.466 |
| | | Depression | 30 | 35.105 | 71.023 | 7.028 | 400.00 |
| | | Diff (1-2) | — | −14.284 | 37.702 | — | — |
| | Wheat | Control | 81 | 13.359 | 10.034 | 3.237 | 71.930 |
| | | Depression | 30 | 38.088 | 73.346 | 4.815 | 352.91 |
| | | Diff (1-2) | — | −24.729 | 38.796 | — | — |
| | Yeast_Baker | Control | 81 | 12.471 | 20.370 | 2.073 | 123.35 |
| | | Depression | 30 | 18.870 | 30.129 | 1.132 | 127.47 |
| | | Diff (1-2) | — | −6.399 | 23.368 | — | — |
| | Yeast_Brewer | Control | 81 | 15.903 | 21.143 | 2.642 | 130.89 |
| | | Depression | 30 | 29.020 | 52.876 | 1.603 | 246.75 |
| | | Diff (1-2) | — | −13.117 | 32.741 | — | — |
| | Yogurt | Control | 81 | 15.651 | 16.295 | 3.004 | 73.200 |
| | | Depression | 30 | 42.777 | 72.527 | 4.245 | 327.88 |
| | | Diff (1-2) | — | −27.126 | 39.930 | — | — |

TABLE 4

Upper Quantiles of ELISA Signal Scores among Control Subjects as Candidates for Test Cutpoints in Determining "Positive" or "Negative" Top 26 Foods Ranked by Descending order of Discriminatory Ability using Permutation Test Depression Subjects vs. Controls

| Food Ranking | Food | Sex | Cutpoint 90th percentile | 95th percentile |
|---|---|---|---|---|
| 1 | Almond | FEMALE | 6.387 | 7.229 |
| | | MALE | 8.201 | 10.364 |
| 2 | Tomato | FEMALE | 12.707 | 20.229 |
| | | MALE | 16.458 | 23.901 |
| 3 | Tobacco | FEMALE | 46.676 | 52.120 |
| | | MALE | 66.108 | 81.270 |
| 4 | Carrot | FEMALE | 5.028 | 6.030 |
| | | MALE | 6.547 | 9.472 |
| 5 | Orange | FEMALE | 58.970 | 90.702 |
| | | MALE | 47.782 | 67.581 |
| 6 | Cucumber | FEMALE | 12.530 | 18.094 |
| | | MALE | 16.117 | 22.938 |
| 7 | Broccoli | FEMALE | 9.078 | 12.242 |
| | | MALE | 13.227 | 17.923 |
| 8 | Lettuce | FEMALE | 17.214 | 21.301 |
| | | MALE | 23.159 | 30.500 |
| 9 | Malt | FEMALE | 24.428 | 26.838 |
| | | MALE | 26.135 | 30.793 |
| 10 | Cantaloupe | FEMALE | 7.816 | 9.816 |
| | | MALE | 10.244 | 14.900 |
| 11 | Corn | FEMALE | 13.133 | 19.396 |
| | | MALE | 16.893 | 27.942 |
| 12 | Wheat | FEMALE | 22.473 | 39.657 |
| | | MALE | 23.851 | 30.952 |
| 13 | Honey | FEMALE | 12.418 | 14.289 |
| | | MALE | 17.319 | 20.797 |
| 14 | Chocolate | FEMALE | 22.428 | 24.874 |
| | | MALE | 31.758 | 37.652 |
| 15 | Oat | FEMALE | 22.737 | 27.403 |
| | | MALE | 52.310 | 63.866 |
| 16 | Avocado | FEMALE | 3.604 | 4.378 |
| | | MALE | 4.620 | 6.230 |
| 17 | Rye | FEMALE | 6.138 | 8.899 |
| | | MALE | 8.345 | 11.849 |
| 18 | Strawberry | FEMALE | 8.038 | 14.219 |
| | | MALE | 9.266 | 13.944 |
| 19 | Cauliflower | FEMALE | 7.651 | 9.029 |
| | | MALE | 7.718 | 12.080 |
| 20 | Safflower | FEMALE | 10.386 | 16.047 |
| | | MALE | 11.748 | 14.739 |
| 21 | Tea | FEMALE | 29.842 | 33.214 |
| | | MALE | 37.508 | 42.162 |
| 22 | Banana | FEMALE | 5.442 | 9.272 |
| | | MALE | 6.610 | 10.019 |
| 23 | Squashes | FEMALE | 10.270 | 11.945 |
| | | MALE | 13.571 | 18.431 |
| 24 | Green_Pepper | FEMALE | 6.908 | 8.215 |
| | | MALE | 7.040 | 9.133 |
| 25 | Butter | FEMALE | 40.015 | 66.921 |
| | | MALE | 44.018 | 61.716 |
| 26 | Buck_Wheat | FEMALE | 9.667 | 13.975 |
| | | MALE | 8.502 | 10.282 |

TABLE 5A

| Sample ID | # of Positive Results Based on 90th Percentile |
|---|---|
| DEPRESSION POPULATION | |
| 171081AAB0001 | 0 |
| 171081AAB0002 | 0 |
| 171081AAB0003 | 4 |
| 171081AAB0004 | 0 |
| 171081AAB0005 | 5 |
| 171081AAB0006 | 1 |
| 171081AAB0008 | 3 |
| 171081AAB0009 | 5 |
| 171081AAB0010 | 0 |
| 171081AAB0011 | 3 |
| 171081AAB0012 | 5 |
| 171081AAB0014 | 18 |
| 171081AAB0015 | 1 |
| 171081AAB0016 | 5 |
| 171081AAB0017 | 11 |
| 171081AAB0018 | 7 |
| 171081AAB0019 | 1 |
| 171081AAB0020 | 1 |
| 171081AAB0022 | 7 |
| 171081AAB0023 | 1 |
| 171081AAB0025 | 0 |
| 171081AAB0027 | 18 |
| 171081AAB0028 | 8 |
| 171081AAB0029 | 11 |
| 171081AAB0030 | 2 |
| 171081AAB0032 | 7 |
| 171081AAB0033 | 19 |
| 171081AAB0037 | 4 |
| 171081AAB0039 | 1 |
| 171081AAB0040 | 8 |
| 171081AAB0043 | 0 |
| 171081AAB0044 | 13 |
| 171081AAB0045 | 0 |
| 171081AAB0046 | 0 |
| 171081AAB0047 | 7 |
| 171081AAB0049 | 18 |
| 171146AAB0002 | 0 |
| 171146AAB0003 | 4 |
| 171146AAB0004 | 2 |
| 171146AAB0005 | 1 |
| 171146AAB0006 | 1 |
| 171146AAB0007 | 0 |
| 171146AAB0008 | 6 |
| 171146AAB0009 | 7 |
| 171146AAB0010 | 1 |
| 171146AAB0011 | 14 |
| 171146AAB0013 | 1 |
| 171146AAB0014 | 3 |
| 171146AAB0015 | 4 |
| 171146AAB0016 | 0 |
| 171146AAB0017 | 3 |
| 171146AAB0018 | 5 |
| 171146AAB0019 | 11 |
| 171146AAB0020 | 2 |
| 171146AAB0021 | 7 |
| 171146AAB0022 | 11 |
| 171146AAB0023 | 7 |
| 171146AAB0025 | 3 |
| 171146AAB0026 | 1 |
| 171146AAB0027 | 2 |
| 171146AAB0028 | 12 |
| 171146AAB0029 | 0 |
| 171146AAB0030 | 0 |
| 171146AAB0031 | 1 |
| 171146AAB0032 | 4 |
| 171146AAB0033 | 0 |
| 171146AAB0036 | 7 |
| BRH1339646 | 0 |
| BRH1339647 | 2 |
| BRH1339648 | 1 |
| BRH1339649 | 0 |
| BRH1339650 | 0 |
| BRH1339655 | 6 |
| BRH1339657 | 1 |
| BRH1339658 | 2 |
| BRH1339659 | 0 |
| BRH1339660 | 0 |
| BRH1339662 | 0 |
| BRH1339664 | 6 |
| BRH1339666 | 0 |
| BRH1339667 | 0 |
| BRH1339668 | 4 |
| BRH1339669 | 20 |
| BRH1339670 | 1 |
| 171081AAB0007 | 17 |
| 171081AAB0013 | 2 |
| 171081AAB0021 | 9 |
| 171081AAB0024 | 7 |
| 171081AAB0026 | 11 |
| 171081AAB0031 | 18 |
| 171081AAB0034 | 14 |
| 171081AAB0035 | 2 |
| 171081AAB0036 | 0 |
| 171081AAB0038 | 7 |
| 171081AAB0041 | 0 |
| 171081AAB0042 | 2 |
| 171081AAB0048 | 0 |
| 171081AAB0050 | 1 |
| 171146AAB0012 | 0 |
| 171146AAB0024 | 0 |
| 171146AAB0034 | 16 |
| 171146AAB0035 | 7 |
| 171146AAB0037 | 6 |
| 171146AAB0038 | 1 |
| 171146AAB0039 | 0 |
| 171146AAB0040 | 2 |
| BRH1339651 | 7 |
| BRH1339652 | 0 |
| BRH1339653 | 0 |
| BRH1339654 | 14 |
| BRH1339656 | 1 |
| BRH1339661 | 2 |
| BRH1339663 | 1 |
| BRH1339665 | 0 |
| No of Observations | 114 |
| Average Number | 4.4 |
| Median Number | 2 |
| # of Patients w/0 Pos Results | 31 |
| % Subjects w/0 pos results | 27.2 |
| NON-DEPRESSION POPULATION | |
| BRH1244994 | 2 |
| BRH1244995 | 0 |
| BRH1244996 | 1 |
| BRH1244997 | 0 |
| BRH1244998 | 3 |
| BRH1244999 | 0 |
| BRH1245000 | 1 |
| BRH1245001 | 0 |
| BRH1245002 | 1 |
| BRH1245004 | 0 |
| BRH1245007 | 0 |
| BRH1245008 | 0 |
| BRH1245009 | 3 |
| BRH1245010 | 4 |
| BRH1245011 | 4 |
| BRH1245014 | 0 |
| BRH1245015 | 0 |
| BRH1245018 | 1 |
| BRH1245019 | 0 |
| BRH1245022 | 11 |
| BRH1245023 | 1 |
| BRH1245024 | 2 |
| BRH1245026 | 4 |
| BRH1245029 | 0 |
| BRH1245030 | 0 |
| BRH1245031 | 3 |
| BRH1245032 | 1 |
| BRH1245033 | 0 |
| BRH1245035 | 0 |
| BRH1245037 | 0 |
| BRH1245038 | 0 |

TABLE 5A-continued

| Sample ID | # of Positive Results Based on 90th Percentile |
|---|---|
| BRH1245039 | 11 |
| BRH1245040 | 2 |
| BRH1245041 | 2 |
| BRH1267328 | 12 |
| BRH1267329 | 1 |
| BRH1267330 | 0 |
| BRH1267332 | 0 |
| BRH1267333 | 0 |
| BRH1267334 | 12 |
| BRH1267335 | 3 |
| BRH1267337 | 0 |
| BRH1267338 | 0 |
| BRH1267339 | 1 |
| BRH1267340 | 6 |
| BRH1267341 | 0 |
| BRH1267343 | 3 |
| BRH1267345 | 0 |
| BRH1267346 | 0 |
| BRH1267347 | 0 |
| BRH1267349 | 0 |
| BRH1244900 | 0 |
| BRH1244901 | 6 |
| BRH1244902 | 0 |
| BRH1244903 | 0 |
| BRH1244904 | 1 |
| BRH1244905 | 0 |
| BRH1244906 | 11 |
| BRH1244907 | 0 |
| BRH1244908 | 1 |
| BRH1244909 | 0 |
| BRH1244910 | 3 |
| BRH1244911 | 2 |
| BRH1244912 | 1 |
| BRH1244913 | 0 |
| BRH1244914 | 7 |
| BRH1244915 | 1 |
| BRH1244916 | 14 |
| BRH1244917 | 11 |
| BRH1244918 | 0 |
| BRH1244920 | 2 |
| BRH1244921 | 0 |
| BRH1244922 | 14 |
| BRH1244923 | 1 |
| BRH1244924 | 0 |
| BRH1244925 | 1 |
| BRH1244926 | 10 |
| BRH1244928 | 1 |
| BRH1244929 | 3 |
| BRH1244931 | 0 |
| BRH1244932 | 2 |
| BRH1244933 | 4 |
| BRH1244934 | 2 |
| BRH1244938 | 4 |
| BRH1244939 | 0 |
| BRH1244940 | 0 |
| BRH1244941 | 0 |
| BRH1244942 | 4 |
| BRH1244943 | 1 |
| BRH1244944 | 10 |
| BRH1244945 | 1 |
| BRH1244946 | 5 |
| BRH1244947 | 0 |
| BRH1244948 | 0 |
| BRH1244949 | 1 |
| BRH1244950 | 0 |
| BRH1244951 | 0 |
| BRH1244952 | 0 |
| BRH1244953 | 1 |
| BRH1244954 | 0 |
| BRH1244956 | 18 |
| BRH1244959 | 1 |
| BRH1244960 | 0 |
| BRH1244961 | 0 |
| BRH1244962 | 0 |
| BRH1244963 | 0 |
| BRH1244964 | 5 |
| BRH1244965 | 0 |
| BRH1244967 | 0 |
| BRH1244969 | 0 |
| BRH1244970 | 1 |
| BRH1244971 | 1 |
| BRH1244972 | 0 |
| BRH1244973 | 2 |
| BRH1244974 | 0 |
| BRH1244975 | 0 |
| BRH1244976 | 0 |
| BRH1244977 | 0 |
| BRH1244979 | 0 |
| BRH1244980 | 0 |
| BRH1244981 | 0 |
| BRH1244982 | 0 |
| BRH1244983 | 0 |
| BRH1244985 | 0 |
| BRH1244987 | 0 |
| BRH1244988 | 2 |
| BRH1244991 | 0 |
| BRH1244992 | 2 |
| BRH1267320 | 0 |
| BRH1267322 | 4 |
| BRH1267323 | 0 |
| BRH1267325 | 3 |
| No of Observations | 132 |
| Average Number | 2.0 |
| Median Number | 0 |
| # of Patients w/0 Pos Results | 68 |
| % Subjects w/0 pos results | 51.5 |

TABLE 5B

| Sample ID | # of Positive Results Based on 95th Percentile |
|---|---|
| DEPRESSION POPULATION | |
| 171081AAB0001 | 0 |
| 171081AAB0002 | 0 |
| 171081AAB0003 | 1 |
| 171081AAB0004 | 0 |
| 171081AAB0005 | 1 |
| 171081AAB0006 | 1 |
| 171081AAB0008 | 2 |
| 171081AAB0009 | 4 |
| 171081AAB0010 | 0 |
| 171081AAB0011 | 3 |
| 171081AAB0012 | 1 |
| 171081AAB0014 | 15 |
| 171081AAB0015 | 1 |
| 171081AAB0016 | 4 |
| 171081AAB0017 | 5 |
| 171081AAB0018 | 3 |
| 171081AAB0019 | 1 |
| 171081AAB0020 | 1 |
| 171081AAB0022 | 3 |
| 171081AAB0023 | 0 |
| 171081AAB0025 | 0 |
| 171081AAB0027 | 12 |
| 171081AAB0028 | 6 |
| 171081AAB0029 | 6 |
| 171081AAB0030 | 0 |
| 171081AAB0032 | 5 |
| 171081AAB0033 | 17 |
| 171081AAB0037 | 1 |
| 171081AAB0039 | 0 |
| 171081AAB0040 | 7 |
| 171081AAB0043 | 0 |
| 171081AAB0044 | 11 |
| 171081AAB0045 | 0 |
| 171081AAB0046 | 0 |
| 171081AAB0047 | 6 |
| 171081AAB0049 | 9 |
| 171146AAB0002 | 0 |

TABLE 5B-continued

| Sample ID | # of Positive Results Based on 95th Percentile |
|---|---|
| 171146AAB0003 | 1 |
| 171146AAB0004 | 2 |
| 171146AAB0005 | 0 |
| 171146AAB0006 | 0 |
| 171146AAB0007 | 0 |
| 171146AAB0008 | 3 |
| 171146AAB0009 | 5 |
| 171146AAB0010 | 0 |
| 171146AAB0011 | 9 |
| 171146AAB0013 | 0 |
| 171146AAB0014 | 1 |
| 171146AAB0015 | 0 |
| 171146AAB0016 | 0 |
| 171146AAB0017 | 1 |
| 171146AAB0018 | 2 |
| 171146AAB0019 | 8 |
| 171146AAB0020 | 1 |
| 171146AAB0021 | 4 |
| 171146AAB0022 | 8 |
| 171146AAB0023 | 6 |
| 171146AAB0025 | 2 |
| 171146AAB0026 | 1 |
| 171146AAB0027 | 1 |
| 171146AAB0028 | 9 |
| 171146AAB0029 | 0 |
| 171146AAB0030 | 0 |
| 171146AAB0031 | 0 |
| 171146AAB0032 | 4 |
| 171146AAB0033 | 0 |
| 171146AAB0036 | 2 |
| BRH1339646 | 0 |
| BRH1339647 | 1 |
| BRH1339648 | 0 |
| BRH1339649 | 0 |
| BRH1339650 | 0 |
| BRH1339655 | 4 |
| BRH1339657 | 1 |
| BRH1339658 | 1 |
| BRH1339659 | 0 |
| BRH1339660 | 0 |
| BRH1339662 | 0 |
| BRH1339664 | 6 |
| BRH1339666 | 0 |
| BRH1339667 | 0 |
| BRH1339668 | 2 |
| BRH1339669 | 20 |
| BRH1339670 | 0 |
| 171081AAB0007 | 17 |
| 171081AAB0013 | 2 |
| 171081AAB0021 | 4 |
| 171081AAB0024 | 6 |
| 171081AAB0026 | 10 |
| 171081AAB0031 | 17 |
| 171081AAB0034 | 13 |
| 171081AAB0035 | 0 |
| 171081AAB0036 | 0 |
| 171081AAB0038 | 2 |
| 171081AAB0041 | 0 |
| 171081AAB0042 | 2 |
| 171081AAB0048 | 0 |
| 171081AAB0050 | 1 |
| 171146AAB0012 | 0 |
| 171146AAB0024 | 0 |
| 171146AAB0034 | 12 |
| 171146AAB0035 | 2 |
| 171146AAB0037 | 2 |
| 171146AAB0038 | 1 |
| 171146AAB0039 | 0 |
| 171146AAB0040 | 2 |
| BRH1339651 | 5 |
| BRH1339652 | 0 |
| BRH1339653 | 0 |
| BRH1339654 | 12 |
| BRH1339656 | 0 |
| BRH1339661 | 1 |
| BRH1339663 | 0 |
| BRH1339665 | 0 |
| No of Observations | 114 |
| Average Number | 3.0 |
| Median Number | 1 |
| # of Patients w/0 Pos Results | 45 |
| % Subjects w/0 pos results | 39.5 |
| NON-DEPRESSION POPULATION | |
| BRH1244994 | 0 |
| BRH1244995 | 0 |
| BRH1244996 | 0 |
| BRH1244997 | 0 |
| BRH1244998 | 2 |
| BRH1244999 | 0 |
| BRH1245000 | 1 |
| BRH1245001 | 0 |
| BRH1245002 | 0 |
| BRH1245004 | 0 |
| BRH1245007 | 0 |
| BRH1245008 | 0 |
| BRH1245009 | 1 |
| BRH1245010 | 2 |
| BRH1245011 | 2 |
| BRH1245014 | 0 |
| BRH1245015 | 0 |
| BRH1245018 | 1 |
| BRH1245019 | 0 |
| BRH1245022 | 5 |
| BRH1245023 | 1 |
| BRH1245024 | 1 |
| BRH1245026 | 3 |
| BRH1245029 | 0 |
| BRH1245030 | 0 |
| BRH1245031 | 0 |
| BRH1245032 | 0 |
| BRH1245033 | 0 |
| BRH1245035 | 0 |
| BRH1245037 | 0 |
| BRH1245038 | 0 |
| BRH1245039 | 7 |
| BRH1245040 | 1 |
| BRH1245041 | 0 |
| BRH1267328 | 8 |
| BRH1267329 | 0 |
| BRH1267330 | 0 |
| BRH1267332 | 0 |
| BRH1267333 | 0 |
| BRH1267334 | 8 |
| BRH1267335 | 2 |
| BRH1267337 | 0 |
| BRH1267338 | 0 |
| BRH1267339 | 0 |
| BRH1267340 | 4 |
| BRH1267341 | 0 |
| BRH1267343 | 2 |
| BRH1267345 | 0 |
| BRH1267346 | 0 |
| BRH1267347 | 0 |
| BRH1267349 | 0 |
| BRH1244900 | 0 |
| BRH1244901 | 3 |
| BRH1244902 | 0 |
| BRH1244903 | 0 |
| BRH1244904 | 0 |
| BRH1244905 | 0 |
| BRH1244906 | 7 |
| BRH1244907 | 0 |
| BRH1244908 | 1 |
| BRH1244909 | 0 |
| BRH1244910 | 1 |

TABLE 5B-continued

| Sample ID | # of Positive Results Based on 95th Percentile |
|---|---|
| BRH1244911 | 1 |
| BRH1244912 | 0 |
| BRH1244913 | 0 |
| BRH1244914 | 3 |
| BRH1244915 | 0 |
| BRH1244916 | 9 |
| BRH1244917 | 4 |
| BRH1244918 | 0 |
| BRH1244920 | 1 |
| BRH1244921 | 0 |
| BRH1244922 | 11 |
| BRH1244923 | 0 |
| BRH1244924 | 0 |
| BRH1244925 | 1 |
| BRH1244926 | 9 |
| BRH1244928 | 0 |
| BRH1244929 | 1 |
| BRH1244931 | 0 |
| BRH1244932 | 0 |
| BRH1244933 | 3 |
| BRH1244934 | 1 |
| BRH1244938 | 1 |
| BRH1244939 | 0 |
| BRH1244940 | 0 |
| BRH1244941 | 0 |
| BRH1244942 | 3 |
| BRH1244943 | 1 |
| BRH1244944 | 3 |
| BRH1244945 | 1 |
| BRH1244946 | 3 |
| BRH1244947 | 0 |
| BRH1244948 | 0 |
| BRH1244949 | 0 |
| BRH1244950 | 0 |
| BRH1244951 | 0 |
| BRH1244952 | 0 |
| BRH1244953 | 1 |
| BRH1244954 | 0 |
| BRH1244956 | 13 |
| BRH1244959 | 0 |
| BRH1244960 | 0 |
| BRH1244961 | 0 |
| BRH1244962 | 0 |
| BRH1244963 | 0 |
| BRH1244964 | 3 |
| BRH1244965 | 0 |
| BRH1244967 | 0 |
| BRH1244969 | 0 |
| BRH1244970 | 0 |
| BRH1244971 | 0 |
| BRH1244972 | 0 |
| BRH1244973 | 0 |
| BRH1244974 | 0 |
| BRH1244975 | 0 |
| BRH1244976 | 0 |
| BRH1244977 | 0 |
| BRH1244979 | 0 |
| BRH1244980 | 0 |
| BRH1244981 | 0 |
| BRH1244982 | 0 |
| BRH1244983 | 0 |
| BRH1244985 | 0 |
| BRH1244987 | 0 |
| BRH1244988 | 1 |
| BRH1244991 | 0 |
| BRH1244992 | 1 |
| BRH1267320 | 0 |
| BRH1267322 | 1 |
| BRH1267323 | 0 |
| BRH1267325 | 0 |
| No of Observations | 132 |
| Average Number | 1.1 |
| Median Number | 0 |
| # of Patients w/0 Pos Results | 88 |
| % Subjects w/0 pos results | 66.7 |

TABLE 6A

Summary statistics

| Variable | Depression_90th_percentile Depression 90th percentile |
|---|---|
| Sample size | 114 |
| Lowest value | 0.0000 |
| Highest value | 20.0000 |
| Arithmetic mean | 4.4211 |
| 95% CI for the mean | 3.4414 to 5.4007 |
| Median | 2.0000 |
| 95% CI for the median | 1.0000 to 4.0000 |
| Variance | 27.8742 |
| Standard deviation | 5.2796 |
| Relative standard deviation | 1.1942 (119.42%) |
| Standard error of the mean | 0.4945 |
| Coefficient of Skewness | 1.3689 ($P < 0.0001$) |
| Coefficient of Kurtosis | 1.0336 ($P = 0.0576$) |
| D'Agostino-Pearson test for Normal distribution | reject Normality ($P < 0.0001$) |

| Percentiles | | 95% Confidence interval |
|---|---|---|
| 2.5 | 0.0000 | |
| 5 | 0.0000 | 0.0000 to 0.0000 |
| 10 | 0.0000 | 0.0000 to 0.0000 |
| 25 | 0.0000 | 0.0000 to 1.0000 |
| 75 | 7.0000 | 5.0000 to 8.0000 |
| 90 | 13.1000 | 9.9660 to 17.9482 |
| 95 | 17.8000 | 13.8680 to 18.8568 |
| 97.5 | 18.0000 | |

TABLE 6B

Summary statistics

| Variable | Depression_95th_percentile Depression 95th percentile |
|---|---|
| Sample size | 114 |
| Lowest value | 0.0000 |
| Highest value | 20.0000 |
| Arithmetic mean | 3.0000 |
| 95% CI for the mean | 2.1768 to 3.8232 |
| Median | 1.0000 |
| 95% CI for the median | 1.0000 to 2.0000 |
| Variance | 19.6814 |
| Standard deviation | 4.4364 |
| Relative standard deviation | 1.4788 (147.88%) |
| Standard error of the mean | 0.4155 |
| Coefficient of Skewness | 1.9281 ($P < 0.0001$) |
| Coefficient of Kurtosis | 3.3178 ($P = 0.0002$) |
| D'Agostino-Pearson test for Normal distribution | reject Normality ($P < 0.0001$) |

| Percentiles | | 95% Confidence interval |
|---|---|---|
| 2.5 | 0.0000 | |
| 5 | 0.0000 | 0.0000 to 0.0000 |
| 10 | 0.0000 | 0.0000 to 0.0000 |
| 25 | 0.0000 | 0.0000 to 0.0000 |
| 75 | 4.0000 | 2.0000 to 6.0000 |
| 90 | 9.1000 | 6.0000 to 12.9482 |
| 95 | 12.8000 | 9.8680 to 17.0000 |
| 97.5 | 17.0000 | |

TABLE 7A

Summary statistics

| Variable | Non_Depression_90th_percentile Non-Depression 90th percentile |
|---|---|
| Sample size | 132 |
| Lowest value | 0.0000 |

TABLE 7A-continued

Summary statistics

| | |
|---|---|
| Highest value | 18.0000 |
| Arithmetic mean | 1.9621 |
| 95% CI for the mean | 1.3602 to 2.5640 |
| Median | 0.0000 |
| 95% CI for the median | 0.0000 to 1.0000 |
| Variance | 12.2199 |
| Standard deviation | 3.4957 |
| Relative standard deviation | 1.7816 (178.16%) |
| Standard error of the mean | 0.3043 |
| Coefficient of Skewness | 2.4457 (P < 0.0001) |
| Coefficient of Kurtosis | 5.8138 (P < 0.0001) |
| D'Agostino-Pearson test for Normal distribution | reject Normality (P < 0.0001) |

| Percentiles | | 95% Confidence interval |
|---|---|---|
| 2.5 | 0.0000 | |
| 5 | 0.0000 | 0.0000 to 0.0000 |
| 10 | 0.0000 | 0.0000 to 0.0000 |
| 25 | 0.0000 | 0.0000 to 0.0000 |
| 75 | 2.0000 | 1.0000 to 3.0000 |
| 90 | 6.0000 | 4.0000 to 11.0000 |
| 95 | 11.0000 | 6.6178 to 14.0000 |
| 97.5 | 12.4000 | |

TABLE 7B

Summary statistics

| Variable | Non_Depression_95th_percentile<br>Non-Depression 95th percentile |
|---|---|
| Sample size | 132 |
| Lowest value | 0.0000 |
| Highest value | 13.0000 |
| Arithmetic mean | 1.0530 |
| 95% CI for the mean | 0.6548 to 1.4512 |
| Median | 0.0000 |
| 95% CI for the median | 0.0000 to 0.0000 |
| Variance | 5.3483 |
| Standard deviation | 2.3126 |
| Relative standard deviation | 2.1962 (219.62%) |
| Standard error of the mean | 0.2013 |
| Coefficient of Skewness | 3.0440 (P < 0.0001) |
| Coefficient of Kurtosis | 9.7586 (P < 0.0001) |
| D'Agostino-Pearson test for Normal distribution | reject Normality (P < 0.0001) |

| Percentiles | | 95% Confidence interval |
|---|---|---|
| 2.5 | 0.0000 | |
| 5 | 0.0000 | 0.0000 to 0.0000 |
| 10 | 0.0000 | 0.0000 to 0.0000 |
| 25 | 0.0000 | 0.0000 to 0.0000 |
| 75 | 1.0000 | 1.0000 to 1.9868 |
| 90 | 3.0000 | 2.0000 to 7.0000 |
| 95 | 7.0000 | 3.0000 to 9.6200 |
| 97.5 | 9.0000 | |

TABLE 8A

Summary statistics

| Variable | Depression_90th_percentile_1<br>Depression 90th percentile_1 |
|---|---|

Back-transformed after logarithmic transformation.

| | |
|---|---|
| Sample size | 114 |
| Lowest value | 0.1000 |
| Highest value | 20.0000 |
| Geometric mean | 1.4587 |
| 95% CI for the mean | 1.0357 to 2.0544 |

TABLE 8A-continued

Summary statistics

| | |
|---|---|
| Median | 2.0000 |
| 95% CI for the median | 1.0000 to 4.0000 |
| Coefficient of Skewness | −0.4070 (P = 0.0728) |
| Coefficient of Kurtosis | −1.2637 (P < 0.0001) |
| D'Agostino-Pearson test for Normal distribution | reject Normality (P < 0.0001) |

| Percentiles | | 95% Confidence interval |
|---|---|---|
| 2.5 | 0.10000 | |
| 5 | 0.10000 | 0.10000 to 0.10000 |
| 10 | 0.10000 | 0.10000 to 0.10000 |
| 25 | 0.10000 | 0.10000 to 1.0000 |
| 75 | 7.0000 | 5.0000 to 8.0000 |
| 90 | 13.0967 | 9.9160 to 17.9468 |
| 95 | 17.7954 | 13.8637 to 18.8535 |
| 97.5 | 18.0000 | |

TABLE 8B

Summary statistics

| Variable | Depression_95th_percentile_1<br>Depression 95th percentile_1 |
|---|---|

Back-transformed after logarithmic transformation.

| | |
|---|---|
| Sample size | 114 |
| Lowest value | 0.1000 |
| Highest value | 20.0000 |
| Geometric mean | 0.8117 |
| 95% CI for the mean | 0.5753 to 1.1453 |
| Median | 1.0000 |
| 95% CI for the median | 1.0000 to 2.0000 |
| Coefficient of Skewness | 0.04587 (P = 0.8348) |
| Coefficient of Kurtosis | −1.5224 (P < 0.0001) |
| D'Agostino-Pearson test for Normal distribution | reject Normality (P < 0.0001) |

| Percentiles | | 95% Confidence interval |
|---|---|---|
| 2.5 | 0.10000 | |
| 5 | 0.10000 | 0.10000 to 0.10000 |
| 10 | 0.10000 | 0.10000 to 0.10000 |
| 25 | 0.10000 | 0.10000 to 0.10000 |
| 75 | 4.0000 | 2.0000 to 6.0000 |
| 90 | 9.0953 | 6.0000 to 12.9462 |
| 95 | 12.7935 | 9.8619 to 17.0000 |
| 97.5 | 17.0000 | |

TABLE 9A

Summary statistics

| Variable | Non_Depression_90th_percentile_1<br>Non-Depression 90th percentile 1 |
|---|---|

Back-transformed after logarithmic transformation.

| | |
|---|---|
| Sample size | 132 |
| Lowest value | 0.1000 |
| Highest value | 18.0000 |
| Geometric mean | 0.4892 |
| 95% CI for the mean | 0.3614 to 0.6622 |
| Median | 0.10000 |
| 95% CI for the median | 0.10000 to 1.0000 |
| Coefficient of Skewness | 0.4536 (P = 0.0336) |
| Coefficient of Kurtosis | −1.3443 (P < 0.0001) |
| D'Agostino-Pearson test for Normal distribution | reject Normality (P < 0.0001) |

TABLE 9A-continued

Summary statistics

| Percentiles | | 95% Confidence interval |
|---|---|---|
| 2.5 | 0.10000 | |
| 5 | 0.10000 | 0.10000 to 0.10000 |
| 10 | 0.10000 | 0.10000 to 0.10000 |
| 25 | 0.10000 | 0.10000 to 0.10000 |
| 75 | 2.0000 | 1.0000 to 3.0000 |
| 90 | 6.0000 | 4.0000 to 11.0000 |
| 95 | 11.0000 | 6.5995 to 14.0000 |
| 97.5 | 12.3757 | |

TABLE 9B

Summary statistics

| Variable | Non_Depression_95th_percentile_1<br>Non-Depression 95th percentile_1 |
|---|---|

Back-transformed after logarithmic transformation.

| | |
|---|---|
| Sample size | 132 |
| Lowest value | 0.1000 |
| Highest value | 13.0000 |
| Geometric mean | 0.2788 |
| 95% CI for the mean | 0.2141 to 0.3631 |
| Median | 0.10000 |
| 95% CI for the median | 0.10000 to 0.10000 |
| Coefficient of Skewness | 1.0472 (P < 0.0001) |
| Coefficient of Kurtosis | −0.4494 (P = 0.2192) |
| D'Agostino-Pearson test<br>for Normal distribution | reject Normality<br>(P < 0.0001) |

| Percentiles | | 95% Confidence interval |
|---|---|---|
| 2.5 | 0.10000 | |
| 5 | 0.10000 | 0.10000 to 0.10000 |
| 10 | 0.10000 | 0.10000 to 0.10000 |
| 25 | 0.10000 | 0.10000 to 0.10000 |
| 75 | 1.0000 | 1.0000 to 1.9818 |
| 90 | 3.0000 | 2.0000 to 7.0000 |
| 95 | 7.0000 | 3.0000 to 9.5777 |
| 97.5 | 9.0000 | |

TABLE 10A

Independent samples t-test

Sample 1

| Variable | Depression_90th_percentile_1<br>Depression 90th percentile_1 |
|---|---|

Sample 2

| Variable | Non_Depression_90th_percentile_1<br>Non-Depression 90th percentile_1 |
|---|---|

Back-transformed after logarithmic transformation.

| | Sample 1 | Sample 2 |
|---|---|---|
| Sample size | 114 | 132 |
| Geometric mean | 1.4587 | 0.4892 |
| 95% CI for the mean | 1.0357 to 2.0544 | 0.3614 to 0.6622 |
| Variance of Logs | 0.6423 | 0.5832 |
| F-test for equal variances | P = 0.592 | |

T-test (assuming equal variances)

Difference on Log-transformed scale

| | |
|---|---|
| Difference | −0.4745 |
| Standard Error | 0.09991 |
| 95% CI of difference | −0.6713 to −0.2777 |
| Test statistic t | −4.749 |

TABLE 10A-continued

| | |
|---|---|
| Degrees of Freedom (DF) | 244 |
| Two-tailed probability | P < 0.0001 |

Back-transformed results

| | |
|---|---|
| Ratio of geometric means | 0.3354 |
| 95% CI of ratio | 0.2132 to 0.5276 |

TABLE 10B

Independent samples t-test

Sample 1

| Variable | Depression_95th_percentile_1<br>Depression 95th percentile_1 |
|---|---|

Sample 2

| Variable | Non_Depression_95th_percentile_1<br>Non-Depression 95th percentile_1 |
|---|---|

Back-transformed after logarithmic transformation.

| | Sample 1 | Sample 2 |
|---|---|---|
| Sample size | 114 | 132 |
| Geometric mean | 0.8117 | 0.2788 |
| 95% CI for the mean | 0.5753 to 1.1453 | 0.2141 to 0.3631 |
| Variance of Logs | 0.6490 | 0.4434 |
| F-test for equal variances | P = 0.036 | |

T-test (assuming equal variances)

Difference on Log-transformed scale

| | |
|---|---|
| Difference | −0.4641 |
| Standard Error | 0.09384 |
| 95% CI of difference | −0.6489 to −0.2792 |
| Test statistic t | −4.946 |
| Degrees of Freedom (DF) | 244 |
| Two-tailed probability | P < 0.0001 |

Back-transformed results

| | |
|---|---|
| Ratio of geometric means | 0.3435 |
| 95% CI of ratio | 0.2244 to 0.5257 |

TABLE 11A

Mann-Whitney test (independent samples)

Sample 1

| Variable | Depression_90th_percentile<br>Depression 90th percentile |
|---|---|

Sample 2

| Variable | Non_Depression_90th_percentile<br>Non-Depression 90th percentile |
|---|---|

| | Sample 1 | Sample 2 |
|---|---|---|
| Sample size | 114 | 132 |
| Lowest value | 0.0000 | 0.0000 |
| Highest value | 20.0000 | 18.0000 |
| Median | 2.0000 | 0.0000 |
| 95% CI for the median | 1.0000 to 4.0000 | 0.0000 to 1.0000 |
| Interquartile range | 0.0000 to 7.0000 | 0.0000 to 2.0000 |

Mann-Whitney test (independent samples)

| | |
|---|---|
| Average rank of first group | 145.2149 |
| Average rank of second group | 104.7462 |
| Mann-Whitney U | 5048.50 |
| Test statistic Z (corrected for ties) | 4.609 |
| Two-tailed probability | P < 0.0001 |

TABLE 11B

| Mann-Whitney test (independent samples) | | |
|---|---|---|
| Sample 1 | | |
| Variable | Depression_95th_percentile Depression 95th percentile | |
| Sample 2 | | |
| Variable | Non_Depression_95th_percentile Non-Depression 95th percentile | |
| | Sample 1 | Sample 2 |
| Sample size | 114 | 132 |
| Lowest value | 0.0000 | 0.0000 |
| Highest value | 20.0000 | 13.0000 |
| Median | 1.0000 | 0.0000 |
| 95% CI for the median | 1.0000 to 2.0000 | 0.0000 to 0.0000 |
| Interquartile range | 0.0000 to 4.0000 | 0.0000 to 1.0000 |

| Mann-Whitney test (independent samples) | |
|---|---|
| Average rank of first group | 144.4737 |
| Average rank of second group | 105.3864 |
| Mann-Whitney U | 5133.00 |
| Test statistic Z (corrected for ties) | 4.684 |
| Two-tailed probability | P < 0.0001 |

TABLE 12A

| ROC curve | |
|---|---|
| Variable | Depression_Test_90th Depression Test_90th |
| Classification variable | Diagnosis_1_Depression_0_Non_Depression_ Diagnosis(1_Depression 0_Non-Depression) |
| Sample size | 246 |
| Positive group [a] | 114 (46.34%) |
| Negative group [b] | 132 (53.66%) |

[a] Diagnosis_1_Depression_0_Non_Depression_ = 1
[b] Diagnosis_1_Depression_0_Non_Depression_ = 0

| Disease prevalence (%) | unknown |
|---|---|
| Area under the ROC curve (AUC) | |
| Area under the ROC curve (AUC) | 0.665 |
| Standard Error [a] | 0.0336 |
| 95% Confidence interval [b] | 0.602 to 0.723 |
| z statistic | 4.893 |
| Significance level P (Area = 0.5) | <0.0001 |

[a] DeLong et al., 1988
[b] Binomial exact

| Youden index | |
|---|---|
| Youden index J | 0.2472 |
| 95% Confidence interval [a] | 0.09744 to 0.3186 |
| Associated criterion | >4 |
| 95% Confidence interval [a] | >2.241316576 to >6 |
| Sensitivity | 36.84 |
| Specificity | 87.88 |

[a] $BC_a$ bootstrap confidence interval (1000 iterations: random number seed: 978).

TABLE 12B

| ROC curve | |
|---|---|
| Variable | Depression_Test_95th Depression Test_95th |
| Classification variable | Diagnosis_1_Depression_0_Non_Depression_ Diagnosis(1_Depression 0_Non-Depression) |
| Sample size | 246 |
| Positive group [a] | 114 (46.34%) |
| Negative group [b] | 132 (53.66%) |

[a] Diagnosis_1_Depression_0_Non_Depression_ = 1
[b] Diagnosis_1_Depression_0_Non_Depression_ = 0

| Disease prevalence (%) | unknown |
|---|---|
| Area under the ROC curve (AUC) | |
| Area under the ROC curve (AUC) | 0.659 |
| Standard Error [a] | 0.0322 |
| 95% Confidence interval [b] | 0.596 to 0.718 |
| z statistic | 4.934 |
| Significance level P (Area = 0.5) | <0.0001 |

TABLE 12B-continued

[a] DeLong et al., 1988
[b] Binomial exact

Youden index

| | |
|---|---|
| Youden index J | 0.2719 |
| 95% Confidence interval [a] | 0.1567 to 0.3743 |
| Associated criterion | >0 |
| 95% Confidence interval [a] | >0 to >1 |
| Sensitivity | 60.53 |
| Specificity | 66.67 |

[a] $BC_a$ bootstrap confidence interval (1000 iterations: random number seed: 978).

TABLE 13A

Performance Metrics in Predicting Depression Status from Number of Positive Foods Using 90th Percentile of ELISA Signal to determine Positive

| Sex | No. of Positive Foods as Cutoff | Sensitivity | Specificity | Positive Predictive Value | Negative Predictive Value | Overall Percent Agreement |
|---|---|---|---|---|---|---|
| FEMALE | 1 | 0.83 | 0.39 | 0.69 | 0.59 | 0.66 |
| | 2 | 0.70 | 0.56 | 0.72 | 0.53 | 0.65 |
| | 3 | 0.58 | 0.67 | 0.74 | 0.50 | 0.62 |
| | 4 | 0.51 | 0.72 | 0.75 | 0.47 | 0.59 |
| | 5 | 0.45 | 0.76 | 0.76 | 0.46 | 0.57 |
| | 6 | 0.41 | 0.81 | 0.78 | 0.45 | 0.56 |
| | 7 | 0.35 | 0.85 | 0.79 | 0.44 | 0.54 |
| | 8 | 0.30 | 0.87 | 0.79 | 0.43 | 0.52 |
| | 9 | 0.25 | 0.89 | 0.79 | 0.42 | 0.49 |
| | 10 | 0.22 | 0.90 | 0.79 | 0.42 | 0.48 |
| | 11 | 0.20 | 0.91 | 0.79 | 0.41 | 0.47 |
| | 12 | 0.18 | 0.91 | 0.78 | 0.41 | 0.46 |
| | 13 | 0.15 | 0.93 | 0.77 | 0.40 | 0.45 |
| | 14 | 0.12 | 0.94 | 0.77 | 0.40 | 0.43 |
| | 15 | 0.10 | 0.95 | 0.80 | 0.39 | 0.43 |
| | 16 | 0.09 | 0.97 | 0.80 | 0.39 | 0.42 |
| | 17 | 0.08 | 0.97 | 0.83 | 0.39 | 0.42 |
| | 18 | 0.07 | 0.97 | 0.88 | 0.39 | 0.42 |
| | 19 | 0.07 | 1.00 | 1.00 | 0.39 | 0.41 |
| | 20 | 0.06 | 1.00 | 1.00 | 0.39 | 0.41 |
| | 21 | 0.06 | 1.00 | 1.00 | 0.39 | 0.41 |
| | 22 | 0.05 | 1.00 | 1.00 | 0.39 | 0.41 |
| | 23 | 0.04 | 1.00 | 1.00 | 0.39 | 0.40 |
| | 24 | 0.02 | 1.00 | 1.00 | 0.39 | 0.40 |
| | 25 | 0.02 | 1.00 | 1.00 | 0.38 | 0.39 |
| | 26 | 0.00 | 1.00 | 1.00 | 0.38 | 0.38 |

TABLE 13B

Performance Metrics in Predicting Depression Status from Number of Positive Foods Using 90th Percentile of ELISA Signal to determine Positive

| Sex | No. of Positive Foods as Cutoff | Sensitivity | Specificity | Positive Predictive Value | Negative Predictive Value | Overall Percent Agreement |
|---|---|---|---|---|---|---|
| MALE | 1 | 0.86 | 0.38 | 0.34 | 0.88 | 0.51 |
| | 2 | 0.74 | 0.57 | 0.39 | 0.86 | 0.62 |
| | 3 | 0.60 | 0.69 | 0.42 | 0.83 | 0.67 |
| | 4 | 0.48 | 0.76 | 0.42 | 0.80 | 0.68 |
| | 5 | 0.42 | 0.81 | 0.46 | 0.79 | 0.71 |
| | 6 | 0.40 | 0.86 | 0.50 | 0.79 | 0.73 |
| | 7 | 0.38 | 0.88 | 0.54 | 0.79 | 0.74 |
| | 8 | 0.35 | 0.89 | 0.55 | 0.79 | 0.75 |
| | 9 | 0.33 | 0.90 | 0.55 | 0.78 | 0.75 |
| | 10 | 0.30 | 0.91 | 0.56 | 0.78 | 0.75 |
| | 11 | 0.27 | 0.92 | 0.57 | 0.78 | 0.75 |
| | 12 | 0.25 | 0.93 | 0.57 | 0.77 | 0.75 |
| | 13 | 0.24 | 0.94 | 0.57 | 0.77 | 0.75 |

TABLE 13B-continued

Performance Metrics in Predicting Depression Status from Number of Positive Foods Using 90th Percentile of ELISA Signal to determine Positive

| Sex | No. of Positive Foods as Cutoff | Sensitivity | Specificity | Positive Predictive Value | Negative Predictive Value | Overall Percent Agreement |
|---|---|---|---|---|---|---|
| | 14 | 0.21 | 0.94 | 0.57 | 0.76 | 0.74 |
| | 15 | 0.19 | 0.94 | 0.57 | 0.76 | 0.74 |
| | 16 | 0.17 | 0.95 | 0.57 | 0.76 | 0.74 |
| | 17 | 0.14 | 0.96 | 0.50 | 0.75 | 0.74 |
| | 18 | 0.13 | 0.96 | 0.50 | 0.75 | 0.74 |
| | 19 | 0.11 | 0.96 | 0.60 | 0.75 | 0.74 |
| | 20 | 0.11 | 0.98 | 0.67 | 0.75 | 0.74 |
| | 21 | 0.10 | 0.98 | 0.67 | 0.75 | 0.74 |
| | 22 | 0.10 | 0.98 | 0.75 | 0.75 | 0.75 |
| | 23 | 0.06 | 1.00 | 1.00 | 0.74 | 0.75 |
| | 24 | 0.05 | 1.00 | 1.00 | 0.74 | 0.74 |
| | 25 | 0.00 | 1.00 | 1.00 | 0.73 | 0.73 |
| | 26 | 0.00 | 1.00 | 1.00 | 0.73 | 0.73 |

TABLE 14A

Performance Metrics in Predicting Depression Status from Number of Positive Foods Using 95th Percentile of ELISA Signal to determine Positive

| Sex | No. of Positive Foods as Cutoff | Sensitivity | Specificity | Positive Predictive Value | Negative Predictive Value | Overall Percent Agreement |
|---|---|---|---|---|---|---|
| FEMALE | 1 | 0.71 | 0.55 | 0.72 | 0.53 | 0.65 |
| | 2 | 0.54 | 0.70 | 0.74 | 0.48 | 0.60 |
| | 3 | 0.44 | 0.77 | 0.76 | 0.46 | 0.57 |
| | 4 | 0.36 | 0.82 | 0.77 | 0.44 | 0.54 |
| | 5 | 0.30 | 0.86 | 0.78 | 0.43 | 0.51 |
| | 6 | 0.25 | 0.90 | 0.81 | 0.43 | 0.50 |
| | 7 | 0.21 | 0.91 | 0.80 | 0.42 | 0.48 |
| | 8 | 0.18 | 0.93 | 0.80 | 0.41 | 0.47 |
| | 9 | 0.15 | 0.94 | 0.80 | 0.40 | 0.45 |
| | 10 | 0.12 | 0.95 | 0.80 | 0.40 | 0.44 |
| | 11 | 0.09 | 0.97 | 0.80 | 0.39 | 0.43 |
| | 12 | 0.08 | 0.97 | 0.83 | 0.39 | 0.42 |
| | 13 | 0.06 | 0.97 | 0.86 | 0.39 | 0.41 |
| | 14 | 0.06 | 1.00 | 1.00 | 0.39 | 0.41 |
| | 15 | 0.05 | 1.00 | 1.00 | 0.39 | 0.41 |
| | 16 | 0.05 | 1.00 | 1.00 | 0.39 | 0.41 |
| | 17 | 0.04 | 1.00 | 1.00 | 0.39 | 0.41 |
| | 18 | 0.04 | 1.00 | 1.00 | 0.39 | 0.40 |
| | 19 | 0.04 | 1.00 | 1.00 | 0.39 | 0.40 |
| | 20 | 0.02 | 1.00 | 1.00 | 0.39 | 0.40 |
| | 21 | 0.02 | 1.00 | 1.00 | 0.38 | 0.39 |
| | 22 | 0.02 | 1.00 | 1.00 | 0.38 | 0.39 |
| | 23 | 0.02 | 1.00 | 1.00 | 0.38 | 0.39 |
| | 24 | 0.00 | 1.00 | 1.00 | 0.38 | 0.38 |
| | 25 | 0.00 | 1.00 | 1.00 | 0.38 | 0.38 |
| | 26 | 0.00 | 1.00 | . | 0.38 | 0.38 |

TABLE 14B

Performance Metrics in Predicting Depression Status from Number of Positive Foods Using 95th Percentile of ELISA Signal to determine Positive

| Sex | No. of Positive Foods as Cutoff | Sensitivity | Specificity | Positive Predictive Value | Negative Predictive Value | Overall Percent Agreement |
|---|---|---|---|---|---|---|
| MALE | 1 | 0.75 | 0.54 | 0.38 | 0.85 | 0.59 |
| | 2 | 0.59 | 0.75 | 0.46 | 0.83 | 0.70 |
| | 3 | 0.48 | 0.83 | 0.50 | 0.81 | 0.74 |
| | 4 | 0.36 | 0.88 | 0.53 | 0.79 | 0.74 |
| | 5 | 0.33 | 0.90 | 0.55 | 0.78 | 0.75 |

TABLE 14B-continued

Performance Metrics in Predicting Depression Status from Number of Positive Foods Using 95th Percentile of ELISA Signal to determine Positive

| Sex | No. of Positive Foods as Cutoff | Sensitivity | Specificity | Positive Predictive Value | Negative Predictive Value | Overall Percent Agreement |
|---|---|---|---|---|---|---|
| | 6 | 0.30 | 0.92 | 0.56 | 0.78 | 0.75 |
| | 7 | 0.27 | 0.92 | 0.57 | 0.77 | 0.75 |
| | 8 | 0.24 | 0.94 | 0.57 | 0.77 | 0.75 |
| | 9 | 0.22 | 0.94 | 0.60 | 0.77 | 0.75 |
| | 10 | 0.20 | 0.96 | 0.60 | 0.76 | 0.75 |
| | 11 | 0.18 | 0.96 | 0.60 | 0.76 | 0.75 |
| | 12 | 0.17 | 0.96 | 0.67 | 0.76 | 0.75 |
| | 13 | 0.16 | 0.98 | 0.67 | 0.76 | 0.75 |
| | 14 | 0.14 | 0.98 | 0.67 | 0.75 | 0.75 |
| | 15 | 0.12 | 0.98 | 0.67 | 0.75 | 0.75 |
| | 16 | 0.10 | 0.98 | 0.75 | 0.75 | 0.75 |
| | 17 | 0.09 | 1.00 | 1.00 | 0.75 | 0.75 |
| | 18 | 0.09 | 1.00 | 1.00 | 0.75 | 0.75 |
| | 19 | 0.07 | 1.00 | 1.00 | 0.75 | 0.75 |
| | 20 | 0.06 | 1.00 | 1.00 | 0.74 | 0.75 |
| | 21 | 0.06 | 1.00 | 1.00 | 0.74 | 0.75 |
| | 22 | 0.06 | 1.00 | 1.00 | 0.74 | 0.75 |
| | 23 | 0.05 | 1.00 | 1.00 | 0.74 | 0.74 |
| | 24 | 0.00 | 1.00 | 1.00 | 0.73 | 0.73 |
| | 25 | 0.00 | 1.00 | 1.00 | 0.73 | 0.73 |
| | 26 | 0.00 | 1.00 | . | 0.73 | 0.73 |

What is claimed is:

1. A depression test panel consisting essentially of:
a plurality of distinct depression trigger food preparations immobilized to an individually addressable solid carrier;
wherein all of the distinct food preparations immobilized to the solid carrier are selected from the group consisting of almond, tomato, tobacco, carrot, orange, cucumber, broccoli, lettuce, malt, cantaloupe, corn, wheat, honey, chocolate, oat, avocado, rye, strawberry, cauliflower, safflower, tea, banana, squashes, green pepper, butter, buckwheat, rice, soybean, grapefruit, oyster, brewer's yeast, peach, cane sugar, cow's milk, and spinach;
wherein the solid carrier includes at least twelve food preparations.

2. The test panel of claim 1, wherein all of the distinct food preparations immobilized to the solid carrier are selected from the group consisting of almond, tomato, tobacco, carrot, orange, cucumber, broccoli, lettuce, malt, cantaloupe, corn, wheat, honey, chocolate, oat, avocado, rye, strawberry, cauliflower, safflower, tea, banana, squashes, green pepper, butter, buckwheat, rice, soybean, grapefruit, oyster, and brewer's yeast.

3. The test panel of claim 1, wherein all of the distinct food preparations immobilized to the solid carrier are selected from the group consisting of almond, tomato, tobacco, carrot, orange, cucumber, broccoli, lettuce, malt, cantaloupe, corn, wheat, honey, chocolate, oat, avocado, rye, strawberry, cauliflower, safflower, tea, banana, squashes, green pepper, and butter.

4. The test kit panel of claim 1, wherein all of the distinct food preparations immobilized to the solid carrier are selected from the group consisting of almond, tomato, tobacco, carrot, orange, cucumber, broccoli, lettuce, malt, cantaloupe, corn, wheat, honey, chocolate, oat, avocado, rye, strawberry, cauliflower, safflower, tea, and banana.

5. The test kit panel of claim 1, wherein the plurality of distinct depression trigger food preparations consists of crude filtered aqueous extracts, processed aqueous extracts, or a combination thereof.

6. The test kit panel of claim 1, wherein the solid carrier is selected from the group consisting of an array, a micro well plate, a dipstick, a membrane-bound array, a bead, an electrical sensor, a chemical sensor, a microchip or an adsorptive film.

7. The test kit panel of claim 1, wherein the solid carrier includes at least 26 distinct depression trigger food preparations.

8. The test kit panel of claim 1, wherein the solid carrier is an array.

* * * * *